(12) United States Patent
Grossman et al.

(10) Patent No.: US 11,369,114 B2
(45) Date of Patent: *Jun. 28, 2022

(54) ANTIMICROBIAL COATINGS COMPRISING ORGANOSILANE HOMOPOLYMERS

(71) Applicant: ALLIED BIOSCIENCE, INC., Plano, TX (US)

(72) Inventors: Gavri Grossman, Dallas, TX (US); Jie Fang, Carrollton, TX (US); Parham Asgari, Arlington, TX (US); Maha El-Sayed, Fremont, CA (US); Craig Grossman, Point Roberts, WA (US); Daniel Moros, New York, NY (US)

(73) Assignee: Allied Bioscience, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/177,850

(22) Filed: Feb. 17, 2021

(65) Prior Publication Data

US 2021/0169081 A1 Jun. 10, 2021

Related U.S. Application Data

(60) Continuation of application No. 16/591,785, filed on Oct. 3, 2019, now Pat. No. 10,993,441, which is a continuation-in-part of application No. 15/718,997, filed on Sep. 28, 2017, now Pat. No. 10,463,046, which is a division of application No. 15/041,974, filed on Feb. 11, 2016, now Pat. No. 9,918,475, which is a continuation-in-part of application No. 14/932,840, filed on Nov. 4, 2015, now Pat. No. 9,856,360.

(60) Provisional application No. 62/114,998, filed on Feb. 11, 2015, provisional application No. 62/075,020, filed on Nov. 4, 2014.

(51) Int. Cl.

| | | |
|---|---|---|
| *C09D 183/08* | (2006.01) | |
| *A01N 55/00* | (2006.01) | |
| *B05D 1/04* | (2006.01) | |
| *C23C 26/00* | (2006.01) | |
| *C09D 179/02* | (2006.01) | |
| *B05D 7/00* | (2006.01) | |
| *B05D 7/14* | (2006.01) | |
| *B05D 1/02* | (2006.01) | |
| *A01N 33/08* | (2006.01) | |
| *A01N 25/02* | (2006.01) | |
| *C09D 5/14* | (2006.01) | |
| *A61L 2/00* | (2006.01) | |
| *A01N 59/16* | (2006.01) | |
| *C08G 77/26* | (2006.01) | |
| *C09D 183/00* | (2006.01) | |
| *C08K 3/22* | (2006.01) | |
| *C09D 183/06* | (2006.01) | |
| *C07F 7/08* | (2006.01) | |

(52) U.S. Cl.
CPC ............. *A01N 55/00* (2013.01); *A01N 25/02* (2013.01); *A01N 33/08* (2013.01); *A01N 59/16* (2013.01); *A61L 2/00* (2013.01); *B05D 1/02* (2013.01); *B05D 1/04* (2013.01); *B05D 7/14* (2013.01); *B05D 7/544* (2013.01); *C08G 77/26* (2013.01); *C09D 5/14* (2013.01); *C09D 179/02* (2013.01); *C09D 183/08* (2013.01); *C23C 26/00* (2013.01); *C07F 7/081* (2013.01); *C08K 3/22* (2013.01); *C08K 2003/2241* (2013.01); *C09D 183/00* (2013.01); *C09D 183/06* (2013.01)

(58) Field of Classification Search
CPC ... C09D 183/04; C09D 183/06; C09D 183/08
See application file for complete search history.

(56) References Cited

U.S. PATENT DOCUMENTS

| | | | |
|---|---|---|---|
| 3,044,982 A | 7/1962 | Jex et al. | |
| 3,068,199 A | 12/1962 | Sellers | |
| 3,133,108 A | 5/1964 | Finestone | |
| 3,455,725 A | 7/1969 | Jex et al. | |

(Continued)

FOREIGN PATENT DOCUMENTS

| | | |
|---|---|---|
| CN | 1597810 | 3/2005 |
| CN | 102958619 | 3/2013 |

(Continued)

OTHER PUBLICATIONS

IMPI; Office Action dated Oct. 29, 2020 in MX Application No. MX/a/2017/005740.

(Continued)

*Primary Examiner* — Margaret G Moore
(74) *Attorney, Agent, or Firm* — Snell & Wilmer L.L.P.

(57) ABSTRACT

Aqueous antimicrobial coating compositions are disclosed comprising at least one organosilane homopolymer, present as a distribution of polymer chain lengths, and optionally at least one amine. A method of preparing an antimicrobial coating comprises coating a surface with the aqueous antimicrobial coating composition and allowing the composition to dry into a film that exhibits residual antimicrobial efficacy against microorganisms even after mechanical abrasion of the coating. The organosilane homopolymer may comprise only 3-aminopropylsilanetriol homopolymer, mixtures of 3-aminopropylsilanetriol homopolymer, 3-chloropropylsilanetriol homopolymer and 3-(trihydroxysilyl)propyl dimethyloctadecyl ammonium chloride homopolymer, or any one of various unique organosilane homopolymers having multiple amine functionality.

18 Claims, 56 Drawing Sheets

(56) References Cited

U.S. PATENT DOCUMENTS

| | | | |
|---|---|---|---|
| 4,005,025 A | 1/1977 | Kinstedt | |
| 4,048,206 A | 9/1977 | Voronkov et al. | |
| 4,740,538 A | 4/1988 | Sekutowski | |
| 4,865,844 A | 9/1989 | Blank | |
| 5,359,104 A | 10/1994 | Higgs et al. | |
| 5,879,436 A | 3/1999 | Kramer | |
| 5,945,555 A | 8/1999 | Yoshitake | |
| 5,954,869 A | 9/1999 | Elfersy | |
| 6,331,434 B1 | 12/2001 | Decor et al. | |
| 6,759,127 B1 | 7/2004 | Smith et al. | |
| 7,704,561 B2 | 4/2010 | Mehta et al. | |
| 7,884,089 B2 | 2/2011 | Gimvang | |
| 7,939,686 B2 | 5/2011 | Threlkeld et al. | |
| 8,025,120 B2 | 9/2011 | Eddy | |
| 8,491,922 B2 | 7/2013 | Eddy | |
| 8,735,618 B2 | 5/2014 | Ludwig et al. | |
| 8,754,146 B2 | 6/2014 | Ziolkowski | |
| 8,771,375 B2 | 7/2014 | Rodengen et al. | |
| 8,790,623 B2 | 7/2014 | Lalleman | |
| 8,815,351 B2 | 8/2014 | Owens | |
| 8,859,009 B2 | 10/2014 | Nikawa | |
| 8,900,716 B2 | 12/2014 | Hodges et al. | |
| 8,951,341 B2 | 2/2015 | Jaffrennou | |
| 8,956,665 B2 | 2/2015 | Bolkan et al. | |
| 8,999,357 B2 | 4/2015 | Elfersy et al. | |
| 9,028,846 B2 | 5/2015 | Eddy | |
| 9,089,138 B2 | 7/2015 | Higgins et al. | |
| 9,145,536 B2 | 9/2015 | Adamy et al. | |
| 9,265,248 B2 | 2/2016 | Gentle et al. | |
| 9,266,993 B2 | 2/2016 | Stentrup et al. | |
| 9,364,572 B2 | 6/2016 | Peterson et al. | |
| 9,445,600 B2 | 9/2016 | Bui et al. | |
| 9,458,319 B2 | 10/2016 | Maliverney et al. | |
| 9,675,735 B2 | 6/2017 | Eddy | |
| 9,717,249 B2 | 8/2017 | Eddy | |
| 9,796,738 B2 | 10/2017 | Waβmer et al. | |
| 10,010,080 B2 | 7/2018 | Neigel | |
| 10,072,378 B2 | 9/2018 | Baumann | |
| 10,196,559 B1 | 2/2019 | Arvanitakis et al. | |
| 10,280,315 B2 | 5/2019 | Park et al. | |
| 10,308,817 B2 | 6/2019 | Kroke et al. | |
| 10,329,510 B2 | 6/2019 | Wang et al. | |
| 10,582,711 B2 | 3/2020 | Huang | |
| 10,590,284 B2 | 3/2020 | Giovanniello | |
| 10,604,729 B2 | 3/2020 | Hawkins et al. | |
| 10,640,521 B2 | 5/2020 | Venema | |
| 10,758,426 B2 | 9/2020 | Eddy | |
| 10,993,441 B2 * | 5/2021 | Grossman | C23C 18/1258 |
| 11,033,031 B1 * | 6/2021 | Grossman | C09D 179/02 |
| 2003/0101898 A1 | 6/2003 | Standke | |
| 2005/0238839 A1 | 10/2005 | Takagi et al. | |
| 2006/0142459 A1 | 6/2006 | Goebel | |
| 2006/0269760 A1 | 11/2006 | Sugama | |
| 2007/0017567 A1 | 1/2007 | Gronet et al. | |
| 2008/0131594 A1 | 6/2008 | Cho | |
| 2009/0030220 A1 | 1/2009 | Uchibori | |
| 2009/0317624 A1 | 12/2009 | Yoshioka | |
| 2010/0029530 A1 | 2/2010 | Whiteley | |
| 2010/0234506 A1 | 9/2010 | Elizalde | |
| 2011/0000539 A1 | 1/2011 | Gronet | |
| 2011/0086567 A1 | 4/2011 | Hawkins et al. | |
| 2012/0015200 A1 | 1/2012 | Ali | |
| 2013/0040078 A1 | 2/2013 | Scharfe et al. | |
| 2013/0167754 A1 | 7/2013 | Wassmer | |
| 2013/0237409 A1 | 9/2013 | Sambandam | |
| 2014/0158018 A1 | 6/2014 | Geoffrion et al. | |
| 2015/0020712 A1 | 1/2015 | Wosylus | |
| 2016/0097595 A1 | 4/2016 | Ritchey | |
| 2018/0280582 A1 * | 10/2018 | Grossman | A01N 55/00 |

FOREIGN PATENT DOCUMENTS

| | | |
|---|---|---|
| CN | 103080117 | 5/2013 |
| CN | 103087567 | 5/2013 |
| CN | 103087571 | 5/2013 |
| CN | 103305029 | 9/2013 |
| CN | 103351916 | 10/2013 |
| CN | 105461930 | 4/2016 |
| CN | 107312396 | 11/2017 |
| CN | 107903734 | 4/2018 |
| DE | 102013208034 | 11/2013 |
| EP | 1002889 | 5/2000 |
| EP | 1971206 | 9/2008 |
| EP | 1992230 | 11/2008 |
| EP | 2697422 | 4/2012 |
| EP | 3256560 | 12/2017 |
| EP | 3368600 | 9/2018 |
| GB | 1375197 A | 11/1974 |
| GB | 2317178 | 3/1998 |
| IN | 270891 | 8/2006 |
| JP | 47009016 | 5/1972 |
| JP | 3311745 | 8/1991 |
| JP | 2000-351940 | 12/2000 |
| JP | 2003181299 | 7/2003 |
| JP | 2004091697 | 3/2004 |
| JP | 2004204091 | 7/2004 |
| JP | 2004224861 | 8/2004 |
| JP | 2004231887 | 8/2004 |
| JP | 2004337740 | 12/2004 |
| JP | 2005131072 | 5/2005 |
| JP | 2005138059 | 6/2005 |
| JP | 2005199155 | 7/2005 |
| JP | 2005246639 | 9/2005 |
| JP | 2006136758 | 6/2006 |
| JP | 2006136782 | 6/2006 |
| JP | 3834655 | 10/2006 |
| JP | 2006-526686 | 11/2006 |
| JP | 2006337740 | 12/2006 |
| JP | 2008073588 | 4/2008 |
| JP | 2008188583 | 8/2008 |
| JP | 2008276145 | 11/2008 |
| JP | 2010-111793 | 5/2010 |
| JP | 201126941 | 6/2011 |
| JP | 06287068 | 5/2012 |
| JP | 2013032474 | 2/2013 |
| JP | 5881236 | 3/2016 |
| JP | 2018502975 | 2/2018 |
| JP | 20108502975 | 2/2018 |
| JP | 2004-231887 | 4/2018 |
| KR | 1020060045901 A | 5/2006 |
| KR | 1009866170000 | 10/2010 |
| RU | 2450516 | 10/1994 |
| RU | 2470053 | 12/2012 |
| SU | 346315 | 7/1972 |
| SU | 1130570 | 12/1984 |
| SU | 1567314 | 5/1990 |
| WO | WO 9700134 | 1/1997 |
| WO | WO 2007012026 | 1/2007 |
| WO | WO 2007097284 | 8/2007 |
| WO | WO2011059101 | 5/2011 |
| WO | WO 2011099510 | 8/2011 |
| WO | WO 2012037615 | 3/2012 |
| WO | WO 2012142621 | 10/2012 |
| WO | WO 2013082096 | 6/2013 |
| WO | WO 2013156327 | 10/2013 |
| WO | WO 2014089560 | 6/2014 |
| WO | WO 2016073634 | 5/2016 |

OTHER PUBLICATIONS

IPO; Examination Report dated Dec. 31, 2020 in IN Application No. 202028017215.

USPTO; Advisory Action dated Feb. 22, 2021 in U.S. Appl. No. 16/940,159.

USPTO; Notice of Allowance dated Mar. 10, 2021 in U.S. Appl. No. 16/940,159.

International Searching Authority, International Search Report and Written Opinion dated May 27, 2016 in Application No. PCT/US2016/017599.

USTPO, Restriction Requirement dated Dec. 22, 2016 in U.S. Appl. No. 14/932,840.

USTPO, Office Action dated Mar. 15, 2017 in U.S. Appl. No. 14/932,840.

(56) References Cited

OTHER PUBLICATIONS

USTPO, Office Action dated Apr. 3, 2017 in U.S. Appl. No. 15/432,567.
International Searching Authority, International Preliminary Report on Patentability dated May 9, 2017 in Application No. PCT/US2015/059080.
USTPO, Restriction Requirement dated May 25, 2017 in U.S. Appl. No. 15/041,974.
USTPO, Final Office Action dated Jun. 30, 2017 in U.S. Appl. No. 15/432,567.
USTPO, Final Office Action dated Aug. 9, 2017 in U.S. Appl. No. 14/932,840.
International Searching Authority, International Preliminary Report on Patentability dated Aug. 15, 2017 in Application No. PCT/US2016/017599.
USTPO, Notice of Allowance dated Sep. 8, 2017 in U.S. Appl. No. 15/432,567.
IP Australia, Examination Report dated Sep. 28, 2017 in Australian Application No. 2015343153.
USTPO, Notice of Allowance dated Oct. 24, 2017 in U.S. Appl. No. 14/932,840.
USTPO, Office Action dated Nov. 15, 2017 in U.S. Appl. No. 15/041,974.
USTPO, Notice of Allowance dated Jan. 3, 2018 in U.S. Appl. No. 15/041,974.
Office Action dated Feb. 27, 2018 in Russian Application No. 2017117044.
IP Australia, Examination Report No. 2 dated Mar. 1, 2018 in Australian Application No. 2015343153.
USTPO, Office Action dated Apr. 5, 2018 in U.S. Appl. No. 15/432,428.
USTPO, Office Action dated Apr. 2, 2018 in U.S. Appl. No. 15/432,443.
CIPO, Office Action dated Apr. 12, 2018 in Canadian Application No. 2,972,923.
USTPO, Office Action dated Apr. 16, 2018 in U.S. Appl. No. 15/432,413.
JPO, Office Action dated Apr. 25, 2018 in Japanese Patent Application No. 2017-543303.
KPO, Notice of Preliminary Rejection dated May 4, 2018 in Korean Application No. 10-2017-7014833.
IP Australia, Notice of Acceptance for Patent Application dated May 15, 2018 in Australian Application No. 2015343153.
CIPO, Office Action dated May 29, 2018 in Canadian Application No. 2965978.
IP Australia, Office Action dated May 29, 2018 in Australian Application No. 2016219202.
Office Action dated Jun. 15, 2018 in Russian Application No. 2017124203.
USTPO, Final Office Action dated Jul. 20, 2018 in U.S. Appl. No. 15/432,443.
JPO, Notice of Allowance dated Aug. 22, 2018 in Japanese Application No. 2017-536331.
CIPO, Notice of Allowance dated Aug. 22, 2018 in Canadian Application No. 2965978.
EPO, Exam Report Dated Aug. 30, 2018 in European Application 15857660.3.
USTPO, Final Office Action dated Aug. 31, 2018 in U.S. Appl. No. 15/432,413.
USTPO, Final Office Action dated Aug. 31, 2018 in U.S. Appl. No. 15/432,428.
JPO, Office Action dated Oct. 10, 2018 in Japanese Application No. 2017-543303.
KIPO, Final Office Action dated Oct. 18, 2018 in Korean Application No. 10-2017-7014833.
USTPO, Notice of Allowance dated Oct. 11, 2018 in U.S. Appl. No. 15/432,443.
USTPO, Non-Final Office Action dated Oct. 29, 2018 in U.S. Appl. No. 15/969,576.
USTPO, Advisory Action dated Novembers, 2018 in U.S. Appl. No. 15/432,428.
USTPO, Advisory Action dated Nov. 14, 2018 in U.S. Appl. No. 15/432,413.
KIPO, Notice of Allowance date Nov. 28, 2018 in Korean Application No. 10-2017-7014833.
USTPO, Notice of Allowance dated Nov. 29, 2018 in U.S. Appl. No. 15/432,413.
USTPO, Notice of Allowance dated Dec. 26, 2018 in U.S. Appl. No. 15/432,428.
KIPO, Office Action dated Jan. 7, 2019 in KR Application 10-2018-7037194.
IP Australia, Office Action dated Jan. 31, 2019 in AU Application 2018204875.
JPO, Notice of Allowance date Feb. 4, 2019 in JP Application 2017-543303.
USTPO, Notice of Allowance dated Feb. 7, 2019 in U.S. Appl. No. 15/969,576.
International Searching Authority, International Report on Patentability dated Feb. 8, 2019 in PCT Application PCT/US2018/024654.
USTPO, Non-Final Office Action dated Feb. 11, 2019 in U.S. Appl. No. 15/720,835.
USTPO, Notice of Allowance dated Feb. 19, 2019 in CA Application No. 2972923.
USTPO, Non-Final Office Action dated Feb. 25, 2019 in U.S. Appl. No. 15/718,997.
CIPO, Office Action date Mar. 19, 2019 in CA Application 2,965,978.
EPO, Office Action date Mar. 20, 2019 in EP Application 15 857 660.3.
CNIPA, Non-Final Office Action dated Jun. 11, 2019 in CN Application 201580067821.
USTPO, Notice of Allowance dated Jun. 20, 2019 in U.S. Appl. No. 15/718,997.
Intellectual Property India, Examination Report dated Oct. 18, 2019 in IN Application No. 201727019302.
JPO, Office Action dated Oct. 29, 2019 in JP Application No. 2018-138257.
JPO, Notice of Allowance dated Nov. 12, 2019 in JP Application No. 2018-177318.
CNIPA, Office Action dated Nov. 20, 2019 in CN Application No. 201580067821.
CIPO, Office Action dated Dec. 23, 2020 in CA Application No. 2965978.
EUIPO, Office Action dated Feb. 3, 2020 in EP Application No. 15857660.3.
IDIPO, Office Action dated Jan. 29, 2020 in ID Application No. PID201704268.
IDPO, Examination Report dated Mar. 31, 2020 in ID Application No. PID201703469.
JPO, Notice of Allowance dated Apr. 17, 2020 in JP Application No. 2018-138257.
EPO, Office Action dated Apr. 28, 2020 in EP Application No. 16714595.2.
CNIPA, Office Action dated Jun. 11, 2020 in CN Application No. 201580067821.
DGIP, Office Action dated Jul. 23, 2020 in ID Application No. PID201704268.
IMPI, Office Action dated Aug. 20, 2020 in MX Application No. MX/a/2017/005740.
DGIP, Office Action dated Aug. 24, 2020 in ID Application No. PID201703469.
USTPO, Restriction Requirement dated Aug. 25, 2020 in U.S. Appl. No. 16/591,785.
USTPO, Restriction Requirement dated Aug. 25, 2020 in U.S. Appl. No. 16/940,159.
IMPI, Notice of Allowance dated Sep. 4, 2020 in MX Application No. MX/a/2017/008855.
DGIP, Office Action dated Sep. 23, 2020 in ID Application No. PID201704268.
USTPO, Non-Final Office Action dated Oct. 16, 2020 in U.S. Appl. No. 16/940,159.
DGIP, Notice of Allowance dated Oct. 20, 2020 in ID Application No. PID201703469.

(56) References Cited

OTHER PUBLICATIONS

EPO, Extended Search Report dated Oct. 21, 2020 in EP Application No. 20180203.0.
USTPO, Office Action dated Dec. 1, 2020 in U.S. Appl. No. 16/591,785.
USTPO, Final Office Action dated Dec. 11, 2020 in U.S. Appl. No. 16/940,159.
USTPO, Notice of Allowance dated Feb. 16, 2020 in U.S. Appl. No. 16/591,785.
Characterization of 3-Aminopropyl Oligosilsesquioxane T.P. Knepper, et al. Anal. Chem. 2016, 88, 4894-4902.
"Preparation of Anatase TiO2 Nanorods sol by the Hydrothermal Treatment of Peroxotitanium acid", Li Shuang, et al., Journal of Inorganic Materials, vol. 24, No. 4, pp. 675-679.
CNIPA; Search Report dated Mar. 10, 2021 in CN Application No. 2020103711015.
CNIPA; Office Action dated Mar. 19, 2021 in CN Application No. 2020103711015.
PCT; International Search Report and Written Opinion dated Dec. 31, 2020 in Application No. PCT/US2020/044880.
USPTO; Office Action dated Apr. 16, 2021 in U.S. Appl. No. 17/200,245.
USPTO; Notice of Allowance dated Apr. 30, 2021 in U.S. Appl. No. 17/200,245.
CIPO, Notice of Allowance dated Feb. 19, 2019 in CA Application No. 2972923.
CNIPA, Non-Final Office Action dated Jun. 11, 2019 in CN Application 201680005653.6.
CIPO, Office Action dated Dec. 23, 2019 in CA Application No. 2965978.

* cited by examiner

| Organism | Culture method | Incubation conditions | Further analysis |
|---|---|---|---|
| Total bacteria | Spread plating on R2A medium (BD Diagnostics, Sparks, MD. | 24°C for 5 days | |
| C. difficile | Incubation for 7 days in 0.1% sodium taurocholate and cycloserine-cefoxitin fructose broth | Anaerobic conditions at 37°C for up to 5 days | A 2-mL aliquot was mixed with equal amounts of absolute ethanol. Bacteria were concentrated by centrifugation and pellets were used to inoculate cycloserine-cefoxitin fructose agar. |
| MRSA | Trypticase soy agar amended with 5% sheep's blood, 10 mg/L colistin, and 25 mg/ nalidixic acid using spread plate method | 35°C for 24-48 hours | β-hemolytic colonies were isolated and sub-cultured on trypticase case soy agar with no amendments and incubated at 35°C for 24-48 hours. |
| CRE | Modified Hodge Test; Muller Hinton agar | 35°C for 24 hours | |
| VRE | Bile esculin azide agar | 37°C in $CO_2$ incubator for 24-48 hours | Gram stain, catalase test |

*from an original volume of 4 ml of sponge stick eluate. A 0.1 mL volume of this eluate was used for each assay.

FIG. 5

Average (arithmetic mean) total bacterial numbers (colony forming units) on 100 cm$^2$ from fomites and percent reduction after treatment

| | Baseline* | Weeks after treatment | | | | |
|---|---|---|---|---|---|---|
| | | 1 | 2 | 4 | 8 | 15 |
| Number of Samples | 95 | 81 | 64 | 64 | 64 | 45 |
| Avg number of bacteria | 233,064 | 98 | 80 | 43 | 2,247 | 3,320 |
| Range | 10-7,000,000 | 10-2,500 | 10-840 | 10-2,500 | 10-44,000 | 10-57,000 |
| % reduction | NA | 99.96 | 99.97 | 99.98 | 99.04 | 98.58 |

NA = not applicable.  *=before treatment

FIG. 6

Percent colony forming units of total bacteria per 100 cm² exceeding values indicated

| CFU | Baseline* | Weeks after treatment | | | |
|---|---|---|---|---|---|
| | | 1 | 2 | 4 | 8 | 15 |
| >100 | 71.5 | 11.1 | 17.2 | 12.8 | 51.2 | 33.3 |
| >1,000 | 51.5 | 2.4 | 1.5 | 0 | 17.1 | 24.4 |
| >10,000 | 25.2 | 0 | 0 | 0 | 4.6 | 11.1 |

*=before treatment

FIG. 7

Isolation of antibiotic resistant bacteria (percent of positive sites)

| | Baseline* | Weeks after treatment | | | | |
|---|---|---|---|---|---|---|
| | | 1 | 2 | 4 | 8 | 15 |
| Number of samples | 95 | 81 | 64 | 64 | 64 | 45 |
| VRE | 14 | 0 | 0 | 0 | 1 | 0 |
| MRSA | 7 | 0 | 0 | 0 | 0 | 0 |
| CRE | 3 | 0 | 0 | 0 | 0 | 0 |
| C. difficile | 0 | 0 | 0 | 0 | 0 | 0 |
| Overall Percentage | 25 | 0 | 0 | 0 | 1.5 | 0 |

*=before treatment

FIG. 8

TABLE 9

E. coli testing on Formica Chips

| | 0 Hour | 2 Hour | Log Reduction 2 Hours | 6 Hour | Log Reduction 6 Hours |
|---|---|---|---|---|---|
| REVERSED ORDER OF COATING APPLICATION | 1,000,000 | 41,000 | 1.39 | 140 | 3.85 |
| Control | 1,000,000 | 800,000 | 0.10 | 37,000 | 1.43 |

FIG. 9

TABLE 10

MS-2 testing on Formica Chips

| | 0 Hour | 2 Hour | Log Reduction 2 Hours |
|---|---|---|---|
| REVERSED ORDER OF COATING APPLICATION | 1,000,000 | 16,000 | 3.12 |
| Control | 21,000,000 | 110,000 | 2.28 |

FIG. 10

TABLE 11

MRSA testing on Formica Chips

| | 0 Hour | 2 Hour | Log Reduction 2 Hours | 6 Hour | Log Reduction 6 Hours | 24 Hour | Log Reduction 24 Hours |
|---|---|---|---|---|---|---|---|
| REVERSED ORDER OF COATING APPLICATION | 3,700,000 | 51,000 | 1.86 | 18,000 | 2.31 | 1,200 | 3.49 |
| Control | 3,700,000 | 2,300,000 | 0.21 | 58,000 | 1.80 | 5,800 | 2.80 |

FIG. 11

TABLE 12

E. coli testing on Formica Chips

| | 0 Hour | 2 Hour | Log Reduction 2 Hours | 6 Hour | Log Reduction 6 Hours |
|---|---|---|---|---|---|
| SIMULTANEOUS APPLICATION | 1,000,000 | 42,000 | 1.38 | 110 | 3.96 |
| Control | 1,000,000 | 800,000 | 0.10 | 37,000 | 1.43 |

FIG. 12

TABLE 13

MS-2 testing on Formica Chips

|  | 0 Hour | 2 Hour | Log Reduction 2 Hours |
|---|---|---|---|
| SIMULTANEOUS APPLICATION | 1,000,000 | 42,000 | 2.70 |
| Control | 21,000,000 | 110,000 | 2.28 |

FIG. 13

TABLE 14

MRSA testing on Formica Chips

|  | 0 Hour | 2 Hour | Log Reduction 2 Hours | 6 Hour | Log Reduction 6 Hours | 24 Hour | Log Reduction 24 Hours |
|---|---|---|---|---|---|---|---|
| SIMULTANEOUS APPLICATION | 3,700,000 | 130,000 | 1.45 | 7,000 | 2.72 | 1,400 | 3.42 |
| Control | 3,700,000 | 2,300,000 | 0.21 | 58,000 | 1.80 | 5,800 | 2.80 |

FIG. 14

TABLE 15

| Test Organism | Contact Time | Sample ID | Bacterial Counts (CFU/Carrier) | Mean Bacterial Count (CFU/Carrier) | $Log_{10}$ Reduction | Percent Reduction |
|---|---|---|---|---|---|---|
| E. coli 25922 | Time Zero | Control | 9.80E+06 | 9.21E+06 | N.A. | |
| | | | 8.65E+06 | | | |
| | | (3-Aminopropyl) triethoxysilane | 8.20E+06 | 8.05E+06 | | |
| | | | 7.90E+06 | | | |

FIG. 15

TABLE 16

| Contact Time | Sample ID | Bacterial Counts (CFU/Carrier)[a] | Mean Bacterial Count (CFU/Carrier) | $Log_{10}$ Reduction | Percent Reduction |
|---|---|---|---|---|---|
| 1 Hour | Control | 3.35E+06 | 3.61E+06 | N.A. | N.A. |
| | | 3.90E+06 | | | |
| | (3-Aminopropyl) triethoxysilane | ≤ 5.00E+01 | ≤ 5.00E+01 | ≥ 4.86 | ≥ 99.9986 |
| | | ≤ 5.00E+01 | | | |

E. coli 25922

[a] "≤": No bacterial colonies observed, therefore counts at or below limit of detection (based on 0.1 ml plating volume

FIG. 16

TABLE 17

| Contact Time | Sample ID | Bacterial Counts (CFU/Carrier)[a] | Mean Bacterial Count (CFU/Carrier) | Log$_{10}$ Reduction | Percent Reduction |
|---|---|---|---|---|---|
| E. coli 25922 4 Hours | Control | 2.80E+05 / 5.45E+05 | 3.91E+05 | N.A. | N.A. |
| | (3-Aminopropyl) triethoxysilane | ≤5.00E+01 / ≤5.00E+01 | ≤5.00E+01 | ≥3.89 | ≥99.987 |

[a] "≤": No bacterial colonies observed, therefore counts at or below limit of detection (based on 0.1 ml plating volume)

FIG. 17

TABLE 18

| Test Organism | Contact Time | Sample ID | Bacterial Counts (CFU/Carrier) | Mean Bacterial Count (CFU/Carrier) | Log$_{10}$ Reduction | Percent Reduction |
|---|---|---|---|---|---|---|
| E. coli 25922 | Time Zero | Control | 9.80E+06 / 8.65E+06 | 9.21E+06 | N.A. | N.A. |
| | | (3-Chloropropyl) trimethoxysilane | 1.16E+07 / 8.70E+06 | 1.00E+07 | -0.04 | -8.9% |

FIG. 18

TABLE 19

| Contact Time | Sample ID | Bacterial Counts (CFU/Carrier)[a] | Mean Bacterial Count (CFU/Carrier) | Log₁₀ Reduction | Percent Reduction |
|---|---|---|---|---|---|
| 1 Hour<br><br>E. coli 25922 | Control | 3.95E+06<br>3.90E+06 | 3.61E+06 | N.A. | N.A. |
| | (3-Chloropropyl) trimethoxysilane | 1.10E+03<br>5.00E+01 | 2.35E+02 | 4.19 | 99.994% |

[a] "≤": No bacterial colonies observed, therefore counts at or below limit of detection (based on 0.1 ml plating volume)

FIG. 19

TABLE 20

| Contact Time | Sample ID | Bacterial Counts (CFU/Carrier)[a] | Mean Bacterial Count (CFU/Carrier) | Log₁₀ Reduction | Percent Reduction |
|---|---|---|---|---|---|
| 4 Hours | Control | 2.80E+05 | 3.91E+05 | N.A. | N.A. |
| | | 5.45E+05 | | | |
| | (3-Chloropropyl) trimethoxysilane | ≤5.00E+01 | ≤5.00E+01 | ≥3.89 | ≥99.987 |
| | | ≤5.00E+01 | | | |

*E. coli* 25922

[a] "≤": No bacterial colonies observed, therefore counts at or below limit of detection (based on 0.1 ml plating volume)

FIG. 20

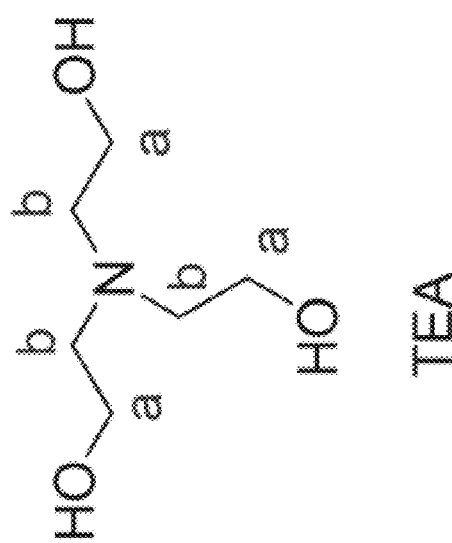
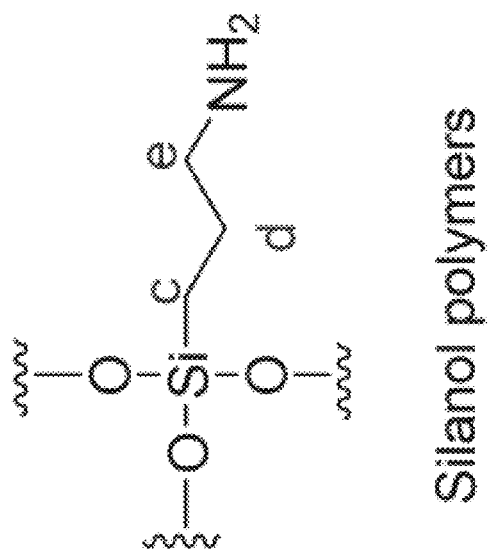
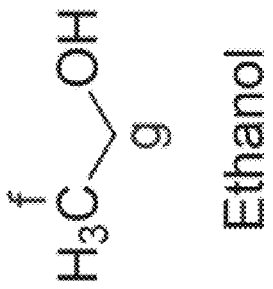
FIG. 30C

| Test Organism | Contact Time | Sample ID | Log₁₀ Reduction | Percent Reduction |
|---|---|---|---|---|
| E. coli 25922 | 0 hour | 2030ₛ | 0.87 | 86.56% |
| | | 2030ₛT | 1.14 | 92.83% |
| | | 2030ₛA01ₛ | 0.61 | 75.28% |
| | | 2030ₛA01ₛT | 0.93 | 88.23% |
| | | 2030ₛA01ₛT - No GK | 1.81 | 98.47% |
| | 1 hour | 2030ₛ | 1.85 | 98.59% |
| | | 2030ₛT | 1.73 | 98.16% |
| | | 2030ₛA01ₛ | ≥ 4.85 | ≥ 99.999% |
| | | 2030ₛA01ₛT | ≥ 4.45 | ≥ 99.996% |
| | | 2030ₛA01ₛT - No GK | ≥ 4.18 | ≥ 99.99% |
| | 4 hour | 2030ₛ | 2.80 | 99.84% |
| | | 2030ₛT | 2.57 | 99.73% |
| | | 2030ₛA01ₛ | ≥ 4.68 | ≥ 99.998% |
| | | 2030ₛA01ₛT | ≥ 4.46 | ≥ 99.997% |
| | | 2030ₛA01ₛT - No GK | ≥ 5.38 | ≥ 99.9996% |

FIG. 37

| Test Organism | Contact Time | Sample ID | Log$_{10}$ Reduction | Percent Reduction |
|---|---|---|---|---|
| S. epidermidis | 0 hour | 2030$_S$ | 0.45 | 64.61% |
| | | 2030$_S$T | 0.71 | 80.71% |
| | | 2030$_S$A01$_S$ | 1.55 | 97.15% |
| | | 2030$_S$A01$_S$T | 1.22 | 93.95% |
| | | 2030$_S$A01$_S$T - No GK | 1.75 | 98.23% |
| | 1 hour | 2030$_S$ | 1.91 | 98.78% |
| | | 2030$_S$T | 1.64 | 97.69% |
| | | 2030$_S$A01$_S$ | 3.40 | 99.96% |
| | | 2030$_S$A01$_S$T | 2.88 | 99.87% |
| | | 2030$_S$A01$_S$T - No GK | 3.20 | 99.94% |
| | 4 hour | 2030$_S$ | 1.91 | 98.76% |
| | | 2030$_S$T | 1.84 | 98.56% |
| | | 2030$_S$A01$_S$ | ≥5.28 | ≥99.9995% |
| | | 2030$_S$A01$_S$T | 3.57 | 99.97% |
| | | 2030$_S$A01$_S$T - No GK | 3.49 | 99.97% |

FIG. 38

| Condition | Coating | Sample ID | Weight of Coating | Mean Weight | Cfu/Carrier | Mean Cfu/mL | Log10 Reduction | Percent Reduction |
|---|---|---|---|---|---|---|---|---|
| E. coli 25922 4 hour | Control | Untreated #1 | 0 | 0.00000 | 3.35E+05 | 3.09E+05 | N/A | N/A |
| | | Untreated #2 | 0 | | 2.85E+05 | | | |
| | ABS-2030;T | Quat/H2O #1 | 0.00015 | 0.00013 | 9.50E+04 | 1.15E+05 | 0.43 | 62.7% |
| | | Quat/H2O #2 | 0.00011 | | 1.40E+05 | | | |
| | | 0 Cycles #1 | 0.00100 | 0.00098 | 1.35E+04 | 1.02E+04 | 1.48 | 96.7% |
| | | 0 Cycles #2 | 0.00096 | | 7.70E+03 | | | |
| | | 10 Cycles #1 | 0.00120 | 0.00103 | 2.90E+03 | 1.13E+04 | 1.44 | 96.3% |
| | | 10 Cycles #2 | 0.00085 | | 4.43E+04 | | | |
| | ABS-2030;A01;T | 0 Cycles #1 | 0.00205 | 0.00200 | ≤1.00E+01 | ≤1.00E+01 | ≥4.49 | 99.997% |
| | | 0 Cycles #2 | 0.00194 | | ≤1.00E+01 | | | |
| | | 10 Cycles #1 | 0.00074 | 0.00074 | 1.70E+05 | 5.97E+04 | 0.71 | 80.7% |
| | | 10 Cycles #2 | 0.00074 | | 2.10E+04 | | | |

"≤": No bacterial colonies observed, therefore counts below the limit of detection

| Test Organism | Contact Time | Condition | | Cfu/Carrier | Mean Cfu/mL | Log$_{10}$ Reduction | Percent Reduction |
|---|---|---|---|---|---|---|---|
| E. coli 25922 | 4 hour | Untreated stainless steel | (A) | 9.00E+05 | 8.87E+05 | 0.00 | 0.00% |
| | | | (B) | 8.75E+05 | | | |
| | | 2030$_5$T Fresh | (A) | 1.00E+01 | 2.45E+01 | 4.56 | 100.00% |
| | | | (B) | 6.00E+01 | | | |
| | | 2030$_5$T Worn | (A) | 8.00E+02 | 2.37E+02 | 3.57 | 99.97% |
| | | | (B) | 7.00E+01 | | | |
| | | 2030:A01$_{0.14}$T Fresh | (A) | 2.00E+01 | 6.48E+01 | 4.14 | 99.99% |
| | | | (B) | 2.10E+02 | | | |
| | | 2030:A01$_{0.14}$T Worn | (A) | 4.37E+02 | 6.27E+02 | 3.15 | 99.93% |
| | | | (B) | 9.00E+02 | | | |

"z" indicates no bacterial colonies observed, therefore counts below the limit of detection.

| Condition | 2030:A01 (molar ratio) | Average percent remaining |
|---|---|---|
| 2030$_5$T | 1:0 | 91.30% |
| 2030:A01$_{0.14}$T | 20:1 | 98.53% |

FIG. 42

Residual Antimicrobial Efficacy Against *E. coli* 25922

| Test Organism | Contact Time | Condition | | Geo. mean (CFU/mL) | Log$_{10}$ Reduction | Percent Reduction |
|---|---|---|---|---|---|---|
| *E. coli* ATCC 25922 | 1 hour | Untreated | | 3.04E+06 | N/A | N/A |
| | | 2030AA01 (5%/0.14%) | Fresh | 1.22E+01 | 5.39 | 99.9995% |
| | | | Rinse | 5.12E+06 | -0.23 | -68.77% |
| | | | Worn | 1.82E+02 | 4.22 | 99.99% |
| | | 2030AA01 (10%/0.28%) | Fresh | 6.40E+01 | 4.68 | 99.998% |
| | | | Rinse | 2.24E+05 | 1.13 | 92.62% |
| | | | Worn | 4.47E+01 | 4.83 | 99.999% |

FIG. 43

| Name of the test carrier | Test Strain | | |
|---|---|---|---|
| | E. coli 25922 | S. epidermidis 12228 | E. aerogenes 13048 |
| Positive control | + | + | + |
| Negative control | o | o | o |
| Neutralization control | + | + | + |
| Slide #1 | o | + | o |
| Slide #2 | o | + | o |
| Slide #3 | o | + | o |
| Slide #4 | o | + | o |
| Slide #5 | o | + | o |
| Slide #6 | o | + | o |
| Slide #7 | o | + | o |
| Slide #8 | o | + | o |
| Slide #9 | o | + | o |
| Slide #10 | o | + | o |

"+" indicates bacteria growth in the 25 mL Letheen Broth while "o" means there is no bacteria growth in the culturing medium.

FIG. 49

| Composition ref. | DMOD content, w/w | TEA content, w/w | CPTMS content w/w | 3-APTES content, w/w | MIC against S. epidermidis 12228 | |
|---|---|---|---|---|---|---|
| | | | | | DMOD mg/mL | APTES mg/mL |
| 2030 #4 | 0.000% | 0.3132% | 0.000% | 9.413% | 0 | 2.9267 |
| 2015-1 | 0.075% | 0.2862% | 0.012% | 8.468% | 0.00073 | 0.0823 |
| 2015-2 | 0.151% | 0.2593% | 0.024% | 7.524% | 0.00146 | 0.0732 |
| 2015-3 | 0.226% | 0.2325% | 0.036% | 6.580% | 0.00220 | 0.0640 |
| 2015-4 | 0.301% | 0.2056% | 0.048% | 5.638% | 0.00293 | 0.0549 |
| 2015-5 | 0.376% | 0.1788% | 0.060% | 4.696% | 0.00366 | 0.0457 |
| 2015-6 | 0.451% | 0.1520% | 0.072% | 3.755% | 0.00439 | 0.0366 |
| 2015-7 | 0.526% | 0.1252% | 0.084% | 2.815% | 0.00512 | 0.0274 |
| 2015-8 | 0.601% | 0.0984% | 0.096% | 1.876% | 0.00293 | 0.0091 |
| 2015-9 | 0.675% | 0.0717% | 0.108% | 0.938% | 0.00659 | 0.0091 |
| 2015 | 0.750% | 0.0450% | 0.120% | 0.000% | 0.00732 | 0 |

FIG. 50

| Composition ref. | DMOD content, w/w | TEA content, w/w | CPTMS content w/w | 3-APTES content, w/w | MIC against E. coli 25922 | |
|---|---|---|---|---|---|---|
| | | | | | DMOD mg/mL | APTES mg/mL |
| 2030 #4 | 0.000% | 0.3132% | 0.000% | 9.413% | 0 | 5.853 |
| 2015-1 | 0.075% | 0.2862% | 0.012% | 8.468% | 0.0469 | 5.268 |
| 2015-2 | 0.151% | 0.2593% | 0.024% | 7.524% | 0.0937 | 4.683 |
| 2015-3 | 0.226% | 0.2325% | 0.036% | 6.580% | 0.0703 | 2.049 |
| 2015-4 | 0.301% | 0.2056% | 0.048% | 5.638% | 0.1874 | 3.512 |
| 2015-5 | 0.376% | 0.1788% | 0.060% | 4.696% | 0.2342 | 2.927 |
| 2015-6 | 0.451% | 0.1520% | 0.072% | 3.755% | 0.2811 | 2.341 |
| 2015-7 | 0.526% | 0.1252% | 0.084% | 2.815% | 0.3279 | 1.756 |
| 2015-8 | 0.601% | 0.0984% | 0.096% | 1.876% | 0.3748 | 1.171 |
| 2015-9 | 0.675% | 0.0717% | 0.108% | 0.938% | 0.8432 | 1.171 |
| 2015 | 0.750% | 0.0450% | 0.120% | 0.000% | 0.9369 | 0.0000 |

FIG. 51

| Coating Ref. | S. epidermidis 12228 | | E. coli 25922 | |
| --- | --- | --- | --- | --- |
| | Log₁₀ reduction | Percent reduction | Log₁₀ reduction | Percent reduction |
| 2030 #4 | 5.37 | 99.9996% | 4.92 | 99.9988% |
| 2015-1 | 5.37 | 99.9996% | 4.92 | 99.9988% |
| 2015-2 | 5.37 | 99.9996% | 4.92 | 99.9988% |
| 2015-3 | 5.37 | 99.9996% | 4.92 | 99.9988% |
| 2015-4 | 5.37 | 99.9996% | 4.92 | 99.9988% |
| 2015-5 | 5.37 | 99.9996% | 4.92 | 99.9988% |
| 2015-6 | 3.39 | 99.9595% | 4.92 | 99.9988% |
| 2015-7 | 5.37 | 99.9996% | 4.92 | 99.9988% |
| 2015-8 | 5.37 | 99.9996% | 4.92 | 99.9988% |
| 2015-9 | 2.42 | 99.6211% | 3.28 | 99.9474% |

FIG. 52

| Composition ref. | Organosilane content v/v | TEA content, v/v | MIC (mg/ml) against S. epidermidis 12228 |
|---|---|---|---|
| 2030₁₀ | 10.00% | 0.00% | 2.93 |
| 2030 Composition #4 | 10.00% | 0.28% | 2.93 |
| #0590 | 10.00% | 0.00% | 0.74 |
| #8398 | 10.00% | 0.00% | 0.02 |
| #0592 | 10.00% | 0.00% | 0.74 |

FIG. 53

| Composition ref. | Organosilane content v/v | TEA content, v/v | MIC (mg/ml) against E.coli 25922 |
|---|---|---|---|
| 2030$_{10}$ | 10.00% | 0.00% | 5.85 |
| 2030 formulation #4 | 10.00% | 0.28% | 5.85 |
| #0590 | 10.00% | 0.00% | 5.94 |
| #8398 | 10.00% | 0.00% | 3.06 |
| #0592 | 10.00% | 0.00% | 2.97 |

FIG. 54

| Coating Ref. | S. epidermidis 12228 | | E. coli 25922 | |
| --- | --- | --- | --- | --- |
| | $Log_{10}$ reduction | Percent reduction | $Log_{10}$ reduction | Percent reduction |
| $2030_{10}$ | 5.37 | 99.9996% | 4.92 | 99.9988% |
| 2030 #4 | 5.37 | 99.9996% | 4.92 | 99.9988% |
| #5090 | 3.20 | 99.9375% | 4.92 | 99.9988% |
| #8398 | 4.53 | 99.9970% | 4.92 | 99.9988% |
| #0592 | 3.35 | 99.9557% | 4.92 | 99.9988% |

FIG. 55

ANTIMICROBIAL COATINGS COMPRISING ORGANOSILANE HOMOPOLYMERS

CROSS-REFERENCE TO RELATED APPLICATIONS

This application is a continuation of U.S. application Ser. No. 16/591,785, filed Oct. 3, 2019 entitled "ANTIMICROBIAL COATINGS COMPRISING ORGANOSILANE HOMOPOLYMERS." The '785 application is a continuation-in-part of, claims priority to and the benefit of, U.S. application Ser. No. 15/718,997, filed Sep. 28, 2017 entitled "ANTIMICROBIAL COATINGS CAPABLE OF REDUCING THE NUMBER OF MURINE NOROVIRUS INOCULATED THEREON" (now U.S. Pat. No. 10,463,046). The '997 application is a divisional of U.S. application Ser. No. 15/041,974, filed Feb. 11, 2016 entitled "ANTI-MICROBIAL COATING AND METHOD TO FORM SAME" (now U.S. Pat. No. 9,918,475). The '974 application claims priority to U.S. Provisional Patent Application Ser. No. 62/114,998, filed Feb. 11, 2015 entitled "ANTI-MICROBIAL COATING AND METHOD TO FORM SAME." The '974 application is a continuation-in-part of U.S. application Ser. No. 14/932,840, filed Nov. 4, 2015 entitled "COMPOSITION AND METHOD TO FORM A SELF DECONTAMINATING SURFACE" (now U.S. Pat. No. 9,856,360). The '840 application claims priority to U.S. Provisional Patent Application Ser. No. 62/075,020, filed Nov. 4, 2014 entitled "COMPOSITION AND METHOD TO FORM A SELF DECONTAMINATING SURFACE." All of these disclosures are incorporated herein by reference in their entireties for all purposes.

FIELD

The present disclosure generally relates to antimicrobial coatings, and more specifically, to durable antimicrobial coatings comprising silane homopolymers.

BACKGROUND

In a publication entitled "Evaluation of Two Organosilane Products for Sustained Antimicrobial Activity on High-Touch Surfaces in Patient Rooms, American Journal of Infection Control 42 (2014) 326-8, reports, inter alia, "To the best of our knowledge, ours is the first published controlled trial of applying organosilane compounds to high-touch surfaces in patient rooms as a strategy for reducing the level of microbial contamination of environmental surfaces between daily cleanings." Id. at 327.

The authors found the two organosilanes ineffective for any sort of sustained antimicrobial efficacy. "In conclusion, our study was not able to demonstrate sustained antimicrobial activity for either organosilane product tested when applied to high-touch surfaces." Id. at 328.

SUMMARY

In various embodiments, aqueous antimicrobial coating compositions are described. The compositions generally comprise at least one organosilane homopolymer, present as a distribution of chain lengths, and, optionally, at least one amine. The compositions can be disposed on inanimate surfaces and dried into thin films capable of killing microorganisms that contact the film.

In various embodiments, aqueous antimicrobial coating compositions are disclosed that exhibit germicidal spray efficacy against various microorganisms. The aqueous antimicrobial coating compositions capable of germicidal spray efficacy generally comprise at least one organosilane homopolymer, present as a distribution of chain lengths, and, optionally, at least one amine. In various examples, the aqueous antimicrobial coating compositions not only function to kill surface borne organisms as a germicidal spray, the aqueous antimicrobial coating compositions may then dry on the surface into a thin film capable of killing microorganisms that contact the film.

In various embodiments, a method of forming an antimicrobial coating on a surface is described. The method generally comprises coating a portion of a surface with an aqueous antimicrobial coating composition comprising at least one organosilane homopolymer present in a distribution of chain lengths, and, optionally, at least one amine.

In various embodiments, a method of forming an antimicrobial coating on a surface is described. The method generally comprises: (1) disposing on the surface an aqueous antimicrobial coating composition comprising at least one organosilane homopolymer present as a distribution of chain lengths, and, optionally, at least one amine, and (2) disposing on the surface an aqueous composition comprising a titanyl sol-gel. The two compositions may be applied to the surface in either order, or applied simultaneously to the surface such as from two spray nozzles directed to the same portion of the surface.

In various embodiments, an aqueous antimicrobial coating composition comprises:

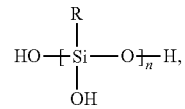

wherein:
n≥2; and
R=
—(CH$_2$)$_m$—X, wherein m=1 to 6, X=NH$_2$, Cl, Br, or I;
—(CH$_2$)$_3$—NH—(CH$_2$)$_2$—NH$_2$;
—(CH$_2$)$_3$—NH—(CH$_2$)$_2$—NH—(CH$_2$)$_2$—NH$_2$;
—(CH$_2$)—NH—(CH$_2$)$_6$—NH$_2$;
—(CH$_2$)$_3$—NH—(CH$_2$)$_3$—Si(OR$^{12}$)$_3$, wherein R$^{12}$=H, —CH$_3$ or —CH$_2$CH$_3$; or
—(CH$_2$)$_3$—NH—(CH$_2$)$_2$—NH—(CH$_2$)$_3$—Si(OR$^{12}$)$_3$, wherein R$^{12}$=H, —CH$_3$ or —CH$_2$CH$_3$.

In various embodiments, the organosilane homopolymers are present in the aqueous antimicrobial coating in total at from about 0.01 wt. % to about 15 wt. %, based on the total weight of the composition.

In various embodiments, the aqueous antimicrobial coating composition further comprises from about 0.01 wt. % to about 5.0 wt. % of at least one amine, based on the total weight of the composition, wherein the at least one amine has the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12.

In various embodiments, the at least one amine comprises triethanolamine, present in the aqueous antimicrobial coating composition at from about 0.01 wt. % to about 1.0 wt. %, based on the total weight of the composition.

In various embodiments, an aqueous antimicrobial coating composition consists of 9.41 wt. % 3-aminopropylsilanetriol homopolymer having a chain length distribution of n=3 to about 30, 0.31 wt. % triethanolamine, and 90.28 wt. % water.

In various embodiments, the aqueous antimicrobial coating composition includes 3-aminopropylsilanetriol homopolymer, having a chain length distribution of n=2 to about 30, as the only organosilane homopolymer present in the aqueous antimicrobial coating composition.

In various embodiments, the aqueous antimicrobial coating composition may further comprise 3-(trihydroxysilyl) propyl dimethyloctadecyl ammonium chloride homopolymer having a chain length distribution of n≥2.

In various embodiments, the aqueous antimicrobial coating composition includes 3-aminopropylsilanetriol homopolymer, having a chain length distribution of n=2 to about 30; 3-chloropropylsilanetriol homopolymer, having a chain length distribution of n≥2; and 3-(trihydroxysilyl)propyl dimethyloctadecyl ammonium chloride homopolymer having a chain length distribution of n≥2 as the only organosilane homopolymers present in the aqueous antimicrobial coating composition. In various embodiments, the aqueous antimicrobial coating composition further comprises at least one amine. In certain embodiments, the at least one amine consists of triethanolamine, present at from about 0.01 wt. % to about 5.0 wt. %.

In various embodiments, the only organosilane homopolymer present in the aqueous antimicrobial coating composition has the structure:

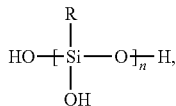

wherein n≥2; and R=—(CH$_2$)$_3$—NH—(CH$_2$)$_2$—NH$_2$.

In various embodiments, the only organosilane homopolymer present in the aqueous antimicrobial coating composition has the structure:

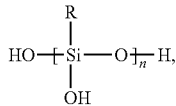

wherein n≥2; and R=—(CH$_2$)$_3$—NH—(CH$_2$)$_2$—NH—(CH$_2$)$_2$—NH$_2$.

In various embodiments, the only organosilane homopolymer present in the aqueous antimicrobial coating composition has the structure:

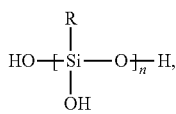

wherein n≥2; and R=—(CH$_2$)—NH—(CH$_2$)$_6$—NH$_2$.

In various embodiments, the only organosilane homopolymer present in the aqueous antimicrobial coating composition has the structure:

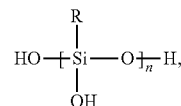

wherein n≥2; and R=—(CH$_2$)$_3$—NH—(CH$_2$)$_3$—Si(OR$^{12}$)$_3$, wherein R$^{12}$=H, —CH$_3$ or —CH$_2$CH$_3$.

In various embodiments, the only organosilane homopolymer present in the aqueous antimicrobial coating composition has the structure:

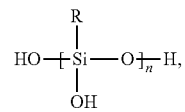

wherein n≥2; and R=—(CH$_2$)$_3$—NH—(CH$_2$)$_2$—NH—(CH$_2$)$_3$—Si(OR$^{12}$)$_3$, wherein R$^{12}$=H, —CH$_3$ or —CH$_2$CH$_3$.

In various embodiments, use of an aqueous antimicrobial composition comprising at least one organosilane homopolymer in the preparation of an antimicrobial coating on a surface comprises disposing the aqueous antimicrobial composition on the surface and allowing the aqueous antimicrobial composition thus disposed on the surface to dry, wherein the antimicrobial coating exhibits residual self-sanitizing efficacy.

In various embodiments, a method of preparing an antimicrobial coating on a surface comprises: (a) disposing on the surface an aqueous antimicrobial coating composition comprising a total of from about 0.01 wt. % to about 15 wt. % of at least one organosilane homopolymer having the polymeric structure:

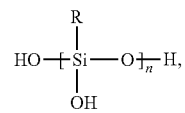

wherein:
n≥2; and
R=
—(CH$_2$)$_m$—X, wherein m=1 to 6, X=NH$_2$, Cl, Br, or I;
—(CH$_2$)$_3$—NH—(CH$_2$)$_2$—NH$_2$;
—(CH$_2$)$_3$—NH—(CH$_2$)$_2$—NH—(CH$_2$)$_2$—NH$_2$;
—(CH$_2$)—NH—(CH$_2$)$_6$—NH$_2$;
—(CH$_2$)$_3$—NH—(CH$_2$)$_3$—Si(OR$^{12}$)$_3$, wherein R$^{12}$=H, —CH$_3$ or —CH$_2$CH$_3$; or
—(CH$_2$)$_3$—NH—(CH$_2$)$_2$—NH—(CH$_2$)$_3$—Si(OR$^{12}$)$_3$, wherein R$^{12}$=H, —CH$_3$ or —CH$_2$CH$_3$; and
(b) allowing the aqueous antimicrobial coating composition thus disposed on the surface to dry.

In various embodiments of the method, the aqueous antimicrobial coating composition further comprises from about 0.01 wt. % to about 5.0 wt. % of at least one amine, based on the total weight of the aqueous antimicrobial coating composition, wherein the at least one amine has the structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12.

In various embodiments of the method, the at least one amine comprises triethanolamine, present in the aqueous antimicrobial coating composition at from about 0.01 wt. % to about 1.0 wt. %, based on the total weight of the aqueous antimicrobial coating composition.

In various embodiments of the method, the aqueous antimicrobial coating composition consists of 9.41 wt. % 3-aminopropylsilanetriol homopolymer having a chain length distribution of n=3 to about 30, 0.31 wt. % triethanolamine, and 90.28 wt. % water.

In various embodiments of the method, the aqueous antimicrobial coating composition further comprises 3-(trihydroxysilyl)propyl dimethyloctadecyl ammonium chloride homopolymer having a chain length distribution of n≥2.

In various embodiments of the method, the only organosilane homopolymers present in the aqueous antimicrobial coating composition are 3-aminopropylsilanetriol homopolymer, having a chain length distribution of n=2 to about 30; 3-chloropropylsilanetriol homopolymer, having a chain length distribution of n≥2; and 3-(trihydroxysilyl)propyl dimethyloctadecyl ammonium chloride homopolymer having a chain length distribution of n≥2. In various embodiments, the aqueous antimicrobial coating composition further comprises at least one amine. In certain embodiments, the at least one amine consists of triethanolamine, present at from about 0.01 wt. % to about 5.0 wt. %.

In various embodiments of the method, the only organosilane homopolymer present in the aqueous antimicrobial coating composition has the structure:

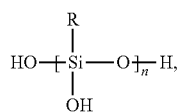

wherein n≥2; and R=—(CH$_2$)$_3$—NH—(CH$_2$)$_2$—NH$_2$.

In various embodiments of the method, the only organosilane homopolymer present in the aqueous antimicrobial coating composition has the structure

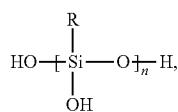

wherein n≥2; and R=—(CH$_2$)$_3$—NH—(CH$_2$)$_2$—NH—(CH$_2$)$_2$—NH$_2$.

In various embodiments of the method, the only organosilane homopolymer present in the aqueous antimicrobial coating composition has the structure

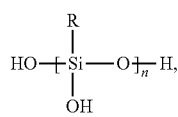

wherein n≥2; and R=—(CH$_2$)—NH—(CH$_2$)$_6$—NH$_2$.

In various embodiments of the method, the only organosilane homopolymer present in the aqueous antimicrobial coating composition has the structure

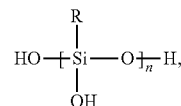

wherein n≥2; and R=—(CH$_2$)$_3$—NH—(CH$_2$)$_3$—Si(OR$^{12}$)$_3$, wherein R$^{12}$=H, —CH$_3$ or —CH$_2$CH$_3$.

In various embodiments of the method, the only organosilane homopolymer present in the aqueous antimicrobial coating composition has the structure

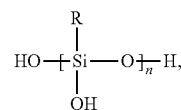

wherein n≥2; and R=—(CH$_2$)$_3$—NH—(CH$_2$)$_2$—NH—(CH$_2$)$_3$—Si(OR$^{12}$)$_3$, wherein R$^{12}$=H, —CH$_3$ or —CH$_2$CH$_3$.

In various embodiments, the method may further comprise the steps of disposing a titanyl sol-gel on the surface overtop of the dried aqueous antimicrobial coating composition; and allowing the titanyl sol-gel to dry.

In various embodiments, the titanyl sol-gel comprises an aqueous mixture of peroxotitanium acid and peroxo-modified anatase sol. In various embodiments, the titanyl sol-gel comprises an aqueous mixture of peroxotitanium acid and peroxo-modified anatase sol. In certain aspects, the titanyl sol-gel comprises 0.85 wt. % peroxotitanium acid and peroxo-modified anatase sol mixture, with the remainder of the sol-gel being water.

In various embodiments, the addition of triethanolamine to a composition of 3-aminopropylsilanetriol homopolymer improves the antimicrobial efficacy of the resulting coating compared to a coating of 3-aminopropylsilanetriol homopolymer, and consequently, extends the antimicrobial efficacy of the coating.

In various embodiments, the addition of triethanolamine to a composition of 3-aminopropylsilanetriol homopolymer improves the durability of the resulting coating compared to a coating of 3-aminopropylsilanetriol homopolymer, and consequently, extends the antimicrobial efficacy of the coating.

In various embodiments, the addition of triethanolamine to an aqueous composition of 3-aminopropylsilanetriol homopolymer doesn't change the storage stability of the aqueous 3-aminopropylsilanetriol homopolymer.

In various embodiments, the addition of triethanolamine to an aqueous composition of 3-aminopropylsilanetriol homopolymer alters the chain length distribution with loss of 3-aminopropylsilanetriol dimer.

BRIEF DESCRIPTION OF THE DRAWINGS

The disclosure will be better understood from a reading of the following detailed description taken in conjunction with the drawings in which like reference designators are used to designate like elements, and in which:

FIG. 5 sets for the test methods used for each of the organisms *Clostridium difficile* methicillin-resistant *Staphylococcus aureus* (MRSA), vancomycin-resistant *Enterococcus* (VRE), and carbapenem-resistant Enterobacteriaceae (CRE), in accordance with various embodiments;

FIG. 6 sets forth the average number of total bacteria detected per 100 $cm^2$ at all locations and percent reductions in total bacterial numbers after treatment, in accordance with various embodiments;

FIG. 7 shows the reduction in bacteria at 1, 2, 4, 8, and 15 weeks after treatment, as compared to before treatment, in accordance with various embodiments;

FIG. 8 shows the percent of samples in which antibiotic resistant bacteria were isolated at the different sites sampled, in accordance with various embodiments;

FIG. 9 shows efficacy data for the treated coupons after inoculation with *E. coli*, in accordance with various embodiments;

FIG. 10 shows efficacy data for the treated coupons after inoculation with MS-2, in accordance with various embodiments;

FIG. 11 shows efficacy data for the treated coupons after inoculation with MRSA, in accordance with various embodiments:

FIG. 12 shows efficacy data for the treated coupons after inoculation with *E. coli*, in accordance with various embodiments;

FIG. 13 shows efficacy data for the treated coupons after inoculation with MS-2, in accordance with various embodiments;

FIG. 14 shows efficacy data for the treated coupons after inoculation with MRSA, in accordance with various embodiments;

FIG. 15 shows efficacy data for coupons treated with 3-aminopropyltrimethoxy silane and triethanolamine mixture and Titanium Oxide Moieties after inoculation with *E. coli*, in accordance with various embodiments;

FIG. 16 shows efficacy data for coupons treated with 3-aminopropyltrimethoxy silane and triethanolamine mixture and Titanium Oxide Moieties after inoculation with *E. coli*, in accordance with various embodiments;

FIG. 17 shows efficacy data for coupons treated with 3-aminopropyltrimethoxy silane and triethanolamine mixture and Titanium Oxide Moieties after inoculation with *E. coli*, in accordance with various embodiments;

FIG. 18 shows efficacy data for coupons treated with 3-chloropropyltrimethoxy silane and triethanolamine mixture and Titanium Oxide Moieties after inoculation with *E. coli*, in accordance with various embodiments;

FIG. 19 shows efficacy data for coupons treated with 3-chloropropyltrimethoxy silane and triethanolamine mixture and Titanium Oxide Moieties after inoculation with *E. coli*, in accordance with various embodiments;

FIG. 20 shows efficacy data for coupons treated with 3-chloropropyltrimethoxy silane and triethanolamine mixture and Titanium Oxide Moieties after inoculation with *E. coli*, in accordance with various embodiments;

FIGS. 30A, 30B and 30C show a $^{13}$C-NMR spectrum of a solution of 3-aminopropylsilanetriol homopolymer along with a magnified portion of the spectrum and possible peak assignments based on carbon atom proximities and local bonding;

FIG. 37 sets forth surface time-kill studies against *E. coli* 25922 for various coatings comprising 3-aminopropylsilanetriol homopolymer;

FIG. 38 sets forth surface time-kill studies against *S. epidermidis* 12228 for various coatings comprising 3-aminopropylsilanetriol homopolymer;

FIG. 39 sets forth surface time-kill studies against *E. coli* 25922 for various coatings comprising 3-aminopropylsilanetriol homopolymer with and without mechanical abrasion of the coating;

FIGS. 40 and 41 set forth norovirus surface persistence data for coatings comprising 3-aminopropylsilanetriol homopolymer;

FIG. 42 sets forth surface time-kill studies against *E. coli* 25922 for various coatings comprising 3-aminopropylsilanetriol homopolymer and titanium sol, with and without mechanical abrasion of the coating;

FIGS. 43 and 44 set forth surface time-kill studies against *E. coli* 25922 for various coatings comprising 3-aminopropylsilanetriol homopolymer with and without rinsing and mechanical abrasion of the coating;

FIG. 49 sets forth results from a germicidal spray test of 3-aminopropylsilanetriol homopolymer solutions;

FIG. 50 sets forth minimum inhibitory concentration (MIC) against *S. epidermidis* 12228 for various compositions comprising a mixture of 3-aminopropylsilanetriol homopolymer, 3-(trihydroxysilyl)propyl dimethyloctadecyl ammonium chloride homopolymer, and 3-chloropropylsilanetriol homopolymer;

FIG. 51 sets forth minimum inhibitory concentration (MIC) against *E. coli* 25922 for various compositions comprising a mixture of 3-aminopropylsilanetriol homopolymer, 3-(trihydroxysilyl)propyl dimethyloctadecyl ammonium chloride homopolymer, and 3-chloropropylsilanetriol homopolymer;

FIG. 52 sets forth surface time-kill studies against *E. coli* 25922 and *S. epidermidis* 12228 for various coatings comprising a mixture of 3-aminopropylsilanetriol homopolymer, 3-(trihydroxysilyl)propyl dimethyloctadecyl ammonium chloride homopolymer, and 3-chloropropylsilanetriol homopolymer;

FIG. 53 sets forth minimum inhibitory concentration (MIC) against *S. epidermidis* 12228 for various compositions comprising organosilane homopolymer, wherein the polymer has additional amine functionality;

FIG. 54 sets forth minimum inhibitory concentration (MIC) against *E. coli* 25922 for various compositions comprising organosilane homopolymer, wherein the homopolymer has additional amine functionality; and FIG. 55 sets forth surface time-kill studies against *E. coli* 25922 and *S. epidermidis* 12228 for various coatings comprising organosilane homopolymer, wherein the homopolymer has additional amine functionality.

DETAILED DESCRIPTION

Definitions

Figure 1:
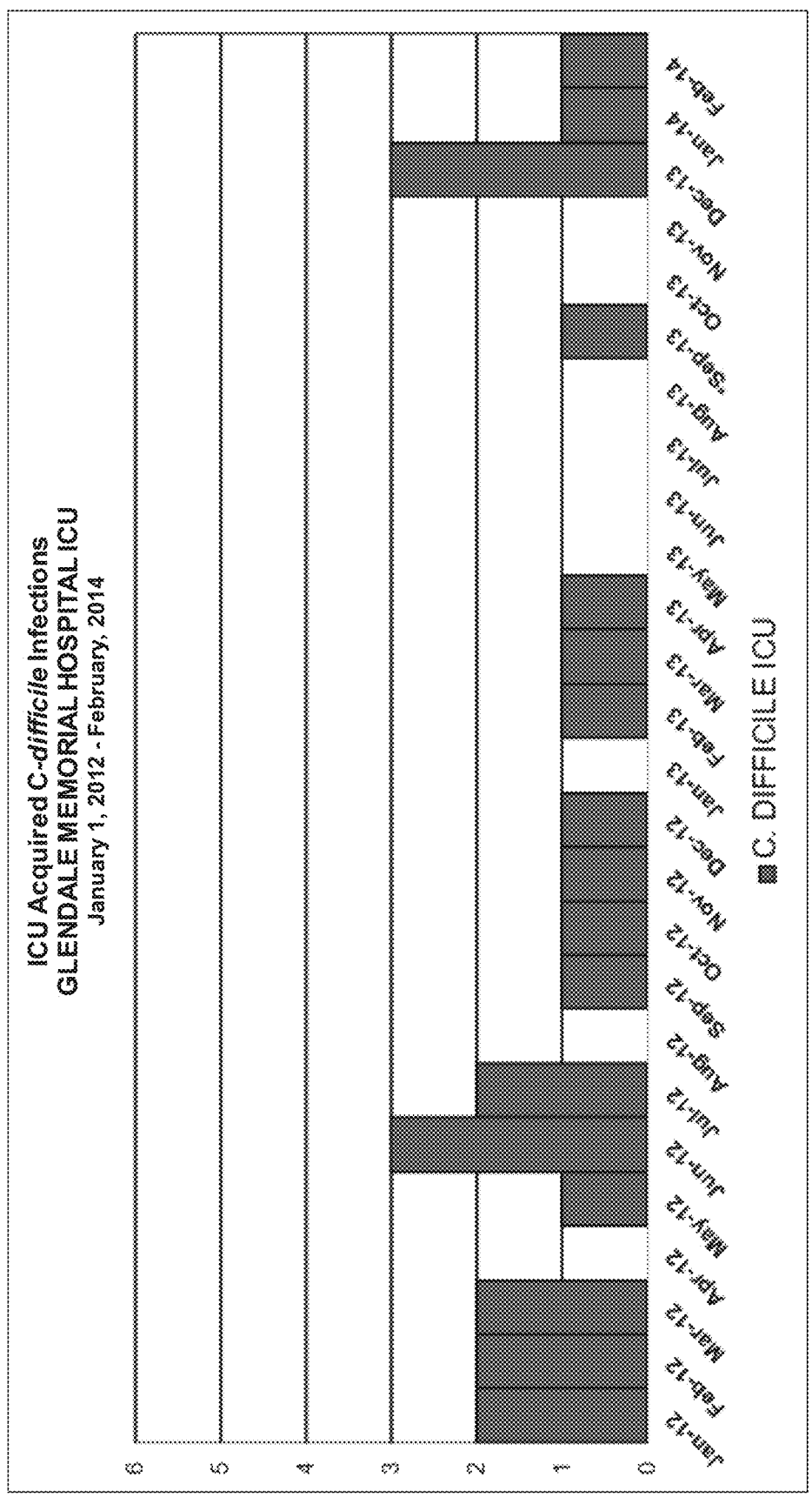
FIG. 1 graphically shows the number of hospital acquired *C-difficile* infections in the Glendale Memorial Hospital ICU from January 2012 through February 2014, in accordance with various embodiments.

As used herein, the term "antimicrobial" is used generally to indicate at least some level of microbe kill by a composition or a coating on a portion of a surface. For example, antimicrobial may be used to indicate a biostatic efficacy, sanitizing level (3-log, or 99.9%) reduction in at least one organism, or a disinfection level (5-log, or 99.999%) reduction in at least one organism, or sterilization (no detectable organisms). Microbes, or microorganisms, may include any species of bacteria, virus, mold, yeast, or spore. Thus, antimicrobial herein encompasses antiviral and antibacterial.

As used herein, the terms "residual antimicrobial," "residual self-sanitizing," and "self-decontaminating surface" are used interchangeably to indicate a surface that maintains antimicrobial efficacy over a certain period of time under certain conditions once the surface is coated with an antimicrobial coating composition and that composition dried on the surface as a thin film. A coated surface may maintain residual antimicrobial efficacy indefinitely, or the coating may eventually "wear out" and lose its residual antimicrobial efficacy. An antimicrobial coating composition may function as a contact sanitizer, bacteriostatic material, disinfectant, or sterilant, (e.g. as a liquid antimicrobial applied to a contaminated surface) and may also have the ability to leave behind a residual antimicrobial coating on the surface once dried or cured thereon that can keep inactivating new microorganisms that contact the coated surface. In various embodiments, coating compositions may not be antimicrobial until dried or cured on a surface, but are still referred to as antimicrobial coating compositions because of their ability to produce a residual antimicrobial coating on a surface. Antimicrobial coating compositions for use in various embodiments may provide a residual antimicrobial efficacy to a surface, meaning that a microorganism later inoculated on, or that otherwise comes in contact with, the coated surface may experience cell death, destruction, or inactivation. The residual antimicrobial effect made possible by the coatings herein is not limited by a particular mechanism of action, and no such theories are proffered. For example, an antimicrobial effect measured on a surface may be the result of intracellular mutations, inhibition of certain cellular processes, rupture of a cell wall, or a nondescript inactivation of the organism, such as in the case of viruses. Other antimicrobial effects may include inhibiting the reproduction of an organism, or inhibiting the organism's ability to accumulate into biofilms.

As used herein, the term "antimicrobial coating composition" refers to a chemical composition comprising at least one chemical species, which is used to produce a residual antimicrobial coating on a surface after the composition is applied and then either dried, allowed to dry, or cured in some manner. The term is also used for liquid compositions that may find use as a germicidal spray (disinfectant or sanitizer), since the composition could then go on to dry into an antimicrobial coating. The term is also extended to include a composition that may be applied sequentially (e.g. over or under) or contemporaneously with the application of an antimicrobial coating composition, such as to assist in bonding the residual antimicrobial coating to the surface, improve durability of the overall coating, and/or to provide a catalytic effect or some sort of potentiation or synergy with the residual antimicrobial coating comprising an antimicrobial active. For simplicity herein, each one of multiple compositions used sequentially or contemporaneously to produce an overall residual antimicrobial coating on a portion of a surface is referred to as an "antimicrobial coating composition," even if one or more of the compositions used for coating has no identifiable antimicrobial active or where the active agent is uncertain. An antimicrobial coating composition may comprise a neat, 100% active chemical species or may be a solution or suspension of a single chemical species in a solvent. In other aspects, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize, such as to produce homopolymer distributions while in solution, prior to a coating process using that composition. In other embodiments, chemical constituents within an antimicrobial coating composition may chemically react on the surface that the composition is applied to, such as while the composition is drying and concentrating on the surface or while the coating composition is cured by various methods. In various embodiments, a solution comprising a homopolymer distribution may polymerize further, such as to longer chain lengths, while the solution dries on a surface. Antimicrobial coating compositions for use in various embodiments may further comprise any number and combination of inert excipients, such as for example, solvents, buffers, acids, alkali, surfactants, emulsifiers, stabilizers, thickeners, free-radical initiators, catalysts, etc.

As used herein, the term "homopolymer" takes on its ordinary meaning in organic chemistry of a molecule having repeated and identical monomer units. For simplicity sake, the term homopolymer herein includes each of the smaller oligomers, i.e., dimer, trimer, tetramer, etc., unless specified otherwise. For example, a homopolymer distribution herein may include the dimer and above, or the trimer and above, as indicated. In some instances, a homopolymer chain length distribution may be well defined and characterized, and in other instances, the distribution may not be characterizable at all and may remain unknown.

As used herein, the term "wt. %" takes on the ordinary meaning of percent (%) by weight of an ingredient in a chemical composition, based on the total weight of the composition "as made." For example, an aqueous composition comprising 1 wt. % amine "based on the total weight of the composition" equates to a composition containing 99.0 grams water and 1.0 gram amine. Wt. % in a composition indicates the wt. % of active material, unless indicated otherwise. "As made" means that a written composition shows what was added to a mixing vessel, and not what might end up in the mixture after certain ingredients react, such as if an ingredient hydrolyzes or polymerizes.

As used herein, the trademarked product Formica® is understood to be a paper and melamine laminate hard surface. This product is well-known to the general public, recognized as being a thin laminate sheeting typically glued down onto plywood, particle board or other base material in the construction of countertops. In various embodiments, the antimicrobial compositions herein are coated onto Formica® and other hard surfaces. The surfaces coated with the antimicrobial coating compositions herein may be those frequently touched surfaces typically found in a hospital or other healthcare setting, namely Formica® and stainless steel. Being frequently touched, these surfaces may participate in germ transfer and hospital acquired infections.

As used herein, the term "titanium (IV) species" refers to any chemical compound comprising at least one tetravalent titanium atom, regardless if monomeric, dimeric, trimeric, or polymeric. Non-limiting examples include titanium (IV) oxide ($TiO_2$) in any form, other Ti(IV) species, (e.g., $TiCl_4$, Ti—(O-i-$C_3H_7$)$_4$ or any other Ti(IV) alkoxide, phenoxide or halide). Various forms of $TiO_2$ for use herein include, but are not limited to, rutile, anatase, brookite, hollandite-like, ramsdellite-like, $\alpha$-$PbO_2$-like, baddeleyite-like form, orthorhombic $TiO_2$—OI, cubic, and/or cotunnite-like forms. The most common crystalline forms are anatase, brookite and rutile. In various examples, Ti(IV) species for use herein comprise Ti nanoparticles. Further, Ti(IV) species for use herein include "titanyl-oxide moieties," which is a broad term defined herein to include any and all Ti compounds and mixtures known to form $TiO_2$ thin films, or at least suspected as able to form $TiO_2$ thin films, such as via the sol-gel process. A titanyl sol-gel is a precursor in the preparation of $TiO_2$ thin films. For example, a mixture of Ti($OC_4H_9$)$_4$, ethanol, water, and diethanolamine, in a 1:26.5:1:1 molar ratio, has been disclosed as forming a $TiO_2$ film (see J. Yu, et al., *Materials Chemistry and Physics*, vol. 69, pp 25-29 (2001)). This reference further discloses that whether or not the film is photocatalytic depends, inter alia, on the curing conditions for the sol-gel after surface application, e.g. using high temperatures. In another non-limiting example, a sol-gel route to mesoporous and nanocrystalline anatase thin layers begins with acidic hydrolysis of titanium isopropoxide, (see F. Bosc, *Chem. Mater.*, 15(12), pp 2463-2468, (2003)).

In certain examples, titanyl-oxide moieties for use herein comprise a colloidal suspension of from about 0.5 wt. % to about 50 wt. % $TiO_2$ in water. In other examples, titanyl-oxide moieties comprise an aqueous mixture of Ti—(O-i-$C_3H_7$)$_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—(O-i-$C_3H_7$)$_4$ or $TiCl_4$. A $TiO_2$ sol-gel composition, when coated onto a portion of a surface, provides a thin film $TiO_2$ coating on the portion of the surface.

In various embodiments, titanyl-oxide moieties comprise Ti($OR^3$)$_4$, wherein $R^3$ is alkyl, substituted alkyl, aryl, or substituted aryl, and wherein the four separate $R^3$ groups are identical or different. Examples of Ti($OR^3$)$_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—(O-i-$C_3H_7$)$_4$) or dissolved in an alcohol or other organic solvent (s), such as the corresponding alcohol, where feasible, (methanol, ethanol, i-propanol, etc.). Thus, titanyl-oxide moieties may in some instances comprise a solution of Ti—(O-i-$C_3H_7$)$_4$ in isopropanol or some other alcohol.

In various embodiments, titanyl-oxide moieties comprise Ti($OR^3$)$_4$, wherein $R^3$ is alkyl, substituted alkyl, aryl, or substituted aryl. In certain aspects, titanyl-oxide moieties may further comprise a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, titanyl-oxide moieties consist essentially of Ti—(O-i-$C_3H_7$)$_4$. Other examples include Ti—(O-i-$C_3H_7$)$_4$ and an alcohol, and a composition comprising Ti—(O-i-$C_3H_7$)$_4$ and isopropanol.

In various examples, titanyl-oxide moieties for use herein comprise an aqueous solution of peroxotitanium acid and peroxo-modified anatase sol, which is disclosed in the literature as a room temperature route to $TiO_2$ thin films, (see Ichinose, H., et al., *Journal of Sol-Gel Science and Technology*, September 2001, Volume 22, Issue 1-2, pp 33-40, and Ichinose, H., et al., *J. Ceramic Soc. Japan*, Volume 104, Issue 8, pp 715-718 (1996)).

In various examples, the titanyl-oxide moieties for use herein is a sol-gel that comprises about 0.5 wt. % peroxotitanium acid and about 0.5 wt. % peroxo-modified anatase sol, remainder water. A non-limiting example of a titanyl-oxide moieties composition for use herein comprises 0.85 wt. % of a mixture of peroxotitanium acid and peroxo-modified anatase sol (titanium oxide (IV)), remainder water. In various examples, a titanyl-oxides moieties composition comprises 0.8-0.9 wt. % of a mixture of titanium oxide (IV) and peroxotitanium acid, with the remainder, i.e., 99.1-99.2 wt. %, water. In various embodiments, this sol-gel mixture may be referred to as "0.85 wt. % aqueous peroxotitanium acid and peroxo-modified anatase sol."

This titanyl sol-gel, or others prepared by other processes as discussed, may be coated onto a surface by itself, or in combination with an antimicrobial silane coating. In an example where the surface comprised a borosilicate glass slide, AFM imaging (50×50 µm² scan area) revealed a 0.85 wt. % aqueous peroxotitanium acid and peroxo-modified anatase sol coating, when dry, to have an average roughness of 25.76 nm. In an example where the surface comprised mica, AFM imaging (1 µm² scan area) revealed a 0.85 wt. % aqueous peroxotitanium acid and peroxo-modified anatase sol coating, when dry, provides an average particle size of 30 nm. Although not wishing to be bound by any particular theory, these particles may comprise, at least in part, nanoparticulate $TiO_2$.

GENERAL EMBODIMENTS

In various embodiments of the composition and method, a coating is formed on a surface, where that coating comprises an organosilane. In certain examples, the silane comprises an organosilane homopolymer.

In various embodiments of the composition and method, a coating is formed on a surface, where that coating comprises a plurality of titanium-oxygen bonds, where that coating is formed by disposing on the surface a mixture of Peroxotitanium acid solution and Peroxo-modified anatase sol (collectively referred to herein as "Titanium-Oxygen Moieties").

In various embodiments, Titanium-Oxygen Moieties comprises up to about a total of one weight percent loading of the mixture of Peroxotitanium acid solution and Peroxo-modified anatase sol. In certain examples, Titanium-Oxygen Moieties comprises 0.85 wt. % of a mixture of Peroxotitanium acid solution and Peroxo-modified anatase sol in water. In various embodiments, Titanium-Oxygen Moieties comprises about 0.5 weight percent Peroxotitanium acid solution in combination with about 0.5 weight percent Peroxo-modified anatase sol.

Figure 4:
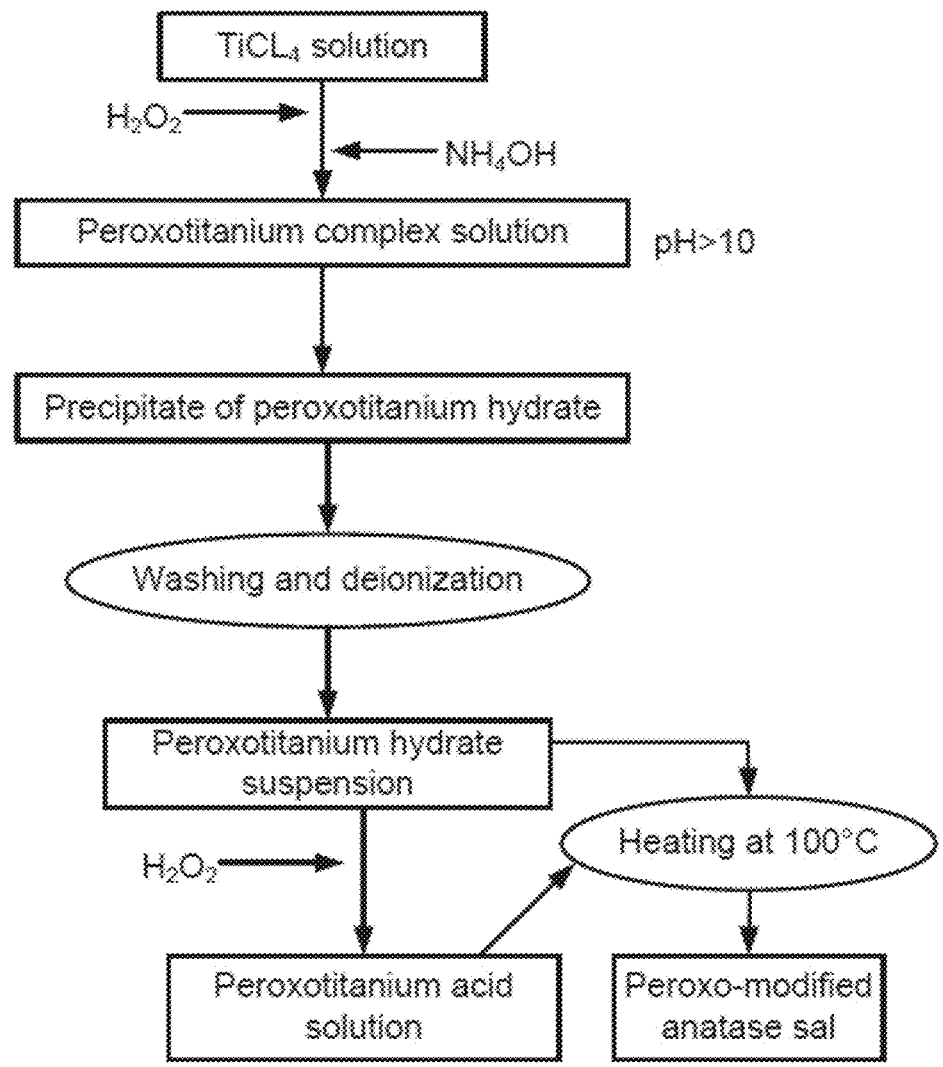
FIG. 4 shows a flowchart of an embodiment of a synthetic procedure to produce peroxotitanium acid solution and peroxo-modified anatase sol, in accordance with various embodiments.

A method to prepare both Peroxotitanium acid solution and Peroxo-modified anatase sol is disclosed in Ichinose, H., et al., *Journal of Sol-Gel Science and Technology*, September 2001, Volume 22, Issue 1-2, pp 33-40. This publication discloses, inter alia, Reaction Scheme 1, shown in FIG. 4, which summarizes the synthetic procedure for both Peroxotitanium acid solution and Peroxo-modified anatase sol. Further disclosure is found in Ichinose, H., et al., *J. Ceramic Soc. Japan*, Volume 104, Issue 8, pp 715-718 (1996).

In various embodiments of the composition and method, the coating formulation comprises a mixture of Peroxotitanium acid solution and Peroxo-modified anatase sol. In another embodiment of the composition and method, a coating is formed on a surface of an object, where that coating comprises a plurality of titanium-oxygen bonds in combination with a plurality of silicon-oxygen bonds, and where that coating is formed by disposing a mixture of Peroxotitanium acid solution and Peroxo-modified anatase sol, in combination with an organosilane onto the surface.

In various embodiments, a coating comprising a plurality of titanium-oxygen bonds in combination with a plurality of silicon-oxygen bonds is formed by first disposing on the surface an organosilane followed by disposing a mixture of Peroxotitanium acid solution and Peroxo-modified anatase sol onto the organosilane.

In various embodiments, a coating comprising a plurality of titanium-oxygen bonds in combination with a plurality of silicon-oxygen bonds is formed by first disposing a mixture of Peroxotitanium acid solution and Peroxo-modified anatase sol on the surface followed by disposing an organosilane onto the mixture of Peroxotitanium acid solution and Peroxo-modified anatase sol. In various embodiments, a coating comprising a plurality of titanium-oxygen bonds in combination with a plurality of silicon-oxygen bonds is formed by simultaneously disposing a mixture of Peroxotitanium acid solution and Peroxo-modified anatase sol and an organosilane onto the surface.

In various embodiments, organosilane comprises organosilane 1,

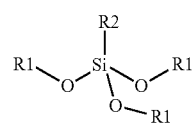

In various embodiments, both R1 and R2 are alkyl. In other embodiments R1 is alkyl and R2 is alkyl with an amino moiety. In various embodiments, R1 is alkyl and R2 is alkyl with a quaternary ammonium group. In various embodiments, R1 is alkyl and R2 is alkyl with a chlorine moiety. In various embodiments, R1 is alkyl and R2 is selected from the group consisting of —O—$CH_3$ and —O—$CH_2$—$CH_3$.

In various embodiments, organosilane comprises a trihydroxy silane 2. In various embodiments, R2 is alkyl. In other embodiments R2 is alkyl with an amino moiety. In various embodiments, R2 is alkyl with a quaternary ammonium group. In various embodiments, R2 is alkyl with an amino or chlorine moiety. In various embodiments, R2 is —OH.

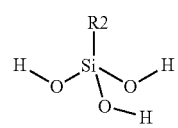

In various embodiments, organosilane comprises a silanetriol 2, wherein R2 is alkyl. In other embodiments, organosilane comprises a silanetriol 2, wherein R2 is alkyl with an amino moiety. In various embodiments, organosilane comprises a silanetriol 2, wherein R2 is alkyl with a quaternary ammonium group.

As those skilled in the art will appreciate and as shown in Equation (1), silyl esters, such as silyl ester 1, are readily hydrolysable into a corresponding silanetriol, such as silanetriol 2. Exposure to atmospheric moisture may be sufficient to hydrolyze silyl ester 1 into silanetriol 2.

EQUATION (1)

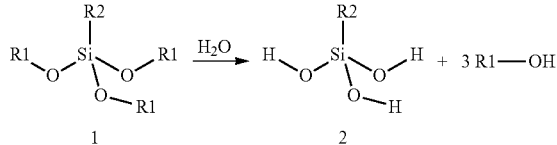

A silsesquioxane is an organosilicon compound 3. In various embodiments, R2 is alkyl. In other embodiments, R2 is alkyl with an amino moiety. In various embodiments, R2 is alkyl with a chlorine moiety. In various embodiments, R2 is alkyl with a quaternary ammonium group.

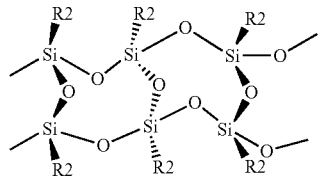

In various embodiments, after application of silanetriol 2 to a hard surface, i.e. wall, door, table, and the like, a resulting coating disposed on the hard surface comprises a plurality of silsesquioxane 3 structures. In various embodiments, after application of silanetriol 2 in combination with titanium dioxide to either a hard surface, i.e. wall, door, table, and the like, a resulting coating disposed on the hard surface comprises a plurality of silsesquioxane structures 3 in combination with Titanium-Oxygen Moieties.

In various embodiments, an aqueous antimicrobial coating composition comprises an aqueous mixture of at least one organosilane homopolymer and, optionally, at least one amine.

In various embodiments, an aqueous antimicrobial coating composition consists essentially of from about 0.01 wt. % to about 15 wt. % total organosilane homopolymers, with the remainder being water.

In various embodiments, an aqueous antimicrobial coating composition consists essentially of from about 0.01 wt. % to about 15 wt. % total organosilane homopolymers, from about 0.01 wt. % to about 5.0 wt. % total amines, with the remainder being water.

In various embodiments, an aqueous antimicrobial coating composition consists essentially of from about 0.01 wt. % to about 15 wt. % total organosilane homopolymers, from about 0.01 wt. % to about 5.0 wt. % triethanolamine, with the remainder being water.

In various embodiments, an aqueous antimicrobial coating composition consists essentially of from about 0.01 wt. % to about 15 wt. % total organosilane homopolymers, from about 0.01 wt. % to about 1.0 wt. % triethanolamine, with the remainder being water.

In various embodiments, the at least one organosilane homopolymer comprises the polymeric structure,

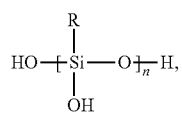

wherein:
  $n \geq 2$; and
  R=
    —$(CH_2)_m$—X, wherein m=1 to 6, X=$^+N(CH_3)_2(C_{18}H_{37})$ Cl$^-$, $NH_2$, Cl, Br, or I;
    —$(CH_2)_3$—NH—$(CH_2)_2$—$NH_2$;
    —$(CH_2)_3$—NH—$(CH_2)_2$—NH—$(CH_2)_2$—$NH_2$;
    —$(CH_2)$—NH—$(CH_2)_6$—$NH_2$;
    —$(CH_2)_3$—NH—$(CH_2)_3$—$Si(OR^{12})_3$, wherein $R^{12}$=H, —$CH_3$ or —$CH_2CH_3$; or
    —$(CH_2)_3$—NH—$(CH_2)_2$—NH—$(CH_2)_3$—$Si(OR^{12})_3$, wherein $R^{12}$=H, —$CH_3$ or —$CH_2CH_3$.

The phrase "at least one organosilane homopolymer" refers to having at least one organosilane species in solution that has self-polymerized into a distribution of homopolymers, not that there is at least one homopolymer chain length present for a particular organosilane species. Thus, "at least one" indicates there may be two or more organosilanes, wherein each organosilane further comprises its own separate distribution of homopolymers. Also, the chain length distribution for a particular organosilane may be unique to that organosilane, e.g., n=from 2 to about 30, or n=from 3 to about 30. In some instances, the chain length distribution for a particular organosilane may be unknown, and thus indicated as $n \geq 2$. For mixtures of organosilanes having both known and unknown chain length distributions, the mixture may be indicated as $n \geq 2$ or $n \geq 3$.

In various embodiments, R is 3-aminopropyl, 3-chloropropyl or —$(CH_2)_3$—$^+N(CH_3)_2(C_{18}H_{37})$Cl$^-$. In certain aspects, the organosilane homopolymer comprises 3-aminopropylsilanetriol homopolymer with a chain length distribution of from 2 to about 30.

In various embodiments, the at least one organosilane homopolymer comprises 3-(trihydroxysilyl)propyl dimethyloctadecyl ammonium chloride homopolymer with a chain length distribution of $n \geq 2$. Mass spectrometry (MS) shows a highest m/z value of 2936.9 for aqueous solutions of 3-(trihydroxysilyl)propyl dimethyloctadecyl ammonium chloride. The monomer has a molecular weight of 454.29 g/mole, and it remains possible charged quaternary ammonium fragments are lost during MS detection. Because of this complicated situation, an estimation of the chain length distribution is not attempted, but rather the homopolymer distribution is indicated as $n \geq 2$. In various examples, an aqueous antimicrobial coating composition is made by diluting dimethyloctadecyl 3-(trimethoxysilyl)propyl ammonium chloride in water. A non-limiting commercial source of dimethyloctadecyl 3-(trimethoxysilyl)propyl ammonium chloride is Sigma-Aldrich, in the form of a 42 wt. % actives solution in methanol. In other examples, an aqueous antimicrobial coating composition is made by diluting 3-(trihydroxysilyl)propyl dimethyloctadecyl ammonium chloride in water.

3-(trihydroxysilyl)propyl dimethyloctadecyl ammonium chloride is commercially available, for example, from INDUSCO, Inc. in 0.5 wt. %, 0.75 wt. %, 1.5 wt. % and 71.20 wt. % aqueous solutions, under the trade name BioShield®. The 5 wt. % solution of 3-(trihydroxysilyl)propyl dimethyloctadecyl ammonium chloride is also available from INDUSCO, Inc. under the trade name ProShield®

5000D, having EPA Reg. No. 53053-8. The label for ProShield® 5000D further lists the active ingredient as "octadecylaminodimethyltrihydroxysilyl propyl ammonium chloride," (which is perhaps an incorrect name for 3-(trihydroxysilyl)propyl dimethyloctadecyl ammonium chloride). Another supplier of 5 wt. % aqueous octadecylaminodimethyltrihydroxysilyl propyl ammonium chloride is Gelest, Inc., 11 East Steel Rd., Morrisville, Pa. 19067 USA. The Gelest MSDS discloses this product as containing 94-96 wt. % water and 4-6 wt. % octadecylaminodimethyltrihydroxysilyl propyl ammonium chloride. These various commercial materials may be diluted in water to the desired wt. % organosilane homopolymer in a method to form aqueous antimicrobial coating compositions. Optionally, at least one amine may be added to the aqueous mixture.

In various embodiments, the at least one organosilane homopolymer comprises a mixture of 3-aminopropylsilanetriol homopolymer, 3-(trihydroxysilyl)propyl dimethyloctadecyl ammonium chloride homopolymer and 3-chloropropylsilanetriol homopolymer.

In certain examples, the antimicrobial coating composition comprises at least one organosilane homopolymer selected from the group consisting of:

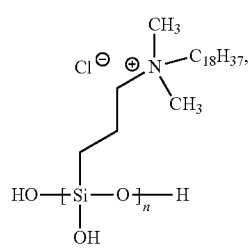
(102)

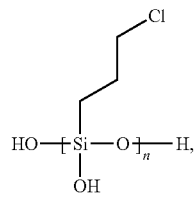
(104)

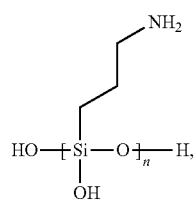
(106)

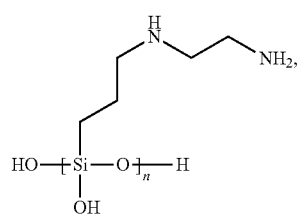
(108)

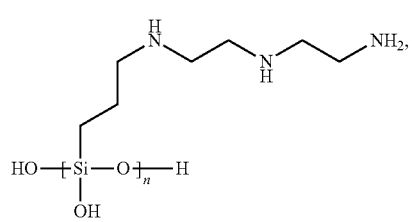
(110)

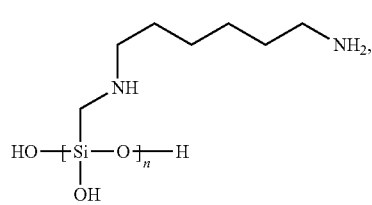
(112)

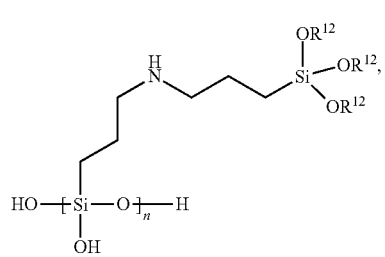
(114)

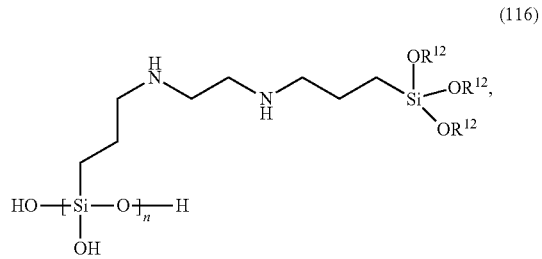
(116)

or mixtures thereof,
wherein n≥2, and each $R^{12}$ when present is independently H, —$CH_3$ or —$CH_2CH_3$.

The organosilane homopolymers above, namely 102, 104, 106, 108, 110, 112, 114 and 116, may be obtained by diluting the corresponding monomer, (e.g., the corresponding silanetriol, triethoxysilane or trimethoxysilane), in water, whereby the organosilane hydrolyzes (if an alkoxysilane) and self-polymerizes in accordance to the following non-limiting reaction schemes:

Reaction Scheme A

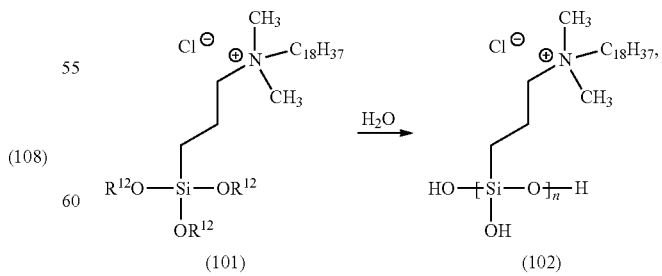

(101)       (102)

wherein n≥2, and each $R^{12}$ is independently H, —$CH_3$ or —$CH_2CH_3$. In various embodiments, organosilane 101 comprises 3-(trihydroxysilyl)propyl dimethyloctadecyl ammonium chloride (herein, "2015" or "DMOD"), 3-(trimethoxysilyl)propyl dimethyloctadecyl ammonium chloride or 3-(triethoxysilyl)propyl dimethyloctadecyl ammonium chloride.

Reaction Scheme B

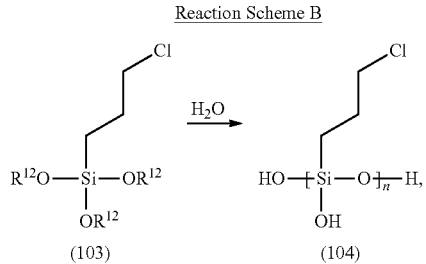

wherein n≥2, and each $R^{12}$ is independently H, —$CH_3$ or —$CH_2CH_3$. In various embodiments, organosilane 103 comprises 3-chloropropyltrimethoxysilane (herein, "2020" or "CPTMS") or 3-chloropropyltriethoxysilane.

Reaction Scheme C

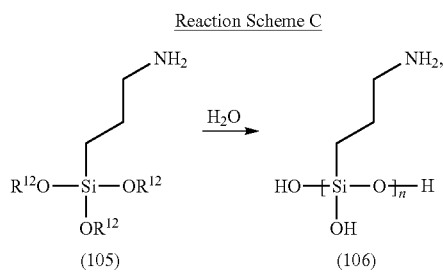

wherein n=2 to about 30, and each $R^{12}$ is independently H, —$CH_3$ or —$CH_2CH_3$. In various embodiments, organosilane 105 comprises 3-aminopropyltrimethoxysilane or 3-aminopropyltriethoxysilane (herein, "3-APTES" or "2030").

Reaction Scheme D

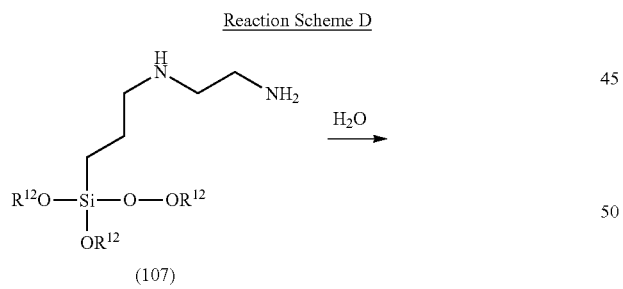

wherein n≥2, and each $R^{12}$ is independently H, —$CH_3$ or —$CH_2CH_3$. Organosilane 107 comprises N-(2-aminoethyl)-3-aminopropyl trimethoxysilane or N-(2-aminoethyl)-3-aminopropyl triethoxysilane (herein, "0590").

Reaction Scheme E

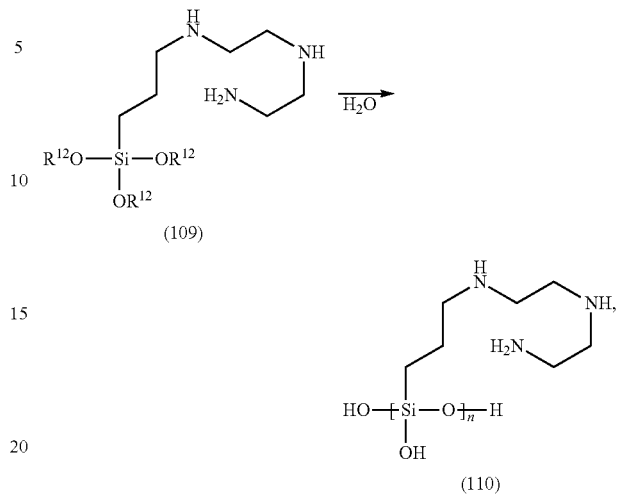

wherein n≥2, and each $R^{12}$ is independently H, —$CH_3$ or —$CH_2CH_3$. Organosilane 109 comprises $N^1$-(3-trimethoxysilylpropyl) diethylenetriamine or $N^1$-(3-triethoxysilylpropyl) diethylenetriamine (herein, "8398").

Reaction Scheme F

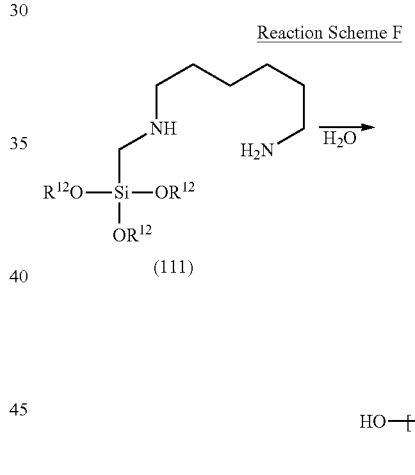

wherein n≥2, and each $R^{12}$ is independently H, —$CH_3$ or —$CH_2CH_3$. Organosilane 111 comprises N-(6-aminohexyl) aminomethyl trimethoxysilane or N-(6-aminohexyl) aminomethyl triethoxysilane (herein, "0592").

Reaction Scheme G

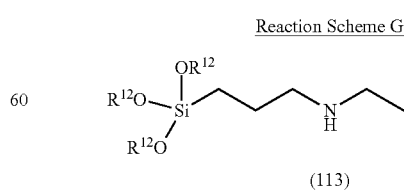

-continued

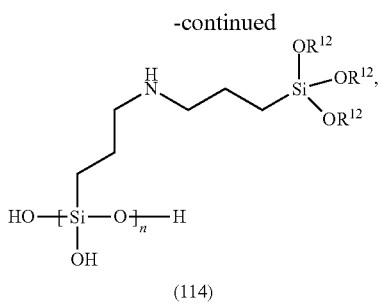

(114)

wherein n≥2, and each $R^{12}$ is independently H, —$CH_3$ or —$CH_2CH_3$. The organosilane 113 may be symmetrical, in that each $R^{12}$ may be the same. Organosilane 113 comprises bis[3-(trimethoxysilyl)propyl]amine or bis[3-(triethoxysilyl)propyl]amine. The homopolymer 114 formed upon hydrolysis may comprise any degree of intramolecular bonding and/or may exist with both ends polymerized to the same or to different degrees. When fully hydrolyzed and self-polymerized at both ends, homopolymer 114 can bond to a surface at both ends, leaving a loop comprising —$(CH_2)_3NH(CH_2)_3$— protruding out from the surface.

Reaction Scheme H

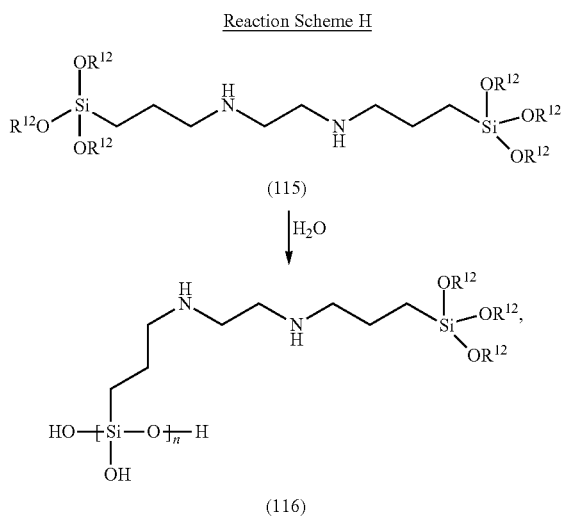

wherein n≥2, and each $R^{12}$ is independently H, —$CH_3$ or —$CH_2CH_3$. The organosilane 115 may be symmetrical, in that each $R^{12}$ may be the same. Organosilane 115 comprises N,N'-bis[3-(trimethoxysilyl)propyl]ethylenediamine or N,N'-bis[3-(triethoxysilyl)propyl]ethylenediamine. The homopolymer 116 formed upon hydrolysis may comprise any degree of intramolecular bonding and/or may exist with both ends polymerized to the same or to different degrees. When fully hydrolyzed and self-polymerized at both ends, homopolymer 116 can bond to a surface at both ends, leaving a loop comprising —$(CH_2)_3NHCH_2CH_2NH(CH_2)_3$— protruding out from the surface.

In various embodiments, each of the homopolymers 102, 104, 106, 108, 110, 112, 114 and 116 may exhibit either or both contact disinfection/sanitization efficacy, when disposed onto microorganisms as a germicidal spray product, and residual self-sanitization efficacy when dried as a film on a surface onto which microorganisms come into contact. In other words, any of the aqueous antimicrobial coating compositions disclosed herein may exhibit this dual function.

In various embodiments, the antimicrobial coating composition comprises from about 0.01 wt. % to about 15 wt. % of 3-(trihydroxysilyl)propyl dimethyloctadecyl ammonium chloride homopolymer 102 having a chain length distribution of n≥2. The remainder of the composition may consist essentially of water. The antimicrobial coating composition may optionally comprise at least one amine.

In certain examples, the antimicrobial coating composition comprises from about 0.01 wt. % to about 15 wt. % of 3-chloropropylsilanetriol homopolymer 104 having a chain length distribution of n≥2. The remainder of the composition may consist essentially of water. The antimicrobial coating composition may optionally comprise at least one amine.

In certain examples, the antimicrobial coating composition comprises from about 0.01 wt. % to about 15 wt. % of 3-aminopropylsilanetriol homopolymer 106 having a chain length distribution of n=2 to about 30 (dimer up to about a 30-mer). The remainder of the composition may consist essentially of water. The antimicrobial coating composition may optionally comprise at least one amine, the presence of which can alter the chain length distribution, e.g., loss of the dimer.

In certain examples, the antimicrobial coating composition consists essentially of from about 0.01 wt. % to about 15 wt. % of 3-aminopropylsilanetriol homopolymer 106 having a chain length distribution of n=2 to about 30 (dimer up to about a 30-mer), with the remainder being water.

In certain examples, the antimicrobial coating composition consists essentially of from about 0.01 wt. % to about 15 wt. % of 3-aminopropylsilanetriol homopolymer 106 having a chain length distribution of n=3 to about 30 (trimer up to about a 30-mer), from about 0.01 wt. % to about 5.0 wt. % triethanolamine, the remainder being water.

In certain examples, the antimicrobial coating composition consists essentially of from about 0.01 wt. % to about 15 wt. % of 3-aminopropylsilanetriol homopolymer 106 having a chain length distribution of n=3 to about 30 (trimer up to about a 30-mer), less than about 1.0 wt. % triethanolamine, the remainder being water.

In certain examples, the antimicrobial coating composition comprises a total of from about 0.01 wt. % to about 15 wt. % of a mixture of 3-(trihydroxysilyl)propyl dimethyloctadecyl ammonium chloride homopolymer 102 having a chain length distribution of n≥2 and 3-aminopropylsilanetriol homopolymer 106 having a chain length distribution of n=2 to about 30 (trimer up to about a 30-mer). The remainder of the composition may consist essentially of water. The antimicrobial coating composition may optionally comprise at least one amine, the presence of which can alter the chain length distribution of the 3-aminopropylsilanetriol homopolymer 106, e.g., loss of the dimer.

In certain examples, the antimicrobial coating composition comprises a total of from about 0.01 wt. % to about 15 wt. % of a mixture of 3-(trihydroxysilyl)propyl dimethyloctadecyl ammonium chloride homopolymer 102 having a chain length distribution of n≥2, 3-aminopropylsilanetriol homopolymer 106 having a chain length distribution of n=2 to about 30 (dimer up to about a 30-mer) and 3-chloropropylsilanetriol homopolymer 104 having a chain length distribution of n≥2. The remainder of the composition may consist essentially of water. The antimicrobial coating composition may optionally comprise at least one amine, the presence of which can alter the chain length distribution of the 3-aminopropylsilanetriol homopolymer 106, e.g., loss of the dimer.

In certain examples, the antimicrobial coating composition consists essentially of a total of from about 0.01 wt. % to about 15 wt. % of a mixture of 3-(trihydroxysilyl)propyl dimethyloctadecyl ammonium chloride homopolymer 102 having a chain length distribution of n≥2 and 3-aminopropylsilanetriol homopolymer 106 having a chain length distribution of n=2 to about 30 (dimer up to about a 30-mer), with the remainder being water.

In certain examples, the antimicrobial coating composition consists essentially of a total of from about 0.01 wt. % to about 15 wt. % of a mixture of 3-(trihydroxysilyl)propyl dimethyloctadecyl ammonium chloride homopolymer 102 having a chain length distribution of n≥2 and 3-aminopropylsilanetriol homopolymer 106 having a chain length distribution of n=3 to about 30 (trimer up to about a 30-mer), from about 0.01 wt. % to about 5.0 wt. % triethanolamine, with the remainder being water.

In certain examples, the antimicrobial coating composition consists essentially of a total of from about 0.01 wt. % to about 15 wt. % of a mixture of 3-(trihydroxysilyl)propyl dimethyloctadecyl ammonium chloride homopolymer 102 having a chain length distribution of n≥2, 3-aminopropylsilanetriol homopolymer 106 having a chain length distribution of n=2 to about 30 (dimer up to about a 30-mer) and 3-chloropropylsilanetriol homopolymer 104 having a chain length distribution of n≥2, with the remainder being water.

In certain examples, the antimicrobial coating composition consists essentially of a total of from about 0.01 wt. % to about 15 wt. % of a mixture of 3-(trihydroxysilyl)propyl dimethyloctadecyl ammonium chloride homopolymer 102 having a chain length distribution of n≥2, 3-aminopropylsilanetriol homopolymer 106 having a chain length distribution of n=3 to about 30 (trimer up to about a 30-mer) and 3-chloropropylsilanetriol homopolymer 104 having a chain length distribution of n≥2, from about 0.01 wt. % to about 5.0 wt. % triethanolamine, with the remainder being water.

In various embodiments, the antimicrobial coating composition comprises from about 0.01 wt. % to about 15 wt. % of an organosilane homopolymer having the structure:

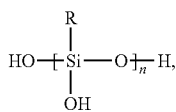

wherein:
n≥2; and R=—(CH$_2$)$_3$—NH—(CH$_2$)$_2$—NH$_2$. The remainder of the composition may consist essentially of water. The antimicrobial coating composition may optionally comprise at least one amine.

In various embodiments, the antimicrobial coating composition comprises from about 0.01 wt. % to about 15 wt. % of an organosilane homopolymer having the structure:

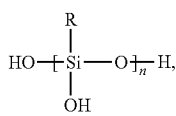

wherein:
n≥2; and R=—(CH$_2$)$_3$—NH—(CH$_2$)$_2$—NH—(CH$_2$)$_2$—NH$_2$. The remainder of the composition may consist essentially of water. The antimicrobial coating composition may optionally comprise at least one amine.

In various embodiments, the antimicrobial coating composition comprises from about 0.01 wt. % to about 15 wt. % of an organosilane homopolymer having the structure:

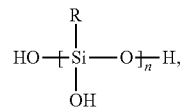

wherein:
n≥2; and R=—(CH$_2$)—NH—(CH$_2$)$_6$—NH$_2$. The remainder of the composition may consist essentially of water. The antimicrobial coating composition may optionally comprise at least one amine.

In various embodiments, the antimicrobial coating composition comprises from about 0.01 wt. % to about 15 wt. % of an organosilane homopolymer having the structure:

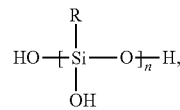

wherein:
n≥2; and R=—(CH$_2$)$_3$—NH—(CH$_2$)$_3$—Si(OR$^{12}$)$_3$, wherein R$^{12}$=H, —CH$_3$ or —CH$_2$CH$_3$. The remainder of the composition may consist essentially of water. The antimicrobial coating composition may optionally comprise at least one amine.

In various embodiments, the antimicrobial coating composition comprises from about 0.01 wt. % to about 15 wt. % of an organosilane homopolymer having the structure:

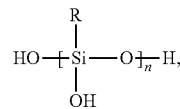

wherein:
n≥2; and R=—(CH$_2$)$_3$—NH—(CH$_2$)$_2$—NH—(CH$_2$)$_3$—Si(OR$^{12}$)$_3$, wherein R$^{12}$=H, —CH$_3$ or —CH$_2$CH$_3$. The remainder of the composition may consist essentially of water. The antimicrobial coating composition may optionally comprise at least one amine.

In various embodiments, the amine, optionally incorporated in any of the antimicrobial coating compositions disclosed herein, comprises a water-soluble primary, secondary or tertiary amine having structure R$^9$R$^{10}$R$^{11}$N, wherein R$^9$, R$^{10}$, and R$^{11}$ are independently H, alkyl, substituted alkyl, aryl, substituted aryl or cyclic, having a molecular weight of less than about 200 g/mole and a pKa of from about 7 to about 12. In various examples, the amine comprises an amino alcohol. In certain aspects, the amine is selected from the group consisting of monoethanolamine, diethanolamine, triethanolamine, and mixtures thereof. In various examples, the at least one amine is incorporated into an antimicrobial coating composition at a total of from about 0.01 wt. % to about 5.0 wt. %. In various examples, the at least one amine is present at a total of less than about 1 wt. % in the antimicrobial coating composition. In certain examples, the amine consists of triethanolamine, incorporated at less than about 1 wt. % in the antimicrobial coating composition.

Antimicrobial coating compositions comprising 3-aminopropylsilanetriol homopolymer are prepared by mixing 3-aminopropyltriethoxysilane (herein, "3-APTES") in water. This example is not meant to be limiting, as at least 3-aminopropyltrimethoxysilane (herein, "3-APTMS") could be substituted for the triethoxysilane to produce a solution of 3-aminopropylsilanetriol homopolymer. Nonetheless, the specific examples herein utilizing 3-APTES as the starting material benefit from the commercial availability of this material. Either 3-APTES or 3-APTMS will hydrolyze when diluted in water to the silanetriol and self-condense into a distribution of 3-aminopropylsilanetriol homopolymers.

Dried films comprising 3-aminopropylsilanetriol homopolymer would not be expected to exhibit any antimicrobial efficacy at all, particularly since 3-aminopropylsilanetriol homopolymer does not have any functionality recognizable as antimicrobial, such as the plurality of quaternary ammonium moieties in 3-(trihydroxysilyl)propyl dimethyloctadecyl ammonium chloride homopolymer. However, it remains possible that a plurality of exposed amino groups (—$NH_2$) in a dried coating of 3-aminopropylsilanetriol homopolymer functions in a similar way as does the plurality of dimethyloctadecyl ammonium chloride groups in a dried film of 3-(trihydroxysilyl)propyl dimethyloctadecyl ammonium chloride homopolymer, e.g., disruption of the cell membrane of an organism in contact with the film.

Similarly, the homopolymers 108, 110, 112, 114 and 116 have multiple amino functionality that can interact with microorganisms coming into contact with dried films that comprise any combination of 108, 110, 112, 114 and 116 organosilane homopolymers. As shown below, dried films from these amino organosilane homopolymers exhibit residual antimicrobial efficacy.

Antimicrobial coating compositions comprising aqueous 3-aminopropylsilanetriol homopolymer and triethanolamine are prepared by mixing 3-APTES and triethanolamine in water, wherein the 3-APTES hydrolyzes and self-condenses into a distribution of 3-aminopropylsilanetriol homopolymer chain lengths. As discussed further herein, and substantiated by MALDI-TOF mass spectrometry, there is no evidence that 3-APTES, or any of its hydrolysis and self-condensation products, reacts in any way with the triethanolamine in the antimicrobial coating composition. For the aqueous antimicrobial coating compositions comprising 3-aminopropylsilanetriol homopolymer and triethanolamine disclosed herein, there is no indication that silatranes are formed or that any heteropolymers are formed having both organosilane and triethanolamine moieties, and the compositions comprising organosilane homopolymer and triethanolamine do not change during long term storage. The absence of heteropolymers and silatranes may be due to the dilute aqueous compositions and/or the molar ratios of silane to amine in the compositions.

Since the triethanolamine does not appear to participate in any chemical reactions, at least prior to application of the composition on a surface, it is not clear how triethanolamine heightens the antimicrobial efficacy of an organosilane homopolymer coating. No theories are proffered as to the function of the triethanolamine in an antimicrobial coating comprising 3-aminopropylsilanetriol homopolymer. It remains possible the triethanolamine provides any one of (i) a pH effect on the surface; (ii) wetting of an otherwise hydrophobic surface; or, (iii) initiation and/or control of further self-condensation of the 3-aminopropylsilanetriol homopolymer as the composition concentrates and ultimately dries on the surface (i.e., formation of longer chain lengths and/or branching). In some instances, the triethanolamine might remain trapped for some period of time within a dried matrix of 3-aminopropylsilanetriol homopolymer, where it can act as a supplemental or synergistic antimicrobial agent.

In various embodiments, a method of forming an antimicrobial coating on a surface comprises disposing an aqueous antimicrobial coating composition on the surface, wherein the aqueous antimicrobial coating composition comprises at least one organosilane homopolymer having the polymeric structure,

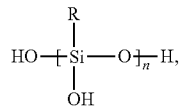

wherein:
n≥2;
R=
—$(CH_2)_m$—X, wherein m=1 to 6, X=$^+N(CH_3)_2(C_{18}H_{37})$ $Cl^-$, $NH_2$, Cl, Br, or I;
—$(CH_2)_3$—NH—$(CH_2)_2$—$NH_2$;
—$(CH_2)_3$—NH—$(CH_2)_2$—NH—$(CH_2)_2$—$NH_2$;
—$(CH_2)$—NH—$(CH_2)_6$—$NH_2$;
—$(CH_2)_3$—NH—$(CH_2)_3$—$Si(OR^{12})_3$, wherein $R^{12}$=H, —$CH_3$ or —$CH_2CH_3$; or
—$(CH_2)_3$—NH—$(CH_2)_2$—NH—$(CH_2)_3$—$Si(OR^{12})_3$, wherein $R^{12}$=H, —$CH_3$ or —$CH_2CH_3$.

In various embodiments, the antimicrobial coating composition further comprises at least one amine, as discussed above.

In certain examples, the step of disposing the composition on a surface comprises mechanical spraying or electrostatic spraying, such as to apply a fine mist on the surface. The wetted surface may be allowed to dry or may be dried mechanically e.g., by directing air and/or heat to the wetted surface. The step of "allowing the composition to dry on the surface" is meant to include both passive drying and mechanically accelerated drying, for simplicity sake.

In various embodiments, a method of forming an antimicrobial coating on a surface comprises the steps of:
(1) disposing an aqueous antimicrobial coating composition on the surface, wherein the aqueous antimicrobial coating composition comprises at least one organosilane homopolymer having the polymeric structure,

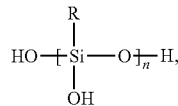

wherein:
n≥2;
R=
—$(CH_2)_m$—X, wherein m=1 to 6, X=$^+N(CH_3)_2(C_{18}H_{37})$ $Cl^-$, $NH_2$, Cl, Br, or I;
—$(CH_2)_3$—NH—$(CH_2)_2$—$NH_2$;
—$(CH_2)_3$—NH—$(CH_2)_2$—NH—$(CH_2)_2$—$NH_2$;
—$(CH_2)$—NH—$(CH_2)_6$—$NH_2$;
—$(CH_2)_3$—NH—$(CH_2)_3$—$Si(OR^{12})_3$, wherein $R^{12}$=H, —$CH_3$ or —$CH_2CH_3$; or
—$(CH_2)_3$—NH—$(CH_2)_2$—NH—$(CH_2)_3$—$Si(OR^{12})_3$, wherein $R^{12}$=H, —$CH_3$ or —$CH_2CH_3$; and (2) disposing on the surface an aqueous composition of titanium sol.

In various embodiments, the antimicrobial coating composition in this method further comprises at least one amine, as discussed above.

In certain examples, each of the steps of disposing the organosilane and titanium sol comprise mechanical spraying or electrostatic spraying. The organosilane polymers and Ti-sol may be applied to the surface in either order or simultaneously. There may be any lapse of time allowed between the two coating steps if performed stepwise, and the surfaces may be coated with multiple coatings either silane or titanium composition. The wetted surface may then be allowed to dry or may be dried by directing air and/or heat to the wetted surface to produce the antimicrobial coating on the surface in the form of a dried thin film.

In various embodiments, an antimicrobial coating is prepared on a surface by a method comprising: (1) coating a portion of the surface with an aqueous antimicrobial coating composition comprising at least one organosilane homopolymer and optionally at least one amine; and (2) subsequently coating the portion of the surface with 0.85 wt. % aqueous peroxotitanium acid and peroxo-modified anatase sol. In a non-limiting example that demonstrates this two-step application, borosilicate glass slides were positioned vertically and electrostatic spray coated from a distance of about 5 to 6 feet with the aqueous 3-(trihydroxysilyl)propyl dimethyloctadecyl ammonium chloride and triethanolamine solution and allowed to dry about 3 to 5 minutes, after which time the 0.85 wt. % aqueous peroxotitanium acid and peroxo-modified anatase sol was electrostatic spray coated overtop of the organosilane from about 5 to 6 feet distance. The treated slides were left to dry at room temperature overnight. AFM imaging (50×50 μm² scan area) revealed that the coating resulting from this two-step sequential surface treatment had an average thickness of 51.79±17.98 nm, and an average roughness of 35.90±9.43 nm.

The method of stepwise surface treatment may be performed in the opposite order. For example, a portion of a surface may be coated first with an aqueous solution of peroxotitanium acid and peroxo-modified anatase sol, and then the same portion of the surface subsequently coated with an antimicrobial coating composition comprising at least one organosilane homopolymer and optionally at least one amine, such that the organosilane homopolymer composition is theoretically overtop the titanyl species layer. For either order of application, the first coating may be allowed to partly dry or completely dry prior to the subsequent coating. In other aspects, the first treatment may be applied, and while still wet, followed by the second treatment, and then the combined treatments are allowed to dry. Throughout this disclosure, stepwise treatment of a surface is meant to target approximately the same portion of the surface with successive compositions. In some instances, a second treatment may liquefy a coating applied first and dissolve those components that were first dried on the surface.

The following Examples are presented to further illustrate to persons skilled in the art how to make and use certain aspects. These Examples are not intended as limitations, however, upon the scope of the disclosure.

Example I

A study was conducted at the Glendale Memorial Hospital and Health Center in Glendale, Calif. (the "Glendale Memorial Hospital Study"). The Center has a 24 bed intensive care (ICU). The study was performed between May 10 and Sep. 30, 2013.

The Glendale Memorial Hospital Study was designed to assess the anti-microbial properties of the coating composition and method, wherein the method employed utilized an initial coating of organosilane followed by an overspray of titanium dioxide. The entire ICU was subjected to the two step spray regime to treat all objects in each room including hard surfaces (beds, tray tables, bed rail, walls, etc.) and soft surfaces (drapes, cloth and vinyl covered chairs, woven fabrics, non-woven fabrics, leather goods, and the like). The goal of the Glendale Memorial Hospital Study was to assess the anti-microbial efficacy of the coating composition in a practical application in a health care environment.

Each surface was first electrostatically spray coated at room temperature using an aqueous composition formed by mixing Octadecylaminodimethyltrihydroxysilylpropyl Ammonium Chloride 6 at 3.6 weight percent in water.

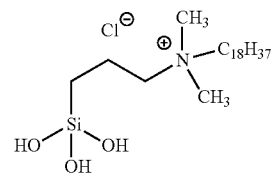

6

About fifteen (15) minutes after the electrostatic spray coating using the aqueous mixture of Octadecylaminodimethyltrihydroxysilylpropyl Ammonium Chloride 6, most of the water had evaporated leaving a coating comprising at least ninety weight percent (90 wt. %) Octadecylaminodimethyltrihydroxysilylpropyl Ammonium Chloride 6. Thereafter, each surface was then electrostatically spray coated at room temperature using Titanium-Oxide Moieties. After about 15 minutes, most of the water in the second spray deposition had evaporated leaving a coating comprising at least ninety weight percent (90 wt. %) Titanium-Oxide Moieties.

The treated surfaces were maintained at room temperature during the spray deposition of the aqueous Octadecylaminodimethyltrihydroxysilylpropyl Ammonium Chloride 6, and during the spray deposition of Titanium-Oxide Moieties. None of the treated objects were subjected to any elevated heat treatment wherein the treated surface was heated to a temperature greater than about room temperature during or after completion of the spray coating regime.

Applicants have found that using their two step, spray coating protocol described hereinabove, after evaporation of the water from the spray deposited Titanium-Oxide Moieties and evaporation of the water portion from the spray deposited aqueous Octadecylaminodimethyltrihydroxysilylpropyl Ammonium Chloride, the combined weight of Titanium-Oxide Moieties and Octadecylaminodimethyltrihydroxysilylpropyl Ammonium Chloride disposed on a treated surface was measured as 0.76 mg/in².

Initial microbial sampling of various fomites was conducted to assess the levels of bacteria on various hospital surfaces before selecting study sites. After review, 95 sites were selected for the study in the ICU. Each of the ninety-five (95) specific sites in the ICU were selected for recurring sampling at weeks 1, 2, 4, 8, and 15, after application of composition. Those selected sites included bed rails, bed controls, tray tables, and walls above sinks. Samples were also collected from the two ICU nursing stations and waiting lobby including countertops, phones, computer keyboards, chair armrests and end tables. All movable items were inconspicuously tagged and coded over the course of the study so that the same objects could be sampled.

Each of the sites was cultured prior to application of the method, and at 1 week (6-8 days), 2 weeks (13-17 days), 4 weeks (29-32 days), 8 weeks (59-62 days), 15 weeks (104-107 days) after application. Some objects were removed and were not available for culture at some of the subsequent time points.

Areas of 100 cm$^2$ were sampled using a sponge stick containing Letheen broth (3M, St. Paul, Minn.) to neutralize any residual disinfectant. After collection the samples were immediately placed on ice packs and sent overnight to the University of Arizona. Upon receipt the broth was extracted from the sponge stick by manual agitation, and then 4 mL of extracted broth was assayed using selective media for isolation of the various bacteria. Samples were cultured for total bacteria, *Clostridium difficile*, methicillin-resistant *Staphylococcus aureus* (MRSA), vancomycin-resistant *Enterococcus* (VRE), and carbapenem-resistant Enterobacteriaceae (CRE). Test methods for each organism are presented in the table in FIG. 5.

The average number of total bacteria detected per 100 cm$^2$ at all locations and percent reductions in total bacterial numbers after treatment are shown in FIG. 6.

As can be seen bacterial numbers were always 99.9% less after the treatment for four weeks, 99% after eight weeks and still almost 99% after 15 weeks.

Also, significantly the number of sites containing more than 10,000 CFU/100 cm$^2$ was reduced from 25.2% of the sites before treatment to zero for the next eight weeks and after even 15 weeks only 11.1% of the sites exceeded this number as shown in the table in FIG. 7.

Bootstrapping Analysis of Variance (ANOVA) was conducted for each stage between the baseline concentrations for the sampled fomites and the intervention concentrations for the same fomites to determine statistical significant differences based on a rejection region of 5%. Based on the p-values (<0.0005) there was a statistical significance difference between the baseline concentrations and the fomite concentrations during the entire 15 weeks of the study.

The percent of samples in which antibiotic resistant bacteria were isolated at the different sites sampled is shown in the table in FIG. 8.

Antibiotic resistant bacteria were isolated from all study areas during the baseline sampling, except *C. difficile*. VRE was the most commonly isolated organism.

Prior to treatment antibiotic resistant bacteria were isolated from 25% of the sites sampled. After treatment, no antibiotic bacteria were isolated until week 8, when VRE in 1 sample (from a chair armrest) of 64 samples (1.5%) was found.

The present study demonstrates that the use of the method reduced the numbers of bacteria on fomites by greater than 99% for 8 weeks after a single treatment (FIG. 6).

Levels of bacteria were reduced by 99.9% at 4 weeks post-treatment. Overall average levels of bacteria never returned to those observed before treatment. Bacterial numbers increased between 8 and 15 weeks post-treatment but the average bacterial count on all treated surfaces was still less than 90% after 15 weeks. No values above 10,000 CFU/100 cm$^2$ were seen for 4 weeks after treatment vs. 25.2% pre-treatment and even after 15 weeks only 11.1% of the values exceeded this amount.

No antibiotic resistant bacteria were isolated until 8 weeks after the treatment, and then at levels below that seen before the treatment (FIG. 8). No MRSA or CRE were isolated even after 15 weeks post-treatment and VRE only after 8 weeks. No *C. difficile* were isolated during the baseline or after the treatment. However, *C. difficile* was isolated in the initial screening used to select the sampling sites.

In conclusion, the anti-microbial effects resulting from use of the composition and method was found to have persisted over 15 weeks in reducing the total number of bacteria and antibiotic resistant bacteria on both hard surfaces and soft surfaces within an ICU. The hard surfaces included bare metal surfaces, painted metal surfaces, epoxy-coated surfaces, unpainted wood surfaces, painted wood surfaces, and glass.

The fifteen weeks antimicrobial efficacy demonstrates that the composition forms a coating on a treated surface, where that coating is both antifouling and antimicrobial. The composition and the resulting coating formed therefrom can generate self-decontaminating surfaces that comprise both antifouling and antimicrobial properties, thereby, providing a cost-effective route to minimize transmission of disease via high touch surfaces in healthcare and industrial applications.

FIG. 1 graphically shows the number of hospital acquired *C-difficile* infections in the Glendale Memorial Hospital ICU from January 2012 through February 2014. FIG. 1 indicates that with the exception of September 2013, there were no hospital acquired *C-difficile* infections originating in the ICU during the period May 2013 through November 2013. Thus, FIG. 1 shows that there was a single hospital acquired *C-difficile* infection originating in the ICU during the six month period. May 2013 through November 2013.

FIG. 1 further shows that, other than the six month period May 2013 through November 2013, there was no other 6 month period during the 25 months from January 2012 through February 2014 wherein only a single hospital acquired *C-difficile* infection originated in the ICU. All surfaces in the ICU were treated as described hereinabove during the first week of May 2013 as part of the Glendale Memorial Hospital Study.

Figure 2:
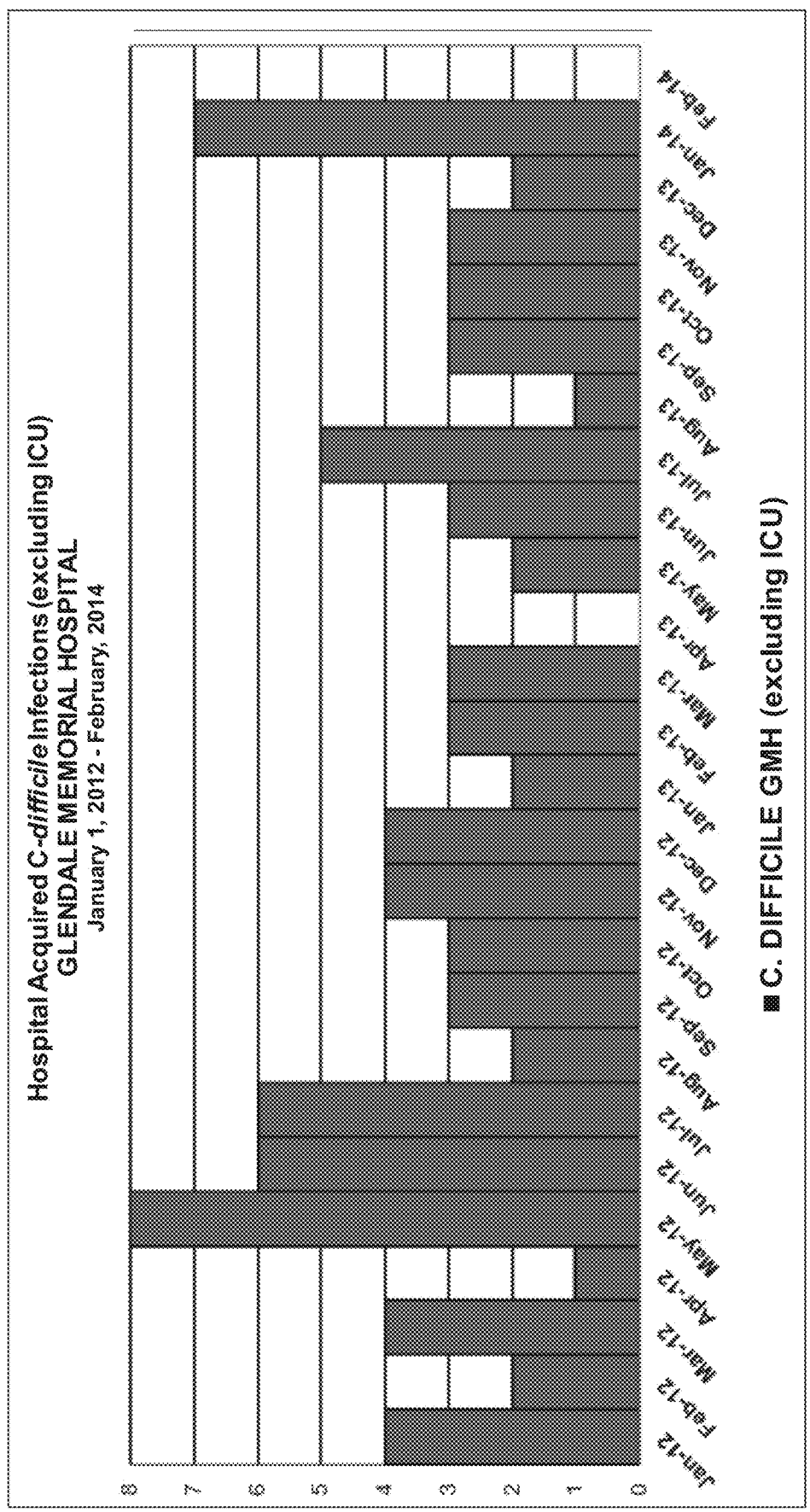
FIG. 2 graphically shows the number of hospital acquired *C-difficile* infections at the Glendale Memorial Hospital (excluding ICU) from January 2012 through February 2014, in accordance with various embodiments.

FIG. 2 graphically shows the number of hospital acquired *C-difficile* infections at the Glendale Memorial Hospital (excluding ICU) from January 2012 through February 2014. FIG. 2 indicates that, with the exception of April 2013, there were between 1 and 8 hospital acquired *C-difficile* infections every month during the 25 month period in hospital areas outside of the ICU. During the period May 2013 through November 2013, FIG. 2 shows that there were a total of 20 hospital acquired *C-difficile* infections originating outside of the ICU at the Glendale Memorial Hospital.

FIGS. 1 and 2 show that during the period May 2013 through November 2013, a single hospital acquired *C-difficile* infection originated in the ICU at the Glendale Memorial Hospital, and a total of 20 hospital acquired *C-difficile* infections originated outside of the ICU at the Glendale Memorial Hospital.

Applicants have found that they can dispose Octadecylaminodimethyltrihydroxysilylpropyl Ammonium Chloride and Applicants Titanium-Oxide Moieties, by spray deposition or by dip coating, onto a dressing prior to use of that dressing to cover a wound. As those skilled in the art will appreciate, a dressing is a sterile pad or compress applied to a wound to promote healing and/or prevent further harm. A dressing is designed to be in direct contact with the wound, as distinguished from a bandage, which is most often used to hold a dressing in place. In various embodiments, the wound dressings including the following: alginates and other fiber gelling dressings including ropes and sheets, composite dressings, foam dressings with and without adhesive border, gauze with and without adhesive border, hydrocolloids, specialty absorptive dressings with and without adhesive borders, transparent films, collagen dressings sheets and ropes, hydrogel sheets with and without adhesive border, cotton packing strips, roll gauze, paper tape, silk tape, compression bandages (elastic, knitted/woven), self-adherent bandage (elastic, non-knitted/non-woven).

Example II

This Example II disposes the components of the composition onto a target surface in a reverse order. More specifically, Applicants first dispose the Titanium-Oxide Moieties onto the target surface, the aqueous portion of the first spray deposition is evaporated, and then dispose Octadecylaminodimethyltrihydroxysilylpropyl Ammonium Chloride 6 over the earlier-disposed Titanium-Oxide Moieties.

The test coupons of this Example II were prepared and using the Procedure recited immediately hereinbelow. In various embodiments, the treated coupons were stored for at least four (4) weeks prior to inoculation with various organisms.

FIG. 9 recites efficacy data for the treated coupons after inoculation with E. coli. FIG. 10 recites efficacy data for the treated coupons after inoculation with MS-2. FIG. 11 recites efficacy data for the treated coupons after inoculation with MRSA.

In summary, the tabular data set forth in FIGS. 9, 10 and 11 demonstrate that first disposing the Titanium-Oxide Moieties onto a target surface followed by disposing Octadecylaminodimethyltrihydroxysilylpropyl Ammonium Chloride 6 over the earlier-formed Titanium-Oxide Moieties coating, generates a self-decontaminating surface.

Procedure

Put on sterile gloves.

Prepare the test coupons by wiping them first with ISP Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

First Coat—Titanium-Oxide Moieties Application

Add the Titanium-Oxide Moieties to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Rinse spray gun with distilled water prior to applying the Titanium-Oxide Moieties (unless using 2 sprayers, one for each product).

Second Coat—Organosilane Application

Add the Octadecylaminodimethyltrihydroxysilylpropyl Ammonium Chloride 6 to applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example III

This Example III simultaneously disposes a mixture of the organosilane and the Titanium-Oxide Moieties onto the surface of a plurality of test coupons. More specifically in this Example III, the simultaneously dispose the Titanium-Oxide Moieties and Octadecylaminodimethyltrihydroxysilylpropyl Ammonium Chloride 6 onto a surface of each test coupon.

The test coupons of this Example III were prepared and using the Procedure recited immediately hereinbelow. In various embodiments, the treated coupons were stored for at least four (4) weeks prior to inoculation with various organisms.

FIG. 12 recites efficacy data for the treated coupons after inoculation with E. coli. FIG. 13 recites efficacy data for the treated coupons after inoculation with MS-2. FIG. 14 recites efficacy data for the treated coupons after inoculation with MRSA.

In summary, the tabular data set forth in FIGS. 12, 13 and 14 demonstrate that simultaneously disposing the Titanium-Oxygen Moieties and the organosilane onto a target surface generates a self-decontaminating surface.

Procedure

Put on sterile gloves.

Prepare the test coupons by wiping them first with ISP Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

Prepare Combined Solution

In a measured container combine 50% Octadecylamino dimethyltrihydroxy silyl propyl Ammonium Chloride aqueous mixture and 50% the Titanium-Oxide Moieties aqueous mixture.

Mix thoroughly.

Coating

Add the aqueous mixture Octadecylaminodimethyltrihydroxysilylpropyl Ammonium Chloride and the Titanium-Oxide Moieties to applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example IV

This Example IV utilizes 3-aminopropytriethoxysilane in water as the only organosilane, in combination with the Titanium-Oxide Moiety. This being the case, this example does not utilize any organosilane comprising a quaternary ammonium moiety. 3-aminopropytriethoxysilane is rapidly hydrolyzed to 3-aminopropyltrihydroxysilane 7 when mixed with water.

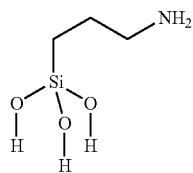

7

The test coupons of this Example IV were prepared and using the Procedure recited immediately hereinbelow. In various embodiments, the treated coupons were stored for at least four (4) weeks prior to inoculation with various organisms.

Applicants have found that using their two step, spray coating protocol described hereinbelow, after evaporation of the water from the spray deposited Titanium-Oxide Moieties and evaporation of the water portion from the spray deposited aqueous 3-aminopropyltrihydroxysilane, the combined weight of the Titanium-Oxide Moieties and 3-aminopropyltrihydroxysilane disposed on a treated surface was measured as 1.22 mg/in$^2$.

TABLES 15, 16, and 17, set forth in FIGS. 15, 16 and 17, respectively, recite efficacy data for the treated coupons after inoculation with *E. coli*. In summary, TABLES 15, 16, and 17, demonstrate that disposing a 3-aminopropyltrihydroxysilane with triethanolamine coating onto a target surface, and then disposing TiO$_2$ over the 3-aminopropyltrihydroxysilane coating generates a self-decontaminating surface.

Procedure

Put on sterile gloves.

Prepare the test coupons by wiping them first with ISP Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

Prepare Dilution for 3-Aminopropyltriethoxysilane

Prepare a 10% solution of 3-aminopropytriethoxysilane in Methanol (MeOH) (10 ml silane in 100 ml MeOH).

Prepare Triethanolamine as a 10% solution in MeOH.

Combine the triethanolamine solution and 3-aminopropytriethoxysilane solution in a 1:1 ratio on a stir plate at room temperature (ie—100 ml triethanolamine solution added to 100 ml 3-aminopropytriethoxysilane solution.

First Coat—3-Aminopropyltriethoxysilane Application

Add the mixture of triethanolamine and 3-aminopropytriethoxysilane to the applicator container.

Fasten the Liquid 1-lose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Rinse spray gun with distilled water prior to applying the Titanium Oxide Moieties (unless using 2 sprayers, one for each product).

Second Coat—the Titanium Oxide Moieties Application

Add the Titanium Oxide Moieties to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example V

This Example V utilizes 3-chloropropyltrimethoxysilane and triethanolamine in water. 3-chloropropyltrimethoxysilane is immediately hydrolyzed to 3-chloropropyltrihydroxysilane 8 when mixed with water.

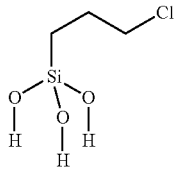

This being the case, this Example V does not utilize any organosilane(s) comprising a quaternary ammonium moiety. Furthermore, this Example V does not utilize any organosilane(s) comprising an amino moiety. Example V does contain tertiary amine.

The test coupons of this Example V were prepared using the Procedure recited immediately hereinbelow. In various embodiments, the treated coupons were stored for at least four (4) weeks prior to inoculation with various organisms.

TABLES 18, 19, and 20, set forth in FIGS. 18, 19 and 20, respectively, recite efficacy data for the treated coupons after inoculation with *E. coli*. In summary, TABLES 18, 19, and 20, demonstrates that disposing a 3-chloropropyltrihydroxysilane and triethanolamine coating on a target surface followed by disposing the Titanium Oxide Moieties onto the 3-chloropropyltrihydroxysilane coating generates a self-decontaminating surface.

Procedure

Put on sterile gloves.

Prepare the test coupons by wiping them first with ISP Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

Prepare Organosilane Dilution for 3-Chloropropyltrimethoxy Silane

Prepare a 10% solution of 3-chloropropyltrimethoxysilane in Methanol (MeOH) (10 ml. silane in 100 ml. MeOH).

Prepare Triethanolamine solution as a 10% solution in MeOH.

Combine the triethanolamine solution and 3-chloropropyltrimethoxysilane solution in a 1:1 ratio on a stir plate at room temperature (i.e., 100 ml triethanolamine added to 100 ml 3-chloropropyltrimethoxysilane).

First Coat—3-Chloropropyltrimethoxysilane Application

Add the mixture of triethanolamine and 3-chloropropyltrimethoxysilane to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Rinse spray gun with distilled water prior to applying the Titanium Oxide Moieties (unless using 2 sprayers, one for each product).

Second Coat—the Titanium Oxide Moieties Application

Add the Titanium Oxide Moieties to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example VI

This example discloses various aqueous antimicrobial coating compositions comprising 3-aminopropylsilanetriol homopolymers, wherein the compositions optionally include triethanolamine. The compositions were coated onto various test coupons and evaluated for residual antimicrobial efficacy and rinse and abrasion durability.

The reagents used to prepare the antimicrobial coating compositions included 3-APTES from Sigma-Aldrich, 99% purity, Cat #: 440140-500ML (CAS #919-30-2), and triethanolamine from Sigma-Aldrich, 99% purity, Cat #: 90279-500ML (CAS #102-71-6). Triethanolamine may be abbreviated herein as "TEA" or "A01." Compositions made by diluting 3-APTES are referred to herein as "2030" compositions. The shorthand notation "2030-A01" indicates a coating composition made from 3-APTES and triethanolamine. The shorthand notation "2030-A01-T" indicates a method of forming an antimicrobial coating comprising disposing a solution of 2030-A01 on a surface followed by an aqueous solution of titanium sol.

All compositions were made and stored in high-density polyethylene (HDPE) bottles.

Figure 21:
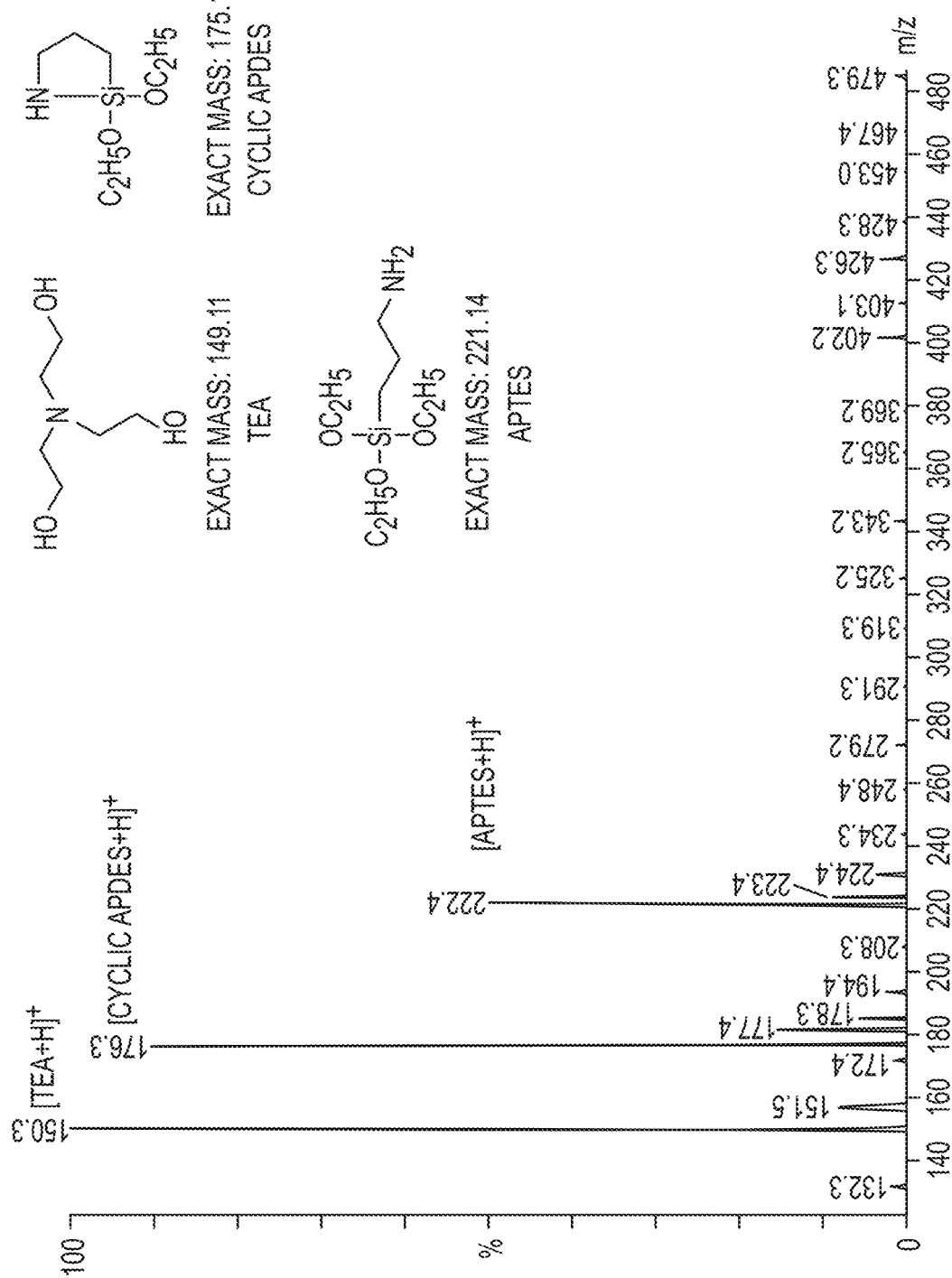
FIG. 21 shows an ESI-mass spectrum of starting materials triethanolamine and 3-aminopropyltriethoxysilane (3-APTES). The mass spectrum also shows a cyclic component, cyclic APDES.

FIG. 21 shows an ESI-Mass Spectrum (MS) of 3-APTES and TEA in anhydrous ethanol, confirming the integrity of the starting materials prior to formulation and providing a control as to where starting material peaks would be found in a mass spectrum of a mixture. The anhydrous ethanol carrier prevents hydrolysis of the 3-APTES. The MS shows three major peaks, namely [3-APTES+H]$^+$ (3-APTES exact mass=221.14), [TEA+H]$^+$ (TEA exact mass=149.11); and a cyclized material [APDES+H]$^+$ (APDES exact mass=175.10), believed to have the following chemical structure:

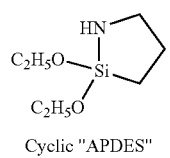

Cyclic "APDES"

Table 21 below sets forth four (4) different antimicrobial coating compositions in accordance to the present disclosure. All entries reflect wt. % actives, based on the total weight of the composition, and the compositions thus recited are "as made," recognizing 3-APTES hydrolyzes and self-condenses into a distribution of 3-aminopropylsilanetriol homopolymers in solution. These examples are in no way meant to be limiting as to the scope of the disclosure. Other compositions may comprise mixtures of organosilanes, each organosilane species providing its own homopolymer distribution in aqueous solution.

TABLE 21

| 3-aminopropylsilanetriol homopolymer antimicrobial coating compositions | | | | |
|---|---|---|---|---|
| Ingredients (Wt. % Actives) | 1 $(2030_5)$ | 2 $(2030_5A01_5)$ | 3 $(2030_5A01_{0.14})$ | 4 $(2030_{10}A01_{0.28})$ |
| 3-APTES | 4.70 | 4.67 | 4.69 | 9.41 |
| TEA | — | 5.54 | 0.16 | 0.31 |
| Deionized water | 95.30 | 89.79 | 95.15 | 90.28 |
| Total | 100.00 | 100.00 | 100.00 | 100.00 |

After mixing and at ambient, compositions 1-4 in Table 21 were clear, colorless and odorless. These physical characteristics did not change for these compositions over the course of 2-years ambient storage.

Figure 22:
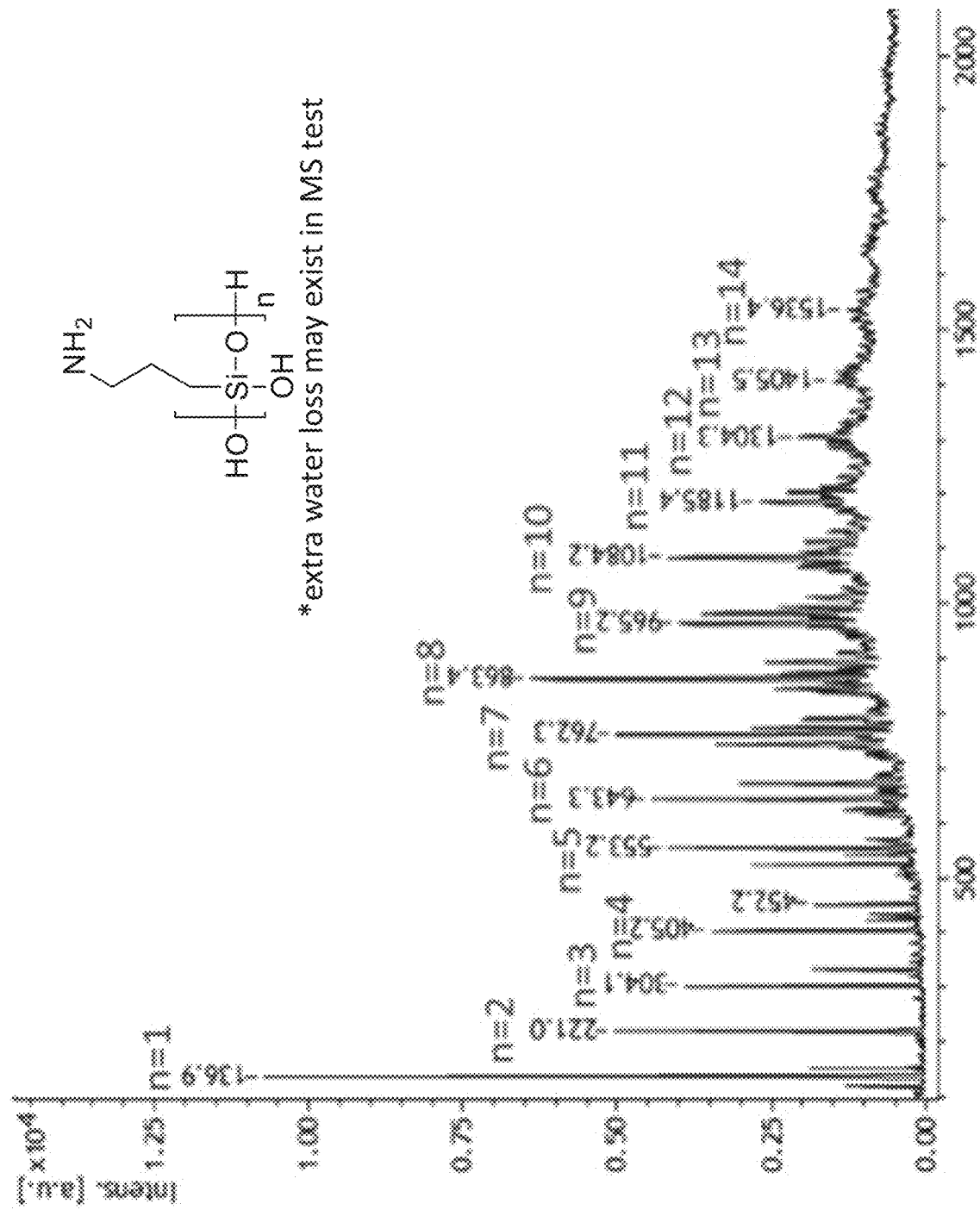
FIG. 22 shows a MALDI-TOF mass spectrum of an aqueous solution of 3-aminopropylsilanetriol homopolymer with an observed chain length distribution from monomer up to about a 14-mer.

FIG. 22 shows a MALDI-TOF Mass Spectrum of composition 1 from Table 21. The MS shows presence of a distribution of homopolymer chain lengths in solution, consisting of monomer (n=1) up to about a 14-mer (n=14) homopolymer. The peak heights may not necessarily correlate to the relative amounts of each species, and therefore no assumptions are made as to the wt. % of each component present in the observed distribution. As indicated by the insert in FIG. 22, additional water loss from each homopolymer, producing the clusters of peaks seen for each homopolymer, may be a consequence of the MS analysis.

Figure 23:
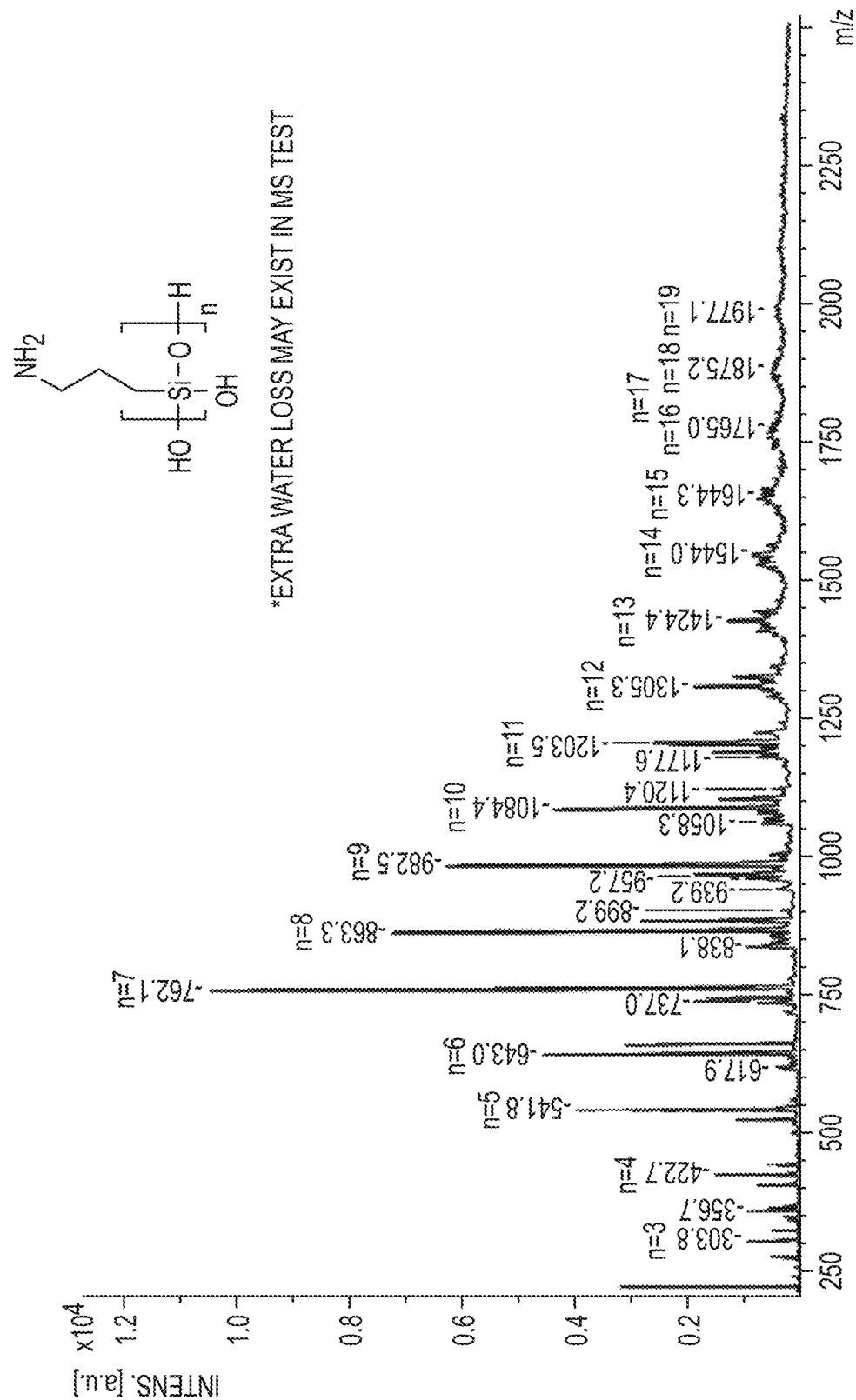
FIG. 23 shows a MALDI-TOF mass spectrum of an aqueous solution of 3-aminopropylsilanetriol homopolymer with an observed chain length distribution from trimer up to about a 19-mer.

FIG. 23 shows a MALDI-TOF Mass Spectrum of composition 4 from Table 21. This MS shows presence of a distribution of homopolymer chain lengths in solution, consisting of 3-aminopropysilanetriol trimer (n=3) up to about a 19-mer (n=19) 3-aminopropysilanetriol homopolymer. As discussed below, variations of the MALDI-TOF analysis reveals additional chain lengths not visible in the MS of FIG. 23. It is believed the presence of triethanolamine alters the chain length distribution formed in solution, i.e., loss of the dimer.

Figure 24:
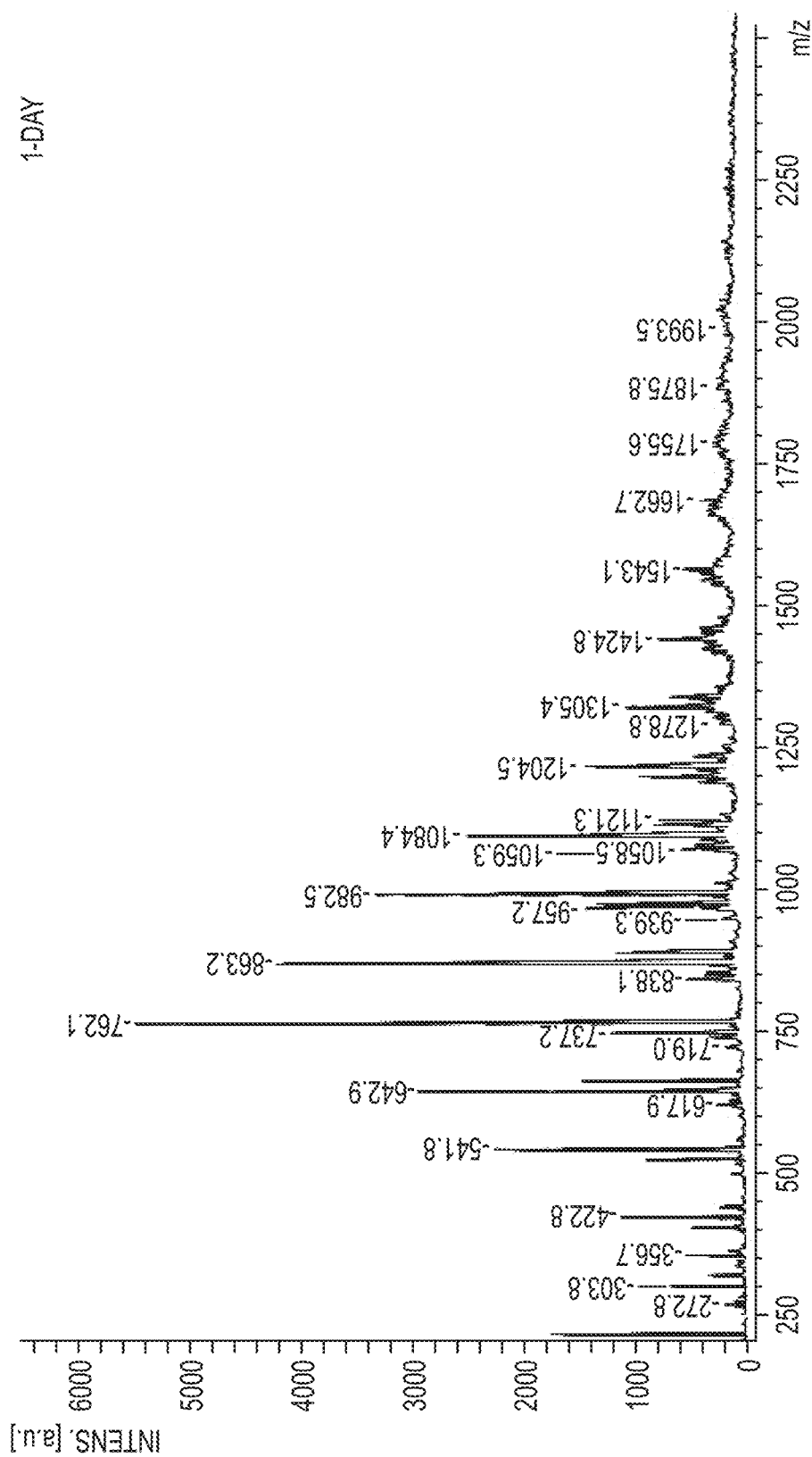
FIGS. 24-27 show time sequential MALDI-TOF mass spectrums of an aqueous solution of 3-aminopropylsilanetriol homopolymer over 1-day, 1-month, 6-months and 1-year, demonstrating the remarkable stability of the distribution of homopolymers.
Figure 25:
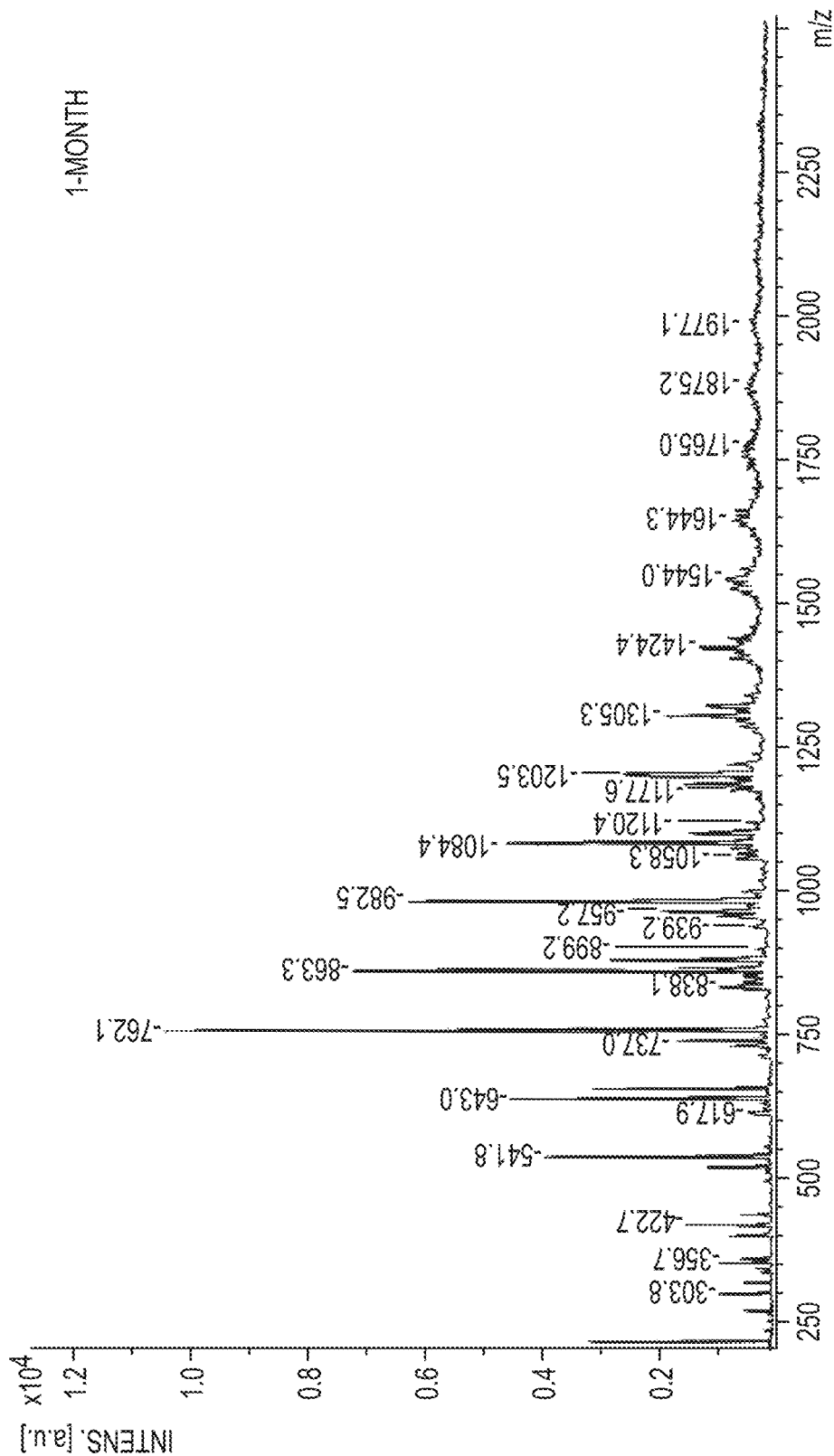
Figure 26:
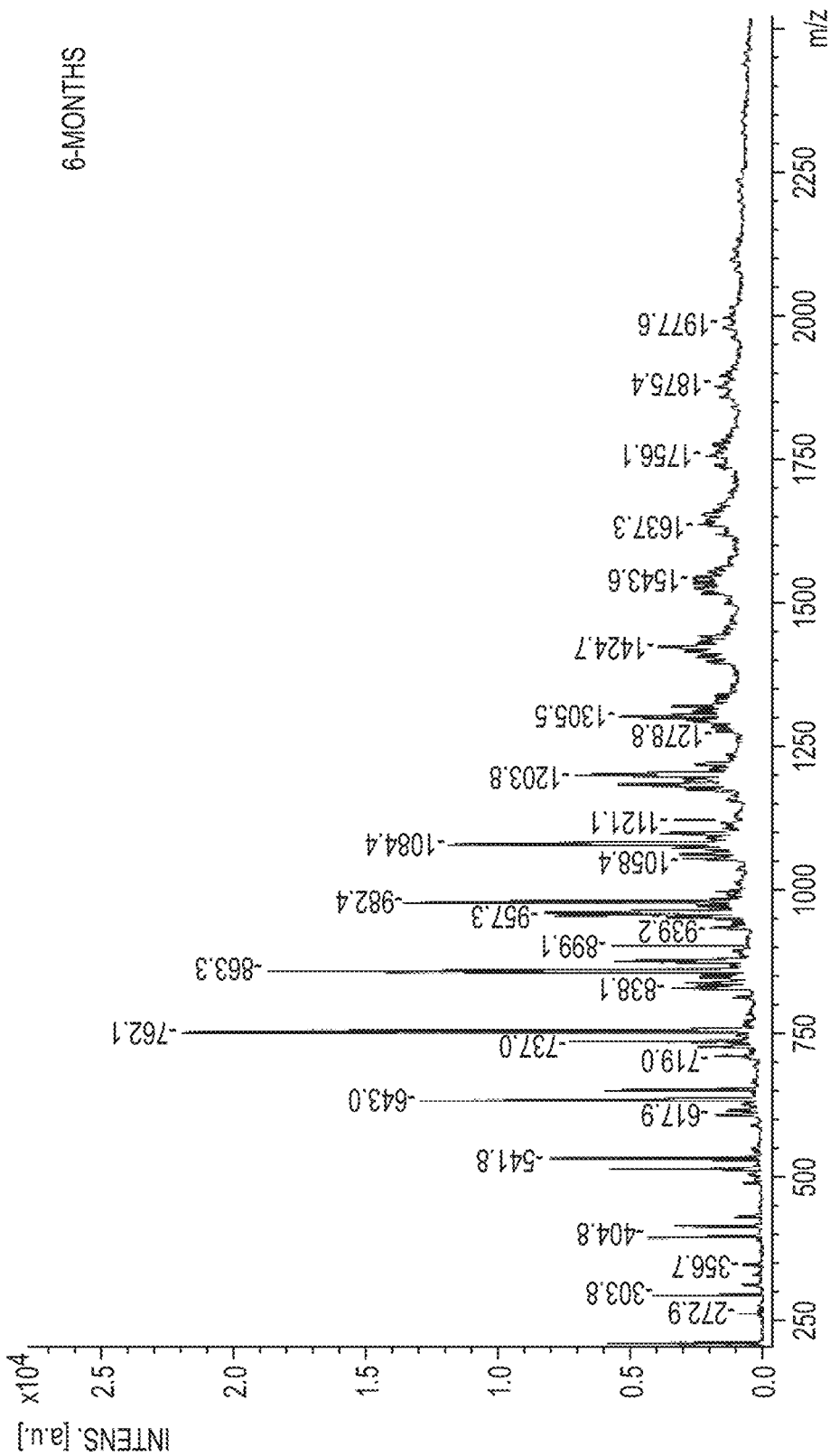
Figure 27:
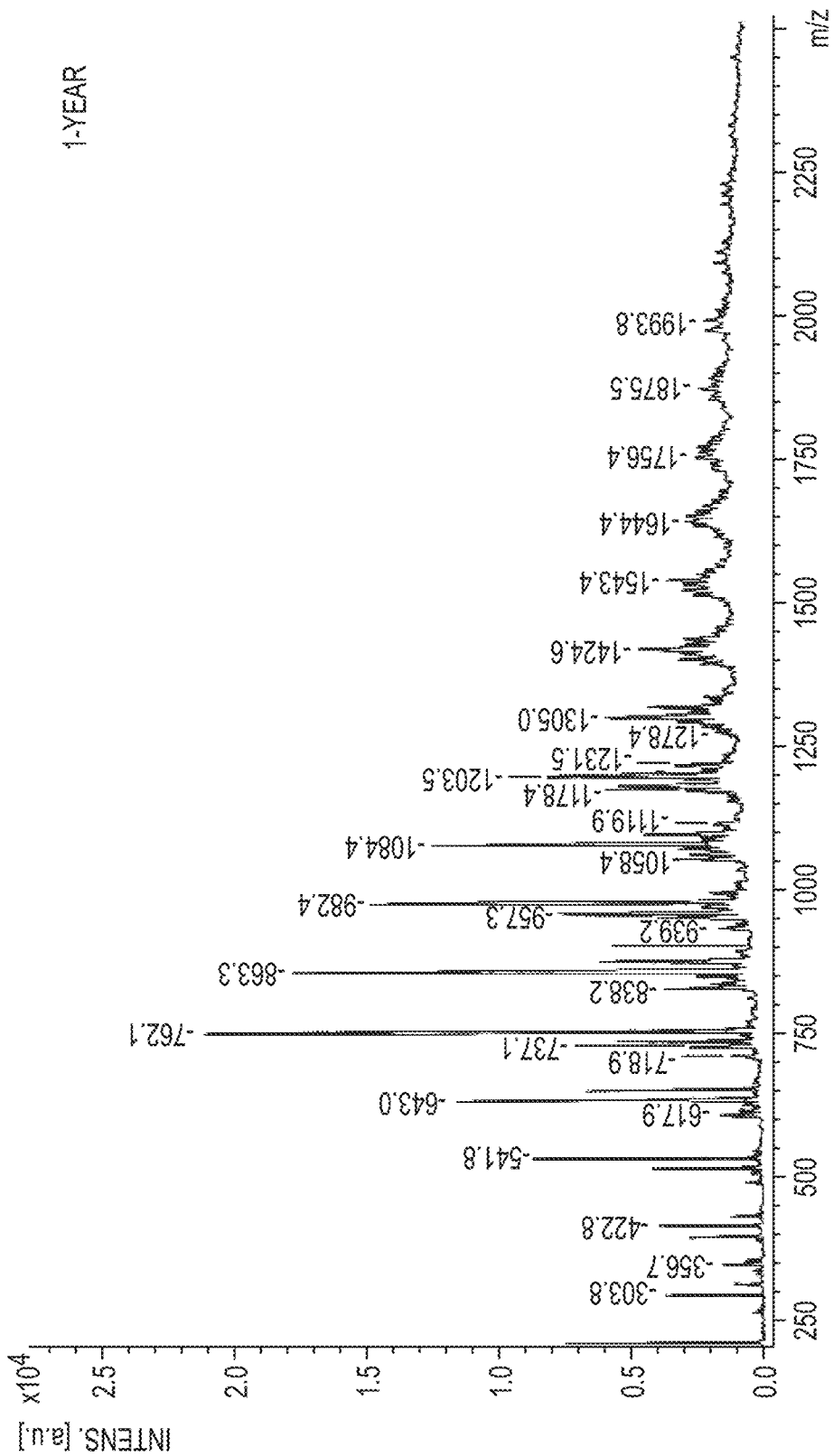

FIGS. 24-27 show MALDI-TOF Mass Spectrums of composition 4 from Table 21 at different time periods, evidencing the remarkable solution storage stability at room temperature for the 3-aminopropysilanetriol homopolymers. FIG. 24 shows the mass spectrum of 1-day old composition 4. FIG. 25 shows the mass spectrum of 1-month old composition 4. FIG. 26 shows the mass spectrum of 6-month old composition 4. FIG. 27 shows the mass spectrum of 1-year old composition 4. FIGS. 24-27 show substantially identical mass spectra, confirming that the chain length distribution of 3-aminopropysilanetriol homopolymers, wherein n=3 to about 19, remains reliably stable in aqueous solution.

Figure 28:
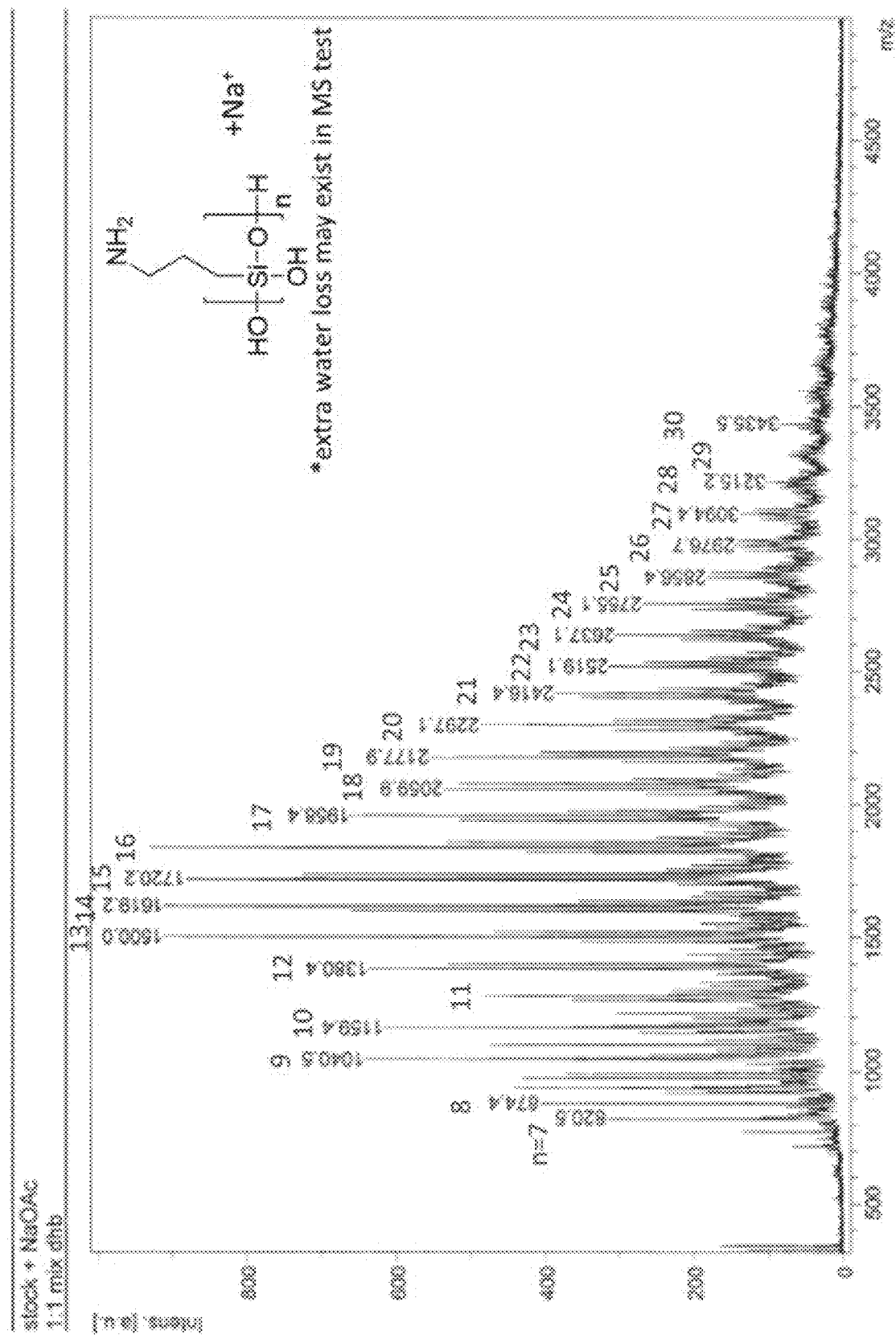
FIG. 28 shows a MALDI-TOF mass spectrum of 3-aminopropylsilanetriol homopolymer where the solution was treated with sodium acetate in order to visualize longer chain lengths. The mass spectrum indicates a chain length distribution of from about a 7-mer up to about a 30-mer.

FIG. 28 sets forth a MALDI-TOF Mass Spectrum of composition 4 from Table 21 wherein sodium acetate was added to the test sample, followed by 2,5-dihydroxybenzoic acid. The spectrum verifies the presence of additional homopolymer chain lengths, with this spectrum indicating a homopolymer distribution of n=7 to about n=30. Addition of sodium acetate facilitates detection of the higher chain lengths present in the composition but not detectable otherwise. Viewing the several mass spectra in combination, it is concluded that composition 4 from Table 21 comprises 3-aminopropysilanetriol homopolymers having a chain length distribution of n=3 to about 30, wherein the presence of triethanolamine in the composition has prevented the dimer from remaining in solution.

Figure 29A:
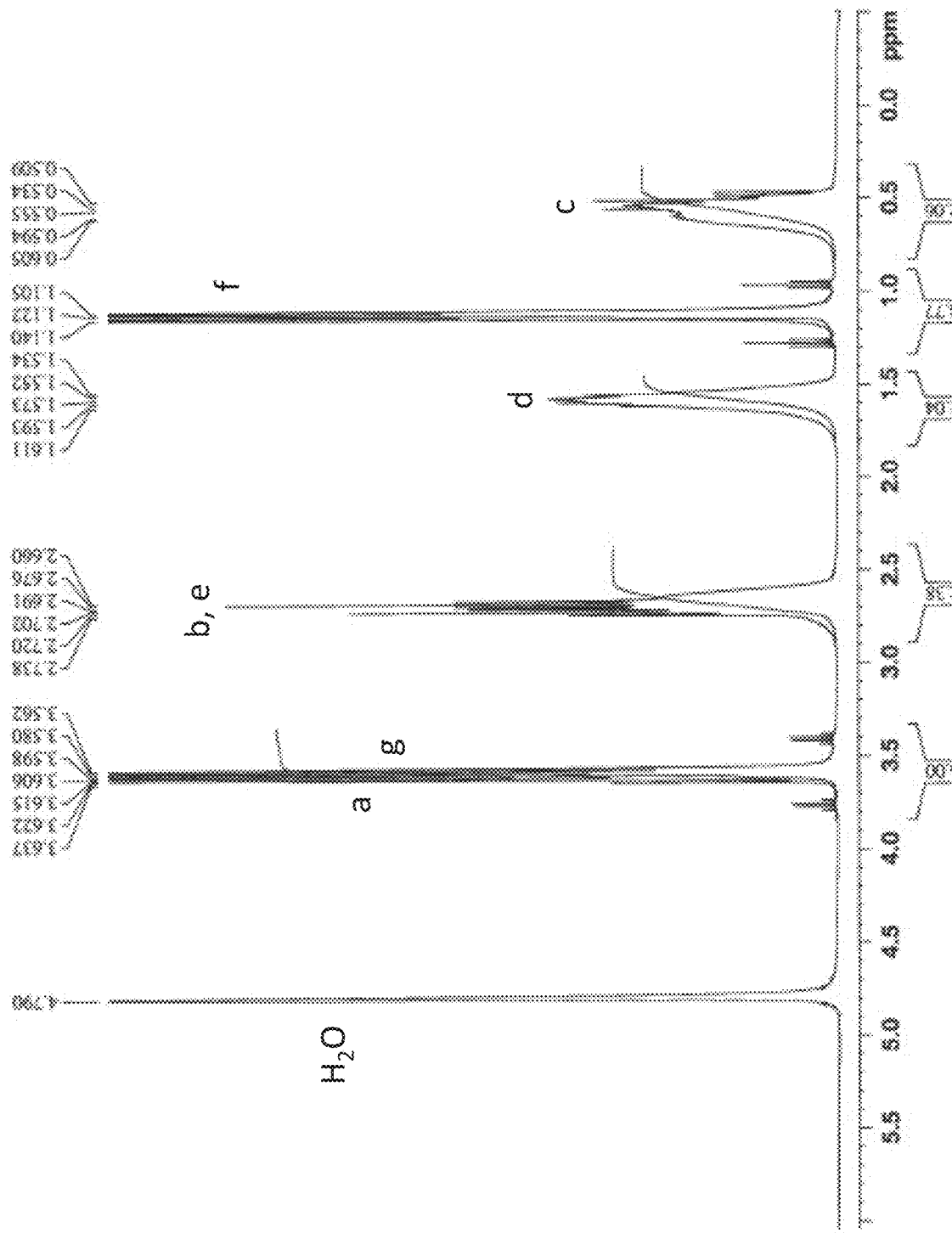
FIG. 29A shows a $^1$H-NMR spectrum of a solution of 3-aminopropylsilanetriol homopolymer and FIG. 29B shows possible peak assignments based on proton proximities.
Figure 29B:
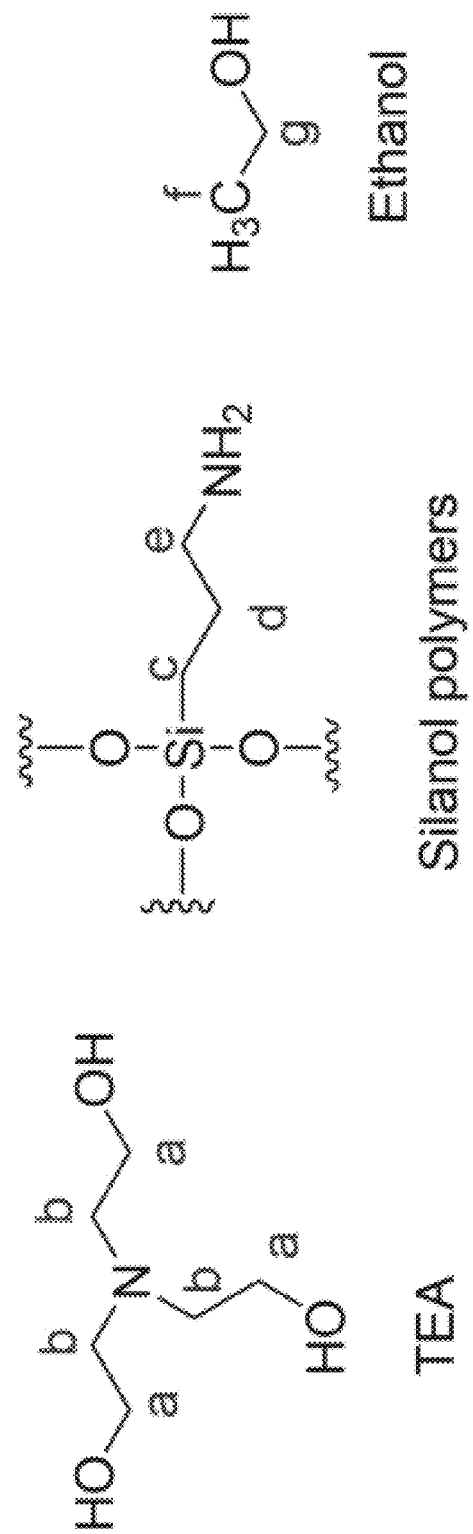

FIGS. 29A and 29B set forth the $^1$H-NMR spectrum (in $D_2O$/400 MHz) and corresponding peak interpretation for composition 4 in Table 21, aged 5-days prior to the analysis. With reference to both figures, $H_b$, $H_c$, $H_d$ and $H_e$ signals are seen as overlapped peaks due to the polymerization of the silanol to homopolymers, and the Ha signal is masked in the peaks of $H_g$ from ethanol liberated by hydrolysis of 3-APTES into 3-aminopropysilanetriol.

Figure 30A:
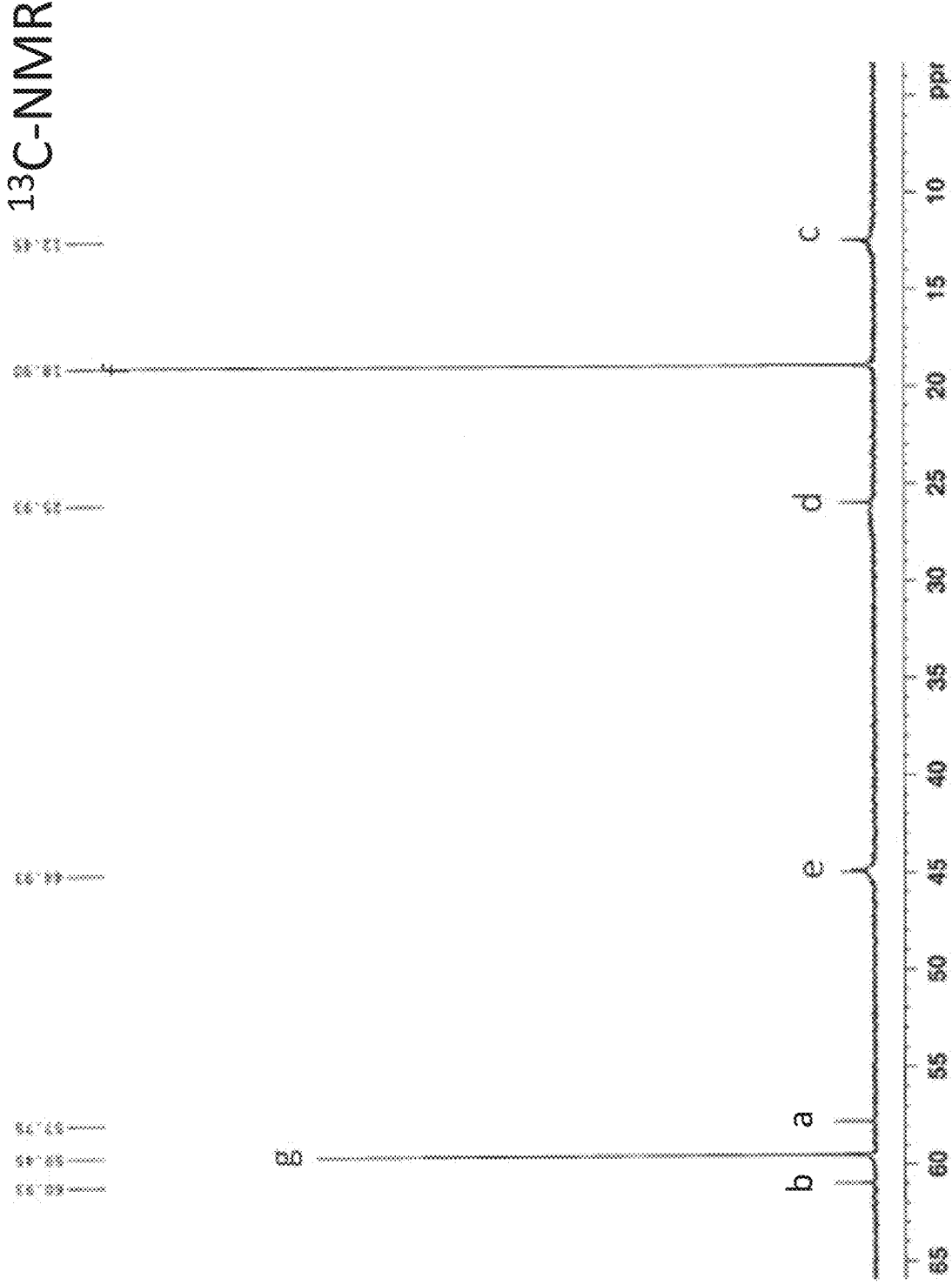
Figure 30B:
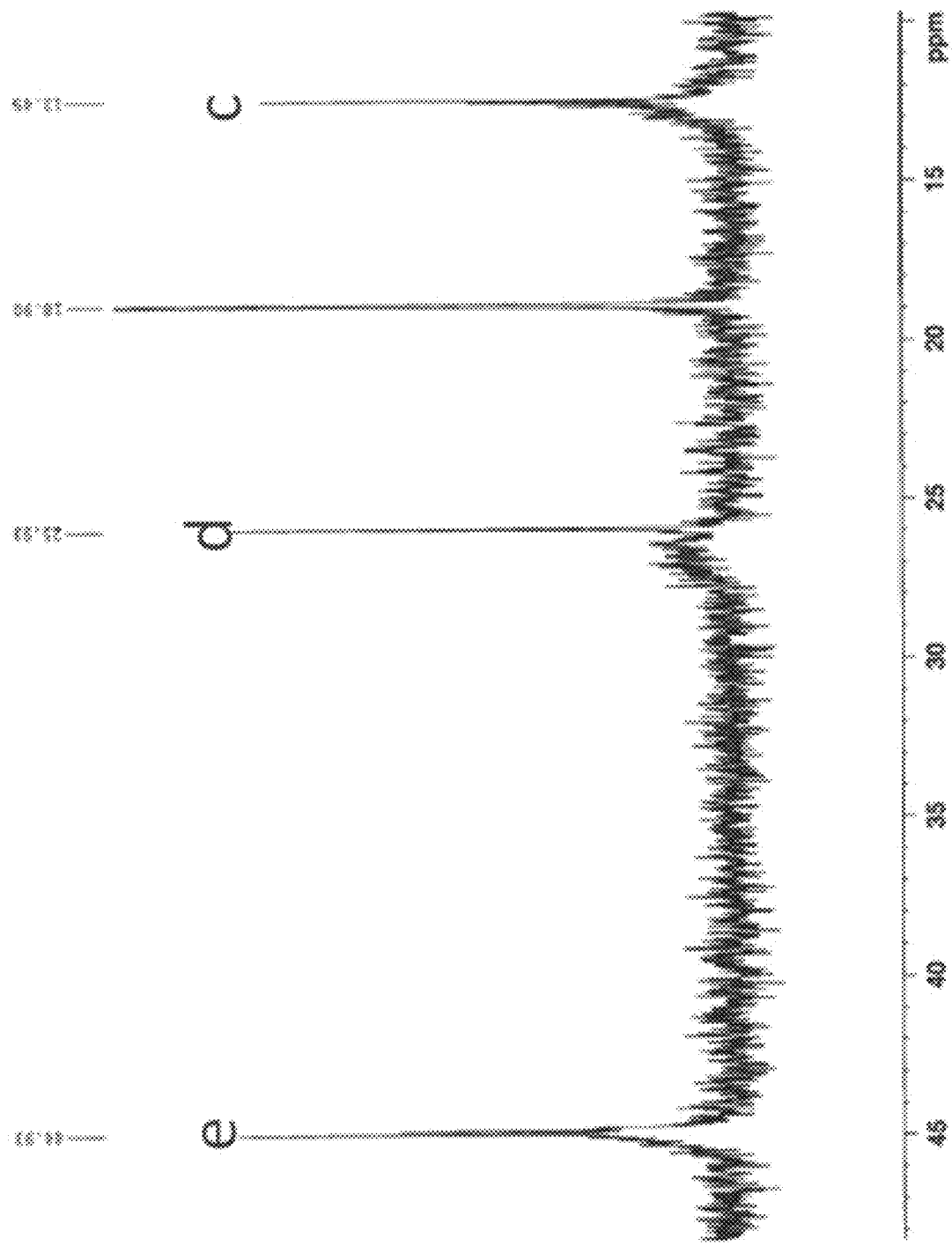

FIGS. 30A, 30B and 30C set forth a $^{13}$C-NMR spectrum (in $D_2O$/400 MHz) and corresponding peak interpretation for composition 4 in Table 21. With reference to FIGS. 30B and 30C, the $C_c$, $C_d$ and $C_e$ signals are seen as broadened peaks due to crosslinking strands of silanol polymers.

Figure 31:
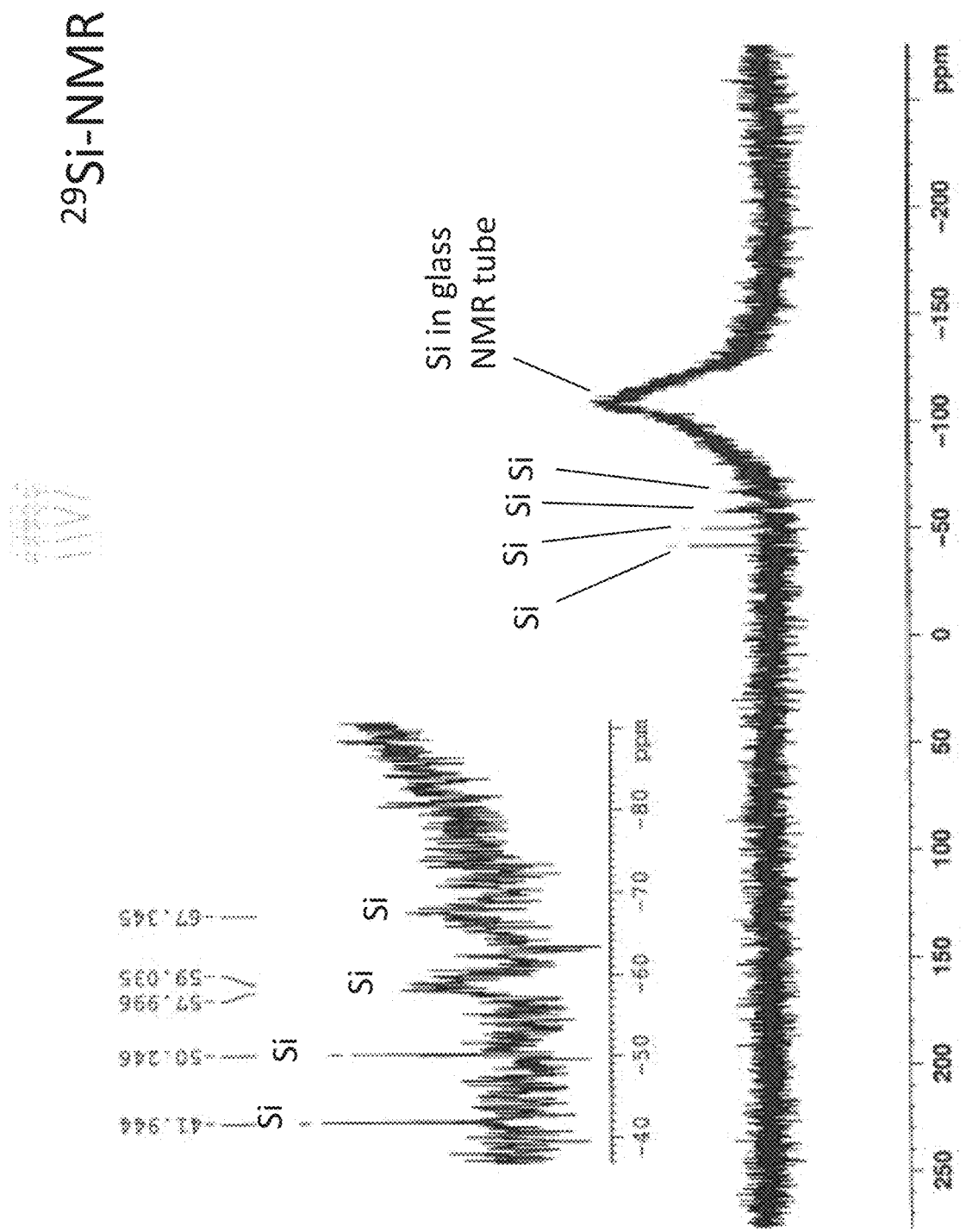
FIG. 31 sets forth a $^{29}$Si-NMR spectrum of a solution of 3-aminopropylsilanetriol homopolymer.

FIG. 31 sets forth a $^{29}$Si-NMR spectrum (in $D_2O$). The Si signals are seen as multiple peaks due to crosslinking strands of silanol polymers.

Figure 32A:
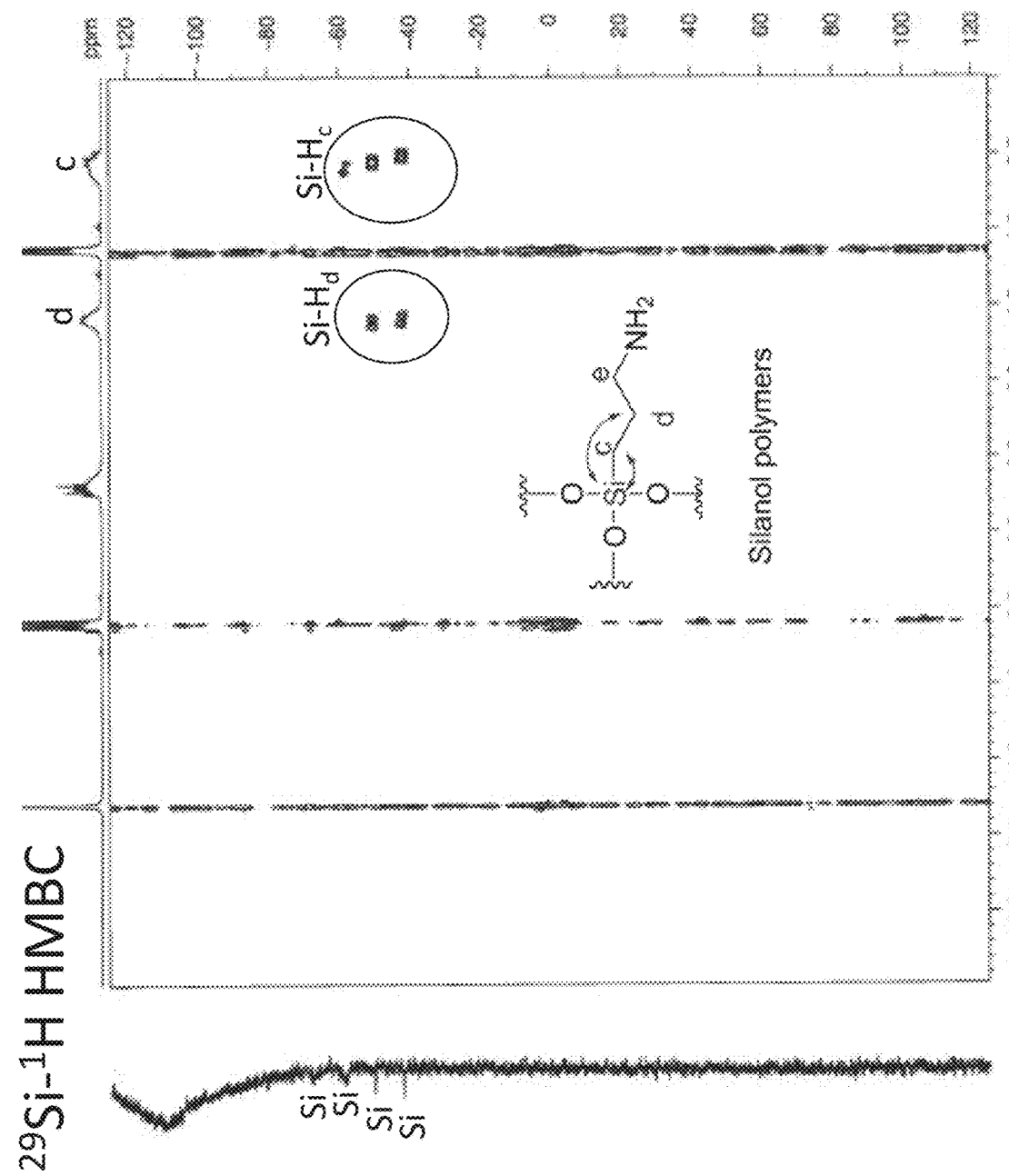
FIGS. 32A and 32B show a $^{29}$Si—$^1$H-HMBC spectrum of a solution of 3-aminopropylsilanetriol homopolymer.
Figure 32B:
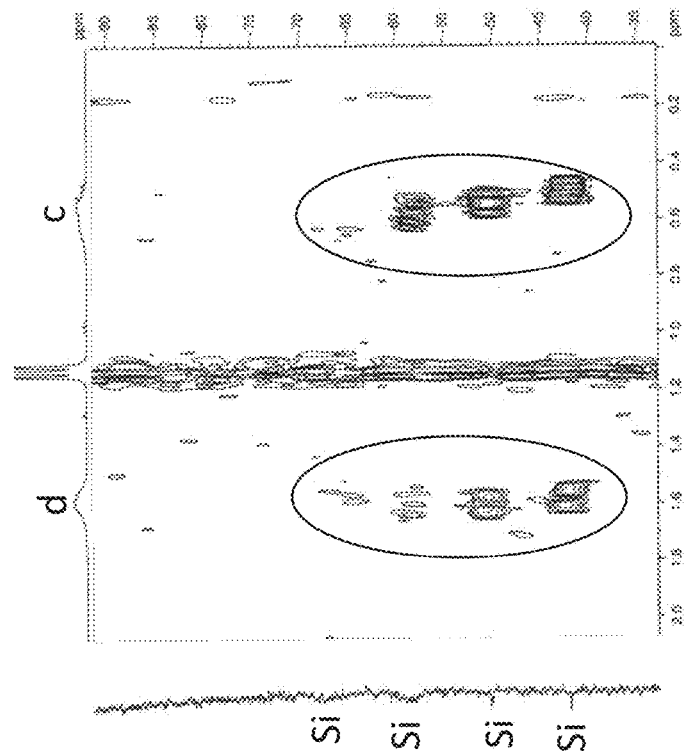

FIGS. 32A and 32B set forth a $^{29}$Si—$^1$H Heteronuclear Multiple Bond Correlation (HMBC) for composition 4 in Table 21. The Si—H signals are seen as coupled cross peaks due to crosslinking strands of silanol polymers.

Figure 33:
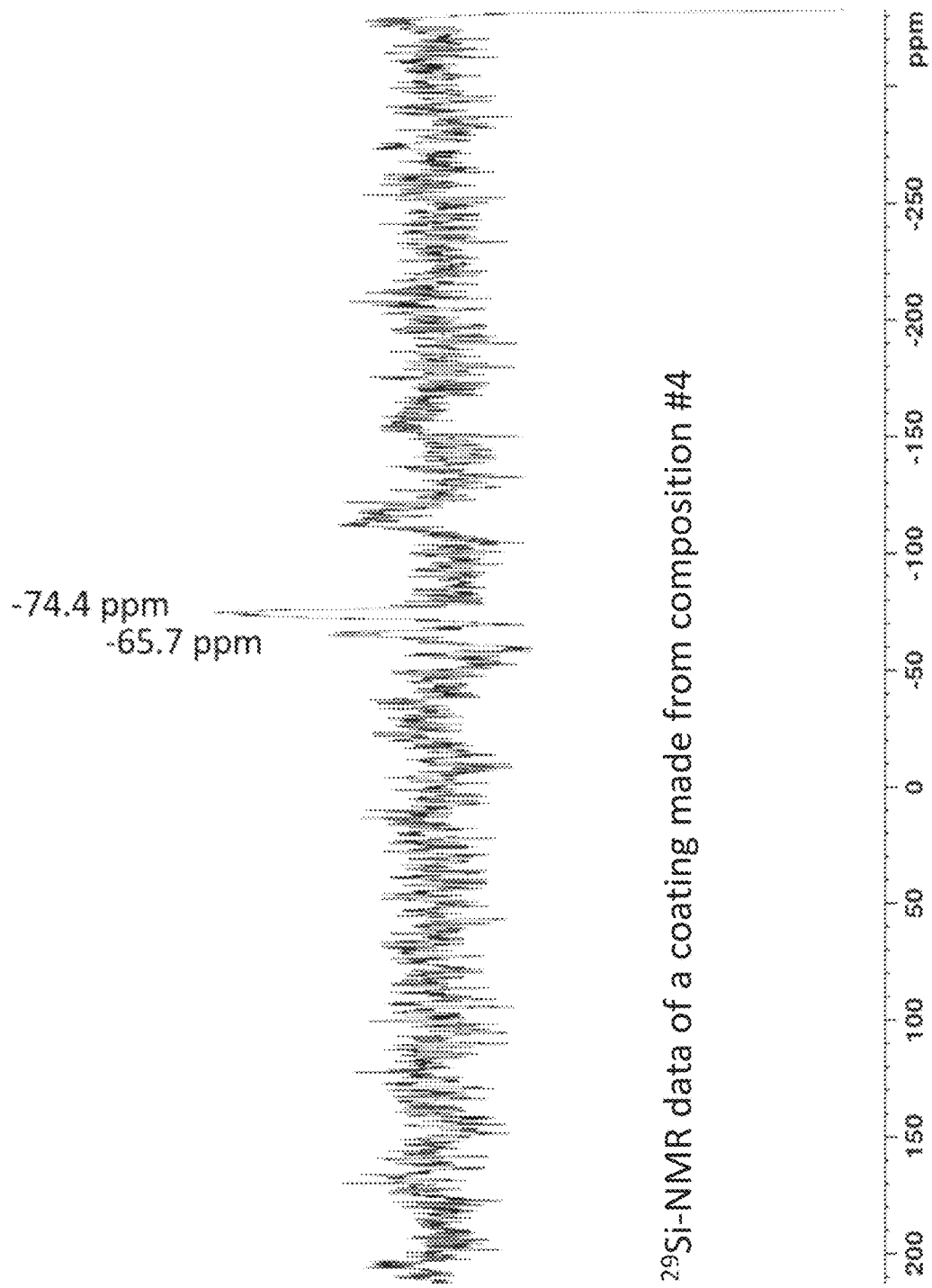
FIG. 33 shows a $^{29}$Si-NMR spectrum of a solution obtained by partially dissolving a nearly intractable antimicrobial coating comprising further polymerized and/or crosslinked 3-aminopropylsilanetriol homopolymer scraped from a surface.
Figure 34:
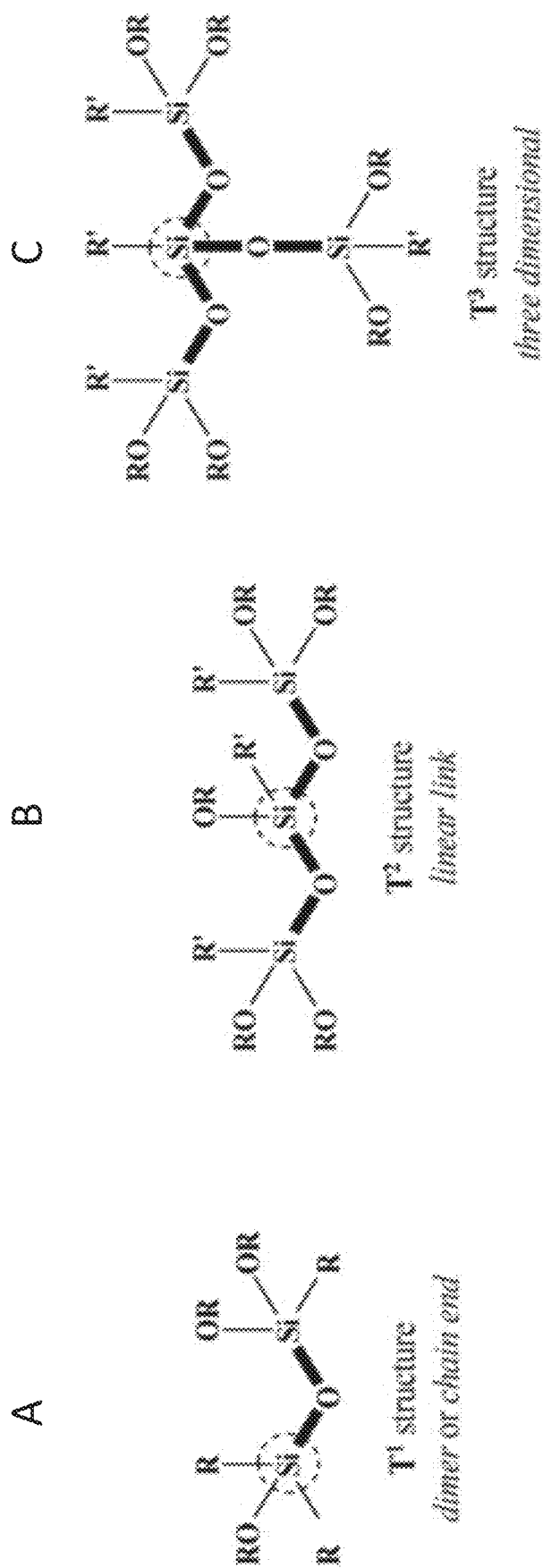
FIG. 34 sets forth possible structural explanations behind the further polymerized and/or crosslinked coatings comprising 3-aminopropylsilanetriol homopolymer.

FIG. 33 sets forth a $^{29}$Si-NMR spectrum (in $D_2O$) of a coating made from composition #4 in Table 21. To obtain this spectrum, a substantially thick coating of composition #4 was dried on a glass surface. After drying, the thick transparent film was scraped off with a spatula and the resulting whitish scrapings ground into a fine white powder consisting of 3-aminopropysilanetriol homopolymer. 100 mg of the powder was dissolved in each of 0.5 mL methanol-$d_4$ and 0.5 mL $D_2O$. However, the dried 3-aminopropysilanetriol homopolymers showed poor solubility in both methanol-$d_4$ and $D_2O$, which likely indicates further Si—OH polymerization and/or crosslinking during the concentration and drying of the composition on the surface. Although the solubility was low, longer acquisition time allowed capture of a spectrum in $D_2O$. As shown in FIG. 34, the $^{29}$Si-NMR spectrum of FIG. 33 suggests a major presence of $T^3$ type siloxanes (C) (compared to $T^0$, $T^1$ (A) and $T^2$ (B) silicon atoms present in the organosilane in solution prior to application on the surface). These data suggest a higher degree of polymerization of 3-aminopropysilanetriol in the dried coating compared to the degree of polymerization of 3-aminopropysilanetriol seen in the antimicrobial coating composition prior to use.

Figure 35:
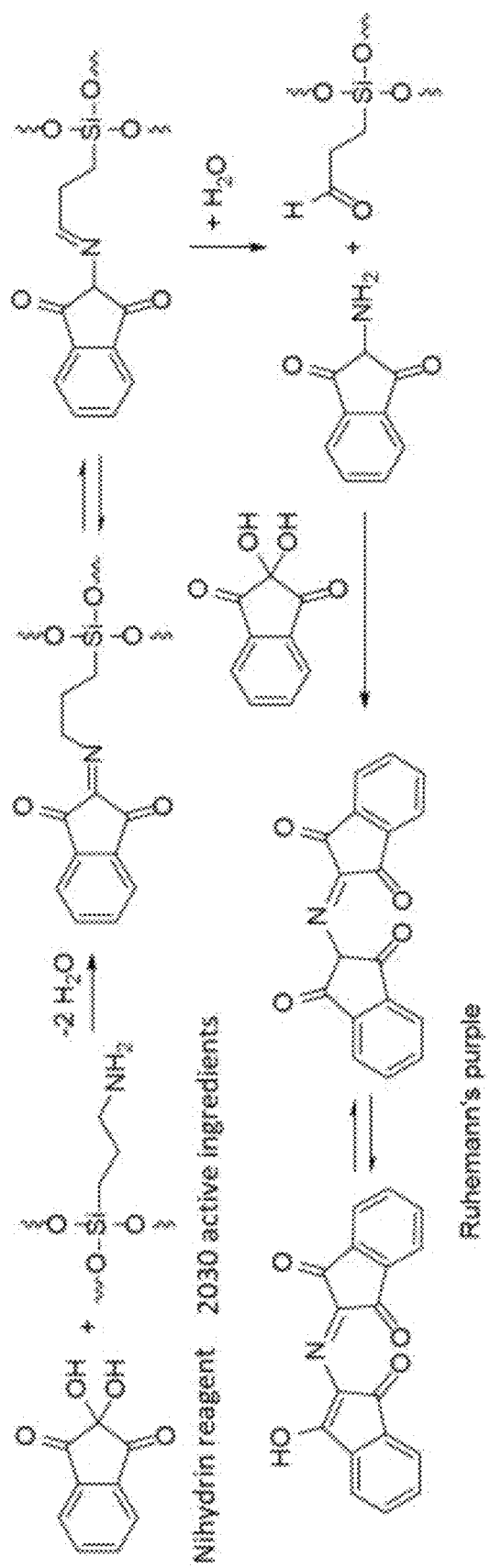
FIG. 35 sets forth a chemical reaction scheme wherein 3-aminopropylsilanetriol homopolymer reacts with ninhydrin to form a color indicator that can be quantified.

FIG. 35 sets forth the reaction between ninhydrin and 3-aminopropysilanetriol homopolymers that generates the indicating dye known as "Ruhemann's Purple." Ninhydrin is a sensitive reagent for detection and quantification of compounds containing primary amino groups. Triethanolamine, being a tertiary amine, does not react with ninhydrin. Ninhydrin cannot distinguish between 3-aminopropysilanetriol homologs, but instead reacts indiscriminately with any and all primary amino groups when provided in excess.

Figure 36:
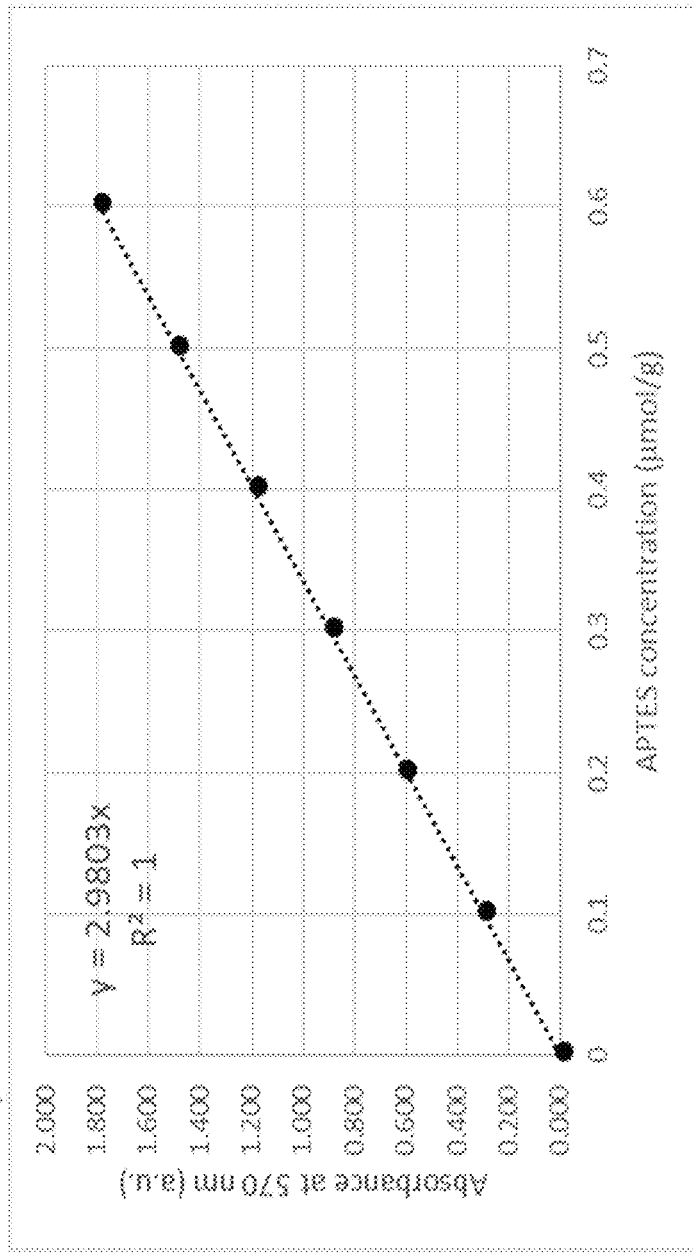
FIG. 36 sets forth a standard curve of absorbance at 570 nm versus concentration of 3-aminopropylsilanetriol homopolymer obtained by reacting known concentrations of organosilane with ninhydrin and measuring the absorbance of the purple color thus developed.

FIG. 36 sets forth a standard curve and tabular summary of absorbance versus 3-APTES concentration, generated by reacting various concentrations 3-APTES with ninhydrin and measuring the absorbance of the purple dye generated. The standard curve thus obtained exhibited remarkable linearity, with $R^2$=1. This standard curve can be used to interpolate unknown concentrations of 3-aminopropylsilanetriol homopolymers in solution given an absorbance measure, or by using the equation y=2.9803x.

Antimicrobial Efficacy and Abrasion/Rinse Durability of Coatings—General Procedures Notations and Definitions Aqueous antimicrobial coating compositions in accordance with the present disclosure were used to form antimicrobial coatings on test coupons made of various materials. The coated coupons were then used in residual antimicrobial efficacy testing and durability testing that included rinse testing and mechanical abrasion testing. In these tests, small coupons of stainless steel or Formica® (i.e., paper and melamine laminate) were used as indicated. The coupons may also be referred to as "carriers." For uniform coating, the test coupons for a particular test can be arranged in an array so that many coupons can be coated in the same process. Test coupons were first washed with hand dishwashing detergent (Palmolive®, from Colgate Palmolive Company) in warm water and rinsed with copious amounts of water. After ambient drying, the coupons were wiped with GreenKleen® 420-4 (from IndusCo®, Inc.), unless a particular test indicates otherwise by having the designation "No GK."

Internal designations, shorthand codes, are used herein for convenience. the internal reference coding system includes a silane indicator, wherein "2030" indicates 3-APTES in a composition that generates 3-aminopropylsilanetriol homopolymers in solution, an amine indicator wherein "A01" (or in some instances, "TEA") indicates triethanolamine in the antimicrobial coating composition, and a titanium coating indicator "T," which, when present, indicates a second coating step using a titanyl sol-gel comprising an 0.85 wt. % aqueous mixture of peroxotitanium acid and peroxo-modified anatase sol as discussed. Thus, for example, the shorthand code of "2030A01T," refers to a test coupon that was sequentially coated with (1) an aqueous mixture of 3-aminopropylsilanetriol homopolymer (2030) and triethanolamine (A01); followed by (2) a titanyl sol-gel (T) comprising 0.85 wt. % aqueous mixture of peroxotitanium acid and peroxo-modified anatase sol.

In any experiment that included "T," the aqueous 0.85 wt. % peroxotitanium acid and peroxo-modified anatase sol mixture was sprayed overtop of the organosilane homopolymer coating such that the portion of the surface being testing for durability and/or antimicrobial efficacy comprises both coatings, the organosilane homopolymers and the titanyl species. As mentioned, room temperature drying of the aqueous 0.85 wt. % peroxotitanium acid and peroxo-modified anatase sol mixture may form a crystalline or amorphous $TiO_2$ thin film.

As used herein, the designation "$2030_5$" refers to an aqueous antimicrobial coating composition made by diluting 5 mL 3-APTES (4.7 wt. % or 5 vol. % actives) in water without triethanolamine. Thus, composition 1 in Table 21 may be referred to as "$2030_5$" throughout the studies for convenience. A "T" following this shorthand designation indicates the test coupons for the particular study were also coated with the 0.85 wt. % aqueous titanium sol composition in a two-step coating process as discussed.

As used herein, the designation "$2030_{10}$" refers to an aqueous antimicrobial coating composition made by diluting 10 mL 3-APTES (9.4 wt. % or 10 vol. % actives) in water without triethanolamine. A "T" following this shorthand designation indicates the test coupons for the particular study were also coated with the 0.85 wt. % aqueous titanium sol composition in a two-step coating process as discussed.

As used herein, the designation "$2030_5A01_5$" refers to an aqueous antimicrobial coating composition made from 4.67 wt. % or 5 vol. % actives 3-APTES and 5.54 wt. % or 5 vol. % actives triethanolamine in water. Thus, composition 2 in Table 21 may be referred to as "$2030_5A01_5$" throughout the studies for convenience. A "T" following this shorthand designation indicates the test coupons for the particular study were also coated with the 0.85 wt. % aqueous titanium sol composition in a two-step coating process as discussed.

As used herein, the designation "$2030_5A01_{0.14}$" refers to an aqueous antimicrobial coating composition made from 4.69 wt. % or 5 vol. % actives 3-APTES and 0.16 wt. % or 0.14 vol. % actives triethanolamine in water. Thus, composition 3 in Table 21 may be referred to as "$2030_5A01_{0.14}$" throughout the studies for convenience. A "T" following this shorthand designation indicates the test coupons for the particular study were also coated with the 0.85 wt. % aqueous titanium sol composition in a two-step coating process as discussed.

As used herein, the designation "$2030_{10}A01_{0.28}$" refers to an aqueous antimicrobial coating composition made from 9.41 wt. % or 10 vol. % actives 3-APTES and 0.31 wt. % or 0.28 vol. % actives triethanolamine in water. Thus, composition 4 in Table 21 may be referred to as "$2030_{10}A01_{0.28}$" throughout the studies for convenience. A "T" following this shorthand designation indicates the test coupons for the particular study were also coated with the 0.85 wt. % aqueous titanium sol composition in a two-step coating process as discussed.

Coating Test Coupons with Antimicrobial Coating Compositions

The single-step coating procedure (aqueous organosilane homopolymer solution only and no subsequent step of applying titanyl species "T") comprised spraying the aqueous organosilane homopolymer mixture as a fine mist from an electrostatic spray gun at a distance of about 5-6 feet onto the test coupons and allowing the surfaces to dry at room temperature overnight.

The two-step coating procedure (aqueous organosilane homopolymer solution followed by aqueous 0.85 wt. % peroxotitanium acid and peroxo-modified anatase sol mixture "T") comprised spraying the aqueous organosilane homopolymer mixture as a fine mist from an electrostatic spray gun at a distance of about 5-6 feet onto the test coupons and allowing the surfaces to visibly dry at ambient conditions for about 3 to 5 minutes. The test coupons were then subsequently coated by aqueous 0.85 wt. % peroxotitanium acid and peroxo-modified anatase sol mixture from an electrostatic sprayer at a distance of 5 to 6 feet and the resulting coated surfaces allowed to dry overnight at room temperature.

Abrasion Testing (Durability Against Mechanical Abrasion)

Testing results further includes wear data for the various antimicrobial coatings comprising aqueous organosilane homopolymer composition with and without optional amine. Wear data are indicative of the durability of a coating and correlate to how well an antimicrobial coating on a surface can withstand frequent handling or other insult. An existing EPA Protocol may be used to generate the wear data. In certain instances, the EPA protocol may be modified.

EPA Protocol #01-1A, entitled "Protocol for Residual Self-Sanitizing Activity of Dried Chemical Residues on Hard, Non-Porous Surfaces," is a standard test method used for testing the durability of an antimicrobial coating on a hard surface. The test method utilizes an in-line abrasion machine commonly used in assessing the cleaning ability of detergents. However, instead of a soiled tile being positioned in the machine to be scrubbed, test coupons having an antimicrobial coating are positioned in the machine. The back-and-forth cycling of a weighted scrubber (a weighted "boat" with a cloth or sponge) simulates natural wearing of the antimicrobial coating, such as the wear the surface may experience when frequently handled. In variations of the test protocol, the cloth in the weighted boat may be moist to simulate the handling of surfaces with a moist hand or a wipe. In various examples, correlations can be made to handling of environmental surfaces, e.g., a doorknob. At various wear cycles, coupons may be weighed for weight loss or inoculated with a test organism.

The abrasion tester suggested in the EPA protocol is a GardCo® Washability and Wear Tester, Model D10V, Cat. No. #WA-2153, from the Paul N. Gardner Co., Inc., Pompano Beach, Fla., which is the machine used herein. Variables in the protocol include the weight of the boat, the material wrapped around the boat (e.g., a cloth wiper), the moisture level on the wiper, the speed of the oscillations, and the number of cycles, in addition to the type of coating on the test coupons, the test coupon material, and the arrangement of coated coupons in the machine.

Abrasion Testing Protocol

1. Six 2"×2" stainless steel (SS), paper and melamine laminate (Formica®), or other material test coupons ("carriers") were used, each coupon weighed before and after coating, and before and after abrasion testing.

2. The wear testing was performed in replicates of two.

3. TexWipe® cotton wipers (VWR #TWTX309) were used with TexWipe® FoamWipe™ wipers (VWR #TWTX704) as a liner on the weighted boat.

4. The weight of the boat was adjusted to 1.0 kg with the necessary auxiliary weights.

5. Using the GardCo® Washability machine, a cycle refers to 2 passes of the weighted boat, there and back. Abrasion speed was set to "2.5," which equated to about 4-6 seconds per cycle.

6. The cotton wiper and foam liner were arranged in the weighted boat. The wiper was sprayed at a distance of 75 cm±1 cm with deionized water for 2 seconds using a Preval Sprayer to moisturize the wiper. Abrasion testing was performed immediately after moisturizing the wiper.

7. The TexWipe® cotton wiper was replaced after each abrasion cycle.

8. Test coupons subjected to 10 cycles (10×) or 30 cycles (30×) are then measured for percent weight loss or inoculated with a test organism to measure residual antimicrobial efficacy.

Rinse Testing

In some instances, coated test coupons ("carriers") were subjected to a rinse procedure to test resistance of coatings to wetting without any mechanical abrasion. For the rinse testing, coupons were washed three times in 20 mL of deionized water on a shaker at 60 revolutions per minute (rpm) for 10 min.

Surface Time-Kill Testing Procedure with *E. coli* 25922:

1. An overnight culture of the test organism, *E. coli* 25922, was initiated by inoculating one colony from a TSA plate into 20 ml of TSB, and incubating under dynamic conditions at 37° C. for 24 hours prior to testing.

2. On the date of testing, the test culture was removed from incubation, and supplemented with Fetal Bovine Serum (FBS) to achieve a final concentration of 5% (v/v).

3. An overnight density of $10^8$ to $10^9$ colony-forming units (CFU) per ml was assumed. No dilutions of the test organism were performed prior to carrier inoculation. The target inoculum density was $10^6$ to $10^7$ CFU per carrier (or per 0.010 ml).

4. Bacterial inocula (0.010 ml) were pipetted onto the center of the control and test carriers, and spread over a surface area of ~1 $in^2$ using a sterile, bent pipette tip.

5. One set of control and test carriers was harvested/neutralized after a 20 min drying period to determine Time Zero counts. The sterilized swabs were dipped in 1 ml Dey Engley (D/E) Broth for 2 seconds and were used to swab the inoculated surface on control and test carriers, followed by vortexing in the rest of D/E Broth to release the bacteria. Two alternative methods were used for harvesting bacteria as follows: 1. The carriers (e.g. 2"×2" stainless steel coupons) were transferred into individual sterilized stomacher bags containing 10 mL of D/E Broth and then sonicated 20 seconds in an ultra-sonicator cleaner. Then the carriers were placed horizontally on an orbital shaker for 5 min at 250 rpm. The D/E Broth were then transferred to 15 mL conical tubes. 2. The carriers (e.g. 3"×1" glass slides) were transferred into 50 mL conical tubes containing 25 mL D/E Broth, followed by 1-minute vortexing to release the bacteria.

6. The remaining control and test carriers were held under ambient conditions for the duration of each of the specified study contact times of 1 hour and 4 hours and all carriers were evaluated in duplicate.

7. Once the contact times were reached, the control and test carriers were neutralized by D/E Broth, followed by vortexing or shaking as previously described.

8. Control and test carrier eluates were serially diluted (1:10), and spread-plated onto tryptic soy agar (TSA) plates.

9. The plates were inverted and incubated at 37° C. for 18 to 24 hours, and then scored by directly counting the colonies. Bacterial counts were calculated on a "per carrier" basis. A mean bacterial count was then computed per coating formulation per contact time, as applicable.

10. $Log_{10}$ and percent reductions were calculated for each of the test coating formulations relative to the timed control bacterial counts.

Surface Time-Kill Testing Procedure with *S. epidermidis* 12228:

1. An overnight culture of the test organism, *S. epidermidis* 12228, was initiated by inoculating one colony from a TSA plate into 20 ml of TSB, and incubating under dynamic conditions at 37° C. for 24 hours prior to testing.

2. On the date of testing, the test culture was removed from incubation, and supplemented with Fetal Bovine Serum (FBS) to achieve a final concentration of 5% (v/v).

3. An overnight density of $10^8$ to $10^9$ colony-forming units (CFU) per ml was assumed. No dilutions of the test organism were performed prior to carrier inoculation. The target inoculum density was $10^6$ to $10^7$ CFU per carrier (or per 0.010 ml).

4. Bacterial inocula (0.010 ml) were pipetted onto the center of the control and test carriers, and spread over a surface area of ~1 $in^2$ using a sterile, bent pipette tip.

5. One set of control and test carriers was harvested/neutralized after a 20 min drying period to determine Time Zero counts. The sterilized swabs were dipped in 1 ml D/E broth for 2 seconds and were used to swab the inoculated surface on control and test carriers, followed by vortexing in the rest of D/E Broth to release the bacteria. Two alternative methods were used for harvesting bacteria as follows: 1. The carriers (e.g. 2"×2" stainless steel coupons) were transferred into individual sterilized stomacher bags containing 10 mL of D/E Broth and then sonicated 20 seconds in an ultra-sonicator cleaner. Then the carriers were placed horizontally on an orbital shaker for 5 min at 250 rpm. The D/E Broth were then transferred to 15 mL conical tubes. 2. The carriers (e.g. 3"×1" glass slides) were transferred into 50 mL conical tubes containing 25 mL D/E Broth, followed by 1-minute vortexing to release the bacteria.

6. The remaining control and test carriers were held under ambient conditions for the duration of the specified study contact time of 4 hours and all carriers were evaluated in duplicate.

7. Once the contact time was reached, the control and test carriers were neutralized by D/E Broth, followed by vortexing or shaking as previously described.

8. Control and test carrier eluates were serially diluted (1:10), and spread-plated onto tryptic soy agar (TSA) plates.

9. The plates were inverted and incubated at 37° C. for 18 to 24 hours, and then scored by directly counting the colonies. Bacterial counts were calculated on a "per carrier" basis. A mean bacterial count was then computed per coating formulation per contact time, as applicable.

10. $Log_{10}$ and percent reductions were calculated for each of the test coating formulations relative to the timed control bacterial counts.

Antibacterial Testing with *E. aerogenes* 13048:

1. An overnight culture of the test organism, *E. aerogenes* 13048, was initiated by inoculating one colony from a Nutrient Agar #3 plate into 20 mL of Nutrient Broth #3, and incubating under dynamic conditions at 30° C. for 24 hours prior to testing.

2. On the date of testing, the test culture was removed from incubation, and supplemented with Fetal Bovine Serum (FBS) to achieve a final concentration of 5% (v/v).

3. An overnight density of $10^8$ to $10^9$ colony-forming units (CFU) per ml was assumed. No dilutions of the test organism were performed prior to carrier inoculation. The target inoculum density was $10^6$ to $10^7$ CFU per carrier (or per 0.010 ml).

4. Bacterial inoculum (0.010 ml) were pipetted onto the center of the control and test carriers, and spread over a surface area of ~1 in$^2$ using a sterile, bent pipette tip.

5. One set of control and test carriers was harvested/neutralized after a 20 min drying period to determine Time Zero counts. The carriers were immersed in stomacher bags containing 10 mL D/E broth, sonicated for 20 seconds, and placed on an orbital shaker for 4 min at 200 rpm to release the bacteria.

6. The remaining control and test carriers were held under ambient conditions for the duration of the specified study contact times of 1 hour or 4 hours and all carriers were evaluated in duplicate.

7. Control and test carrier eluates were serially diluted (1:10), and spread-plated onto Nutrient Agar plates.

8. The plates were inverted and incubated at 30° C. for 18 to 24 hours, and then scored by directly counting the colonies. Bacterial counts were calculated on a "per carrier" basis. A mean bacterial count was then computed per coating formulation per contact time, as applicable.

9. $Log_{10}$ and percent reductions were calculated for each of the test coating formulations relative to the timed control bacterial counts.

Surface Time-Kill Testing Procedure with *Klebsiella pneumoniae* 4352 and *S. aureus* 6538:

1. An overnight culture of the test organism, *K. pneumoniae* 4352 or *S. aureus* 6538, was initiated by inoculating one colony from a TSA plate into 20 ml of Nutrient Broth, and incubating under dynamic conditions at 37° C. for 48 hours prior to testing.

2. On the date of testing, the test culture was removed from incubation, and supplemented with Fetal Bovine Serum (FBS) to achieve a final concentration of 5% (v/v).

3. An overnight density of $10^8$ to $10^9$ colony-forming units (CFU) per ml was assumed. No dilutions of the test organism were performed prior to carrier inoculation. The target inoculum density was $10^6$ to $10^7$ CFU per carrier (or per 0.010 ml).

4. Bacterial inocula (0.010 ml) were pipetted onto the center of the control and test carriers, and spread over a surface area of ~1 in$^2$ using a sterile, bent pipette tip.

5. One set of control carriers was harvested/neutralized after a 20 min drying period to determine Time Zero counts. The carriers were placed in 50 mL conical tubes containing 25 mL D/E Broth, followed by 1-minute vortexing in the D/E Broth to release the bacteria.

6. The remaining control and test carriers were held under ambient conditions for the duration of each of the specified study contact times of 0.5 hour and 1 hour and all carriers were evaluated in triplicate.

7. Once the contact times were reached, the control and test carriers were neutralized by swabbing with D/E Broth, followed by vortexing as previously described.

8. Control and test carrier eluates were serially diluted (1:10), and spread-plated onto tryptic soy agar (TSA) plates.

9. The plates were inverted and incubated at 37° C. for 18 to 24 hours, and then scored by directly counting the colonies. Bacterial counts were calculated on a "per carrier" basis. A mean bacterial count was then computed per coating formulation per contact time, as applicable.

10. $Log_{10}$ and percent reductions were calculated for each of the test coating formulations relative to the timed control bacterial counts.

Surface Time-Kill Testing Procedure with Murine Norovirus

1. RAW (mouse macrophage) host cells were prepared in 96-well trays 24 hours prior to use in testing.

2. On the day of testing, a stock vial of test virus, murine norovirus, was removed from storage at −80° C. (titer=5× $10^8$ TCID$_{50}$ units/mL). An organic soil load (heat inactivated fetal bovine serum) was added to obtain a final concentration of 5%.

3. Control (uncoated test carriers) and the indicated coated test carriers were placed into sterile Petri dishes (one per dish) using pre-sterilized forceps.

4. Viral inocula (0.010 ml) were pipetted onto the center of the control and test carriers, and spread over a surface area of ~1 in$^2$ using a sterile, bent pipette tip.

5. One set of control carriers (per surface material type) was harvested/neutralized immediately to determine Time Zero counts by placement into sterile stomacher bags containing 3 ml of neutralizing solution (calf serum supplemented with 0.001% Na-thiosulfate and 0.001% Na-thioglycollate). The bags were stomached for 120 seconds at high speed to release the viruses from the carriers.

6. The remaining control and test carriers were held under ambient conditions for the duration of each of the specified study contact times of 4 hours and 24 hours [placement distance/configuration: ~68 inches (~1.7 m) below two full-spectrum bulbs, inoculated side facing up towards the lights)]. All carriers were observed to be dried within 10 minutes of inoculation.

7. Upon closure of the respective contact times, the control and test carriers were neutralized by placement into sterile stomacher bags containing 3 ml of neutralizing solution, followed by stomaching as previously described.

8. At the start and finish of each of the contact times, room temperature, relative humidity, and illuminance (lux) were measured and recorded.

9. Control and test carrier eluates were serially diluted (1:10) and plated in replicates of six onto RAW host cells prepared to the appropriate confluency.

10. The plates were observed every 24 to 48 hours to visualize viral cytopathic effects (CPE) and cytotoxicity.

11. Following a 9-day assay incubation period, the plates were formally scored.

12. $Log_{10}$ and percent reductions were calculated for each of the test coating formulations relative to the timed control virus counts (per surface type). However, reductions could not be computed for the 24 hour contact time due to insufficient viral recovery from the control carriers.

13. A neutralization validation was performed for each of the test coating formulations (except where indicated, due to a lack of carriers). One control carrier and one of each test carrier type were placed into stomacher bags containing 3 ml of neutralizer, and processed as previously described. The eluate was serially diluted, and low titer inoculum of the test virus (~3-$log_{10}$) was added to each of the dilution tubes per control and test carrier suspension. Aliquots (0.1 ml) of the suspensions were then plated in order to assess cytotoxic levels of the neutralized test materials.

Surface Time-Kill Testing Procedure with Feline Calicivirus (EPA-Approved Human Norovirus Surrogate) ATCC VR-782

1. CRFK (ATCC CCL-94) host cells were prepared in 96-well trays 24 hours prior to use in testing.

2. On the day of testing, a stock vial of test virus, Feline calicivirus, was removed from storage at −80° C. (titer=5× $10^8$ $TCID_{50}$ units per ml). Dilution of test virus was performed using PBS to reach $10^6$ $TCID_{50}$ units per ml. An organic soil load (heat-inactivated fetal bovine serum, FBS) was added to obtain a final concentration of 5%.

3. Control (non-coated 3"×1" glass slides) and coated test carriers were placed into sterile Petri dishes (one per dish) using pre-sterilized forceps.

4. Viral inocula (0.020 ml) were pipetted onto the center of the control and test carriers, and spread over a surface area of ~1-$in^2$ using a sterile, bent pipette tip. The target inoculum density was $10^4$ $TCID_{50}$ units per carrier.

5. One set of control carriers was harvested/neutralized immediately to determine Time Zero counts by placement into sterile stomacher bags containing 4 ml of neutralizing solution (2% FBS EMEM cell culture media). The bags were stomached for 120 seconds at high speed to release the viruses from the carriers.

6. The remaining control and test carriers were held under ambient conditions for the duration of each of the specified study contact times of 1 hour, 2 hours and 3 hours.

7. Upon closure of the respective contact times, the control and test carriers were neutralized by placement into sterile stomacher bags containing 4 ml of neutralizing solution, followed by stomaching as previously described.

8. At the start and finish of each of the contact times, room temperature, relative humidity, and illuminance (lux) were measured and recorded.

9. Control and test carrier eluates were serially diluted (1:10) and plated in replicates of six onto CRFK host cells prepared to the appropriate confluency.

10. The plates were observed every 24 to 48 hours to visualize viral cytopathic effects (CPE) and cytotoxicity.

11. Following a 6-day assay incubation period, the plates were formally scored.

12. $Log_{10}$ and percent reductions were calculated for each of the test coating formulations relative to the timed control virus counts (per surface type).

13. A neutralization validation was performed for each of the test coating formulations. One control carrier and one of each test carrier type were placed into stomacher bags containing 4 ml of neutralizer, and processed as previously described. The eluate was serially diluted, and low titer inoculum of the test virus (~3-$log_{10}$) was added to each of the dilution tubes per control and test carrier suspension. Aliquots (0.1 ml) of the suspensions were then plated in order to assess cytotoxic levels of the neutralized test materials.

Surface Time-Kill Testing Procedure with Human Norovirus (GII.4 Sydney)

1. A stock vial of test virus, human Noro virus (GII.4 Sydney), was removed from storage at −80° C. An organic soil load (positive fecal suspension) was added to obtain a final concentration of 5%.

2. 1"×1" control carriers (uncoated test carriers) and 1"×1" coated carriers were placed into sterile Petri dishes (one per dish) using pre-sterilized forceps.

3. Viral inocula (0.020 ml) were pipetted onto the center of the control and test carriers and let in dry under ambient condition.

4. One set of control carriers as well as test carriers were harvested/neutralized immediately to determine Time Zero counts by adding 1 mL D/E Broth to the carriers, followed by scraping with cell scrapers. The eluates were transferred to clean tubes for RNAase pretreatment.

5. The remaining control and test carriers were held under ambient conditions for the duration of each of the specified study contact times of 0.5 hour, 2 hours, 24 hours, 7 days and 14 days.

6. Upon closure of the respective contact times, the control and test carriers were neutralized by adding 1 mL D/E Broth to the carriers, followed by scraping with cell scrapers. The eluates were transferred to clean tubes for RNAase pretreatment as described previously.

7. Control and test carrier eluates were serially diluted (1:10) and treated with RNase to remove any RNA not protected by virus capsids.

8. Specific RNA primers were used for human Noro virus RNA amplification using Real-time quantitative Polymerase Chain Reaction (RT-qPCR). Standard virus samples were prepared with different virus titer, which were used for developing a standard curve of virus copy number versus the PCR cycle numbers obtained from RT-qPCR analysis.

9. RT-qPCR was performed on control and test carrier eluates to obtain the virus copy number based on above standard curve.

10. $Log_{10}$ reduction of virus copy number in 2030 carrier eluates at each contact time was calculated relative to the timed control virus copy numbers Surface Time-Kill Testing Procedure with *Clostridioides difficile* (*C. difficile*) ATCC 43598 Endospores 1. On the day of testing, a stock vial of *C. difficile* ATCC 43598 endospores, was removed from storage at −80° C. Dilution of test organism was performed using Phosphate Buffered Saline Tween-20 (PBS-T) media to reach $10^8$, $10^6$ and $10^4$ CFU/mL.

2. Control (uncoated 3"×1" glass slides) and coated test carriers were placed into sterile petri dishes (one per dish) using pre-sterilized forceps.

3. Spore inocula (0.020 ml) were pipetted onto the center of the control and test carriers, and spread over a surface area of ~1-in$^2$ using a sterile, bent pipette tip. The target inoculum density was $10^6$, $10^4$ and $10^2$ CFU per carrier.

4. One set of control carriers was harvested/neutralized after a 20 min drying period to determine Time Zero counts. The carriers were placed in 50 mL conical tubes containing 20 mL D/E Broth, followed by 1-minute vortexing to release the test organism.

5. The remaining control and test carriers were held under ambient conditions for the duration of each of the specified study contact times of 2 hours, 4 hours, 8 hours and 24 hours and all test carriers were evaluated in duplicates. The control carriers were evaluated in single replicate.

6. Once the contact times were reached, the control and test carriers were neutralized by 20 mL D/E Broth, followed by vortexing as previously described.

7. Control and test carrier eluates were serially diluted (1:10), and spread-plated onto Brain Heart Infusion Agar with Horse Blood and Taurocholate (BHIY-HT) media plates for the germination and cultivation of *C. difficile* spores.

8. The plates were inverted and incubated at 37° C. for 3 to 5 days, and then scored by directly counting the colonies. Bacterial counts were calculated on a "per carrier" basis. A mean bacterial count was then computed per coating formulation per contact time, as applicable.

9. $Log_{10}$ and percent reductions were calculated for each of the test coating formulations relative to the timed control bacterial counts.

Germicidal Spray Product Testing Procedure

The following procedure was used to assess capability of the antimicrobial compositions to function as contact sanitizers or disinfectants.

1. 3"×1" glass slides were washed individually with water and sterilized in a reagent alcohol bath for 1 hour.

2. The washed glass slides were transferred over flame to get rid of excess alcohol using sterile forceps and placed in a petri dish until use.

3. An overnight culture of the test organism, (e.g. *E. coli* 25922), was initiated by inoculating one colony from a TSA plate into 20 ml of TSB, and incubating under dynamic conditions at 37° C. for 24 hours prior to testing.

4. On the date of testing, the test culture was removed from incubation, 10 times dilution of the test organism using TSB were performed prior to carrier inoculation with Fetal Bovine Serum (FBS) supplement to achieve a final concentration of 5% (v/v).

5. An overnight density of $10^9$ to $10^8$ colony-forming units (CFU) per ml was assumed. The target inoculum density was $10^6$ to $10^5$ CFU per carrier (or per 0.010 ml).

6. Bacterial inoculum (0.010 ml) were pipetted onto the center of the positive control and ten test carriers, and spread over a surface area of ~1 in$^2$ area using a sterile, bent pipette tip. No bacteria inoculum was on the negative control carriers.

7. The bacteria inoculum on the positive control carrier and ten test carriers were left in the air for approximately 30 min to dry.

8. Each of the ten test carriers laying horizontally in petri dishes were sprayed with the formulation in a regular trigger sprayer for 5 seconds. The spray nozzle of the spray bottle was between 30 and 35 cm from ground and the distance from nozzle to ground was between 40 to 45 cm.

9. A neutralization validation was performed. One non-inoculated carrier laying horizontally in a petri dish was sprayed with the test formulation the same was as previous described.

10. The negative control carrier (without bacteria inoculum on the glass slides) and positive control carrier (with bacteria inoculum on the glass slides) were sprayed with sterilized de-ionized water the same way as previous described.

11. When the 10 minutes of contact time was up for each carrier, the excess amount of formulation was drained off from the test carriers and the neutralization carrier without touching petri dish (some drops may remain). Each of the test carriers and the neutralization control carrier were then transferred to a 50 mL conical tube containing 25 mL Letheen broth.

12. 0.010 mL of bacterial inoculum was pipetted into the conical tube containing neutralization control carrier to verify the complete neutralization of excessive formulation attached to the carriers with 25 mL Letheen broth.

13. All of the conical tubes were vortexed for 10 seconds and incubated for 48 hours at 37° C. for the test organism, (e.g. *E. coli* 25922). The bacteria growth was recorded in each conical tube as positive (+) or negative (○) based on the visual check.

Solution Minimal Inhibition Concentration (MIC) Testing Procedure

1. An overnight culture of the test organism (e.g. *E. coli* 25922), was initiated by inoculating one colony from a TSA plate into 20 ml of TSB, and incubating under dynamic conditions at 37° C. for 24 hours prior to testing.

2. An overnight density of $10^9$ colony-forming units (CFU) per ml was assumed. Dilution of test organism overnight culture was performed prior to inoculation using Muller Hinton Media. The inoculum density was $10^6$ CFU per mL.

3. 125 μL of sterilized PBS buffer was added to all the wells except the first column (A1, B1, C1 to H1) on a sterilized 96-well plate using an 8-channel pipettor.

4. 250 μL of the test formulations were added the first column of wells (A1, B1, C1 to G1).

5. The 8-channel pipettor was used to take 125 μL solution from the wells in the first column (A1, B1, C1 to G1) to next column (A2, B2, C2 to G2).

6. The solution in the second column (A2, B2, C2 to G2) was pipetted up and down five times to mix well with PBS buffer and then 125 μL of the solution in each well was taken to the corresponding wells in next column.

7. Step 4 was repeated until A10, B10, C10 to G10 were reached. The final 125 μL solution taken from these wells in the last column was discarded.

8. 125 μL of inoculum in Muller-Hinton media was added to each well with PBS-diluted formulations using the 8-channel pipettor. The solution was pipetted up and down five times to mix well with bacteria inoculum.

9. The plate was covered with its lid, sealed with parafilm and incubated at 37° C. for 48 hours.

10. Bacteria growth was visually checked by observing solution turbidity and MIC value of each formulation was determined.

Results

FIG. 37 sets forth a tabular summary of residual antimicrobial efficacy against *E. coli* 25922 for compositions #1 (2030$_5$) and #2 (2030$_5$A01$_5$) (see Table 21) that were coated and dried onto stainless steel test coupons. For 1-hour contact time between the inoculum and the coating, there is a significant and unexpected benefit to having triethanolamine in the coating composition (1.85 $\log_{10}$ kill without TEA in the composition versus ≥4.85 $\log_{10}$ kill with TEA in the composition). Similarly, for 4-hours contact time between the inoculum and the coating, there is a significant and unexpected benefit to having triethanolamine in the coating composition (2.80 $\log_{10}$ kill without TEA in the composition versus ≥4.68 $\log_{10}$ kill with TEA in the composition). However, it appears that a second coating of aqueous titanium sol over the organosilane homopolymer coating does not improve residual antimicrobial efficacy of the coating against *E. coli* 25922 at 1-hour and 4-hours contact times.

FIG. 38 sets forth a tabular summary of residual antimicrobial efficacy against *S. epidermidis* 12228 for compositions #1 ($2030_5$) and #2 ($2030_5 A01_5$) (see Table 21) that were coated and dried onto stainless steel test coupons. The results are similar to the *E. coli* results in that the triethanolamine provided a substantial improvement to the efficacy of the dried coating. Composition #2 ($2030_5 A01_5$) exhibited a 3.4 $\log_{10}$ kill against *S. epidermidis* 12228 at 1-hour contact time between the inoculum and the coating, and exhibited a ≥5.28 $\log_{10}$ kill against *S. epidermidis* 12228 at 4-hours contact time between the inoculum and the coating. As in the studies against *E. coli*, a coating of aqueous titanium sol over the coating of organosilane homopolymer did not improve the residual antimicrobial efficacy against *S. epidermidis* 12228.

As summarized in FIG. 39, coatings obtained by drying the aqueous organosilane homopolymer compositions #1 and #2 (Table 21) were subjected to mechanical abrasion testing to determine how effective a coating may remain after testing that correlates to frequent handling of a surface. FIG. 39 provides the results on stainless steel coupons. Coupons were first coated with the antimicrobial coating composition followed by the 0.85 wt. % titanium sol composition. Although the coating from composition #2 (Table 21) showed a much higher residual antimicrobial efficacy compared to the coating from composition #1 (Table 21), the activity was much lower after the abrasion testing, indicating the coating made from composition #2 did not exhibit very good durability. Evident too was that the amount of triethanolamine in composition #2 is overly excessive, leading to a sticky surface and oily appearance of the coating and having a negative impact on binding between the coating and the corresponding surface.

Figure 40:
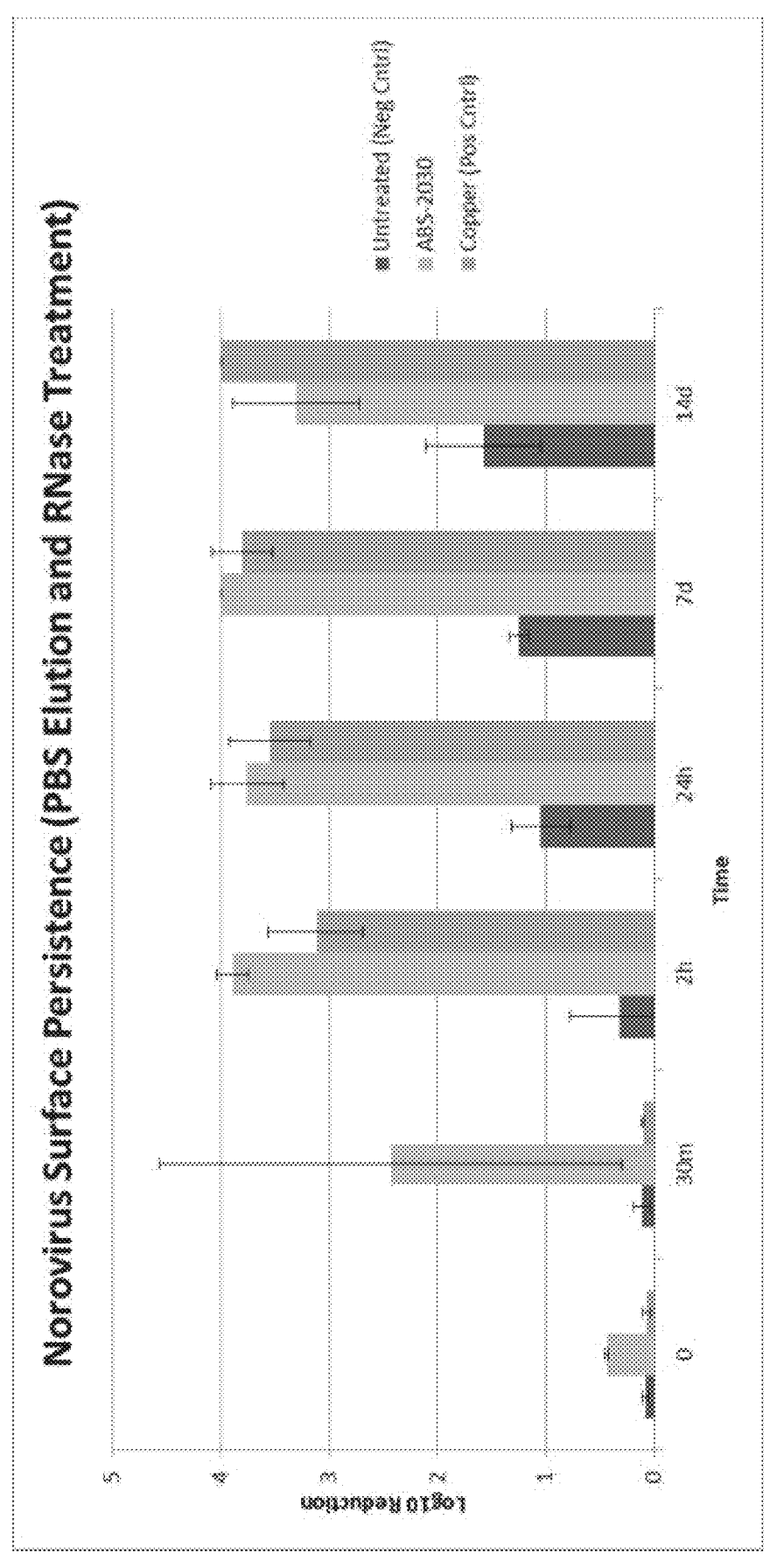
Figure 41:
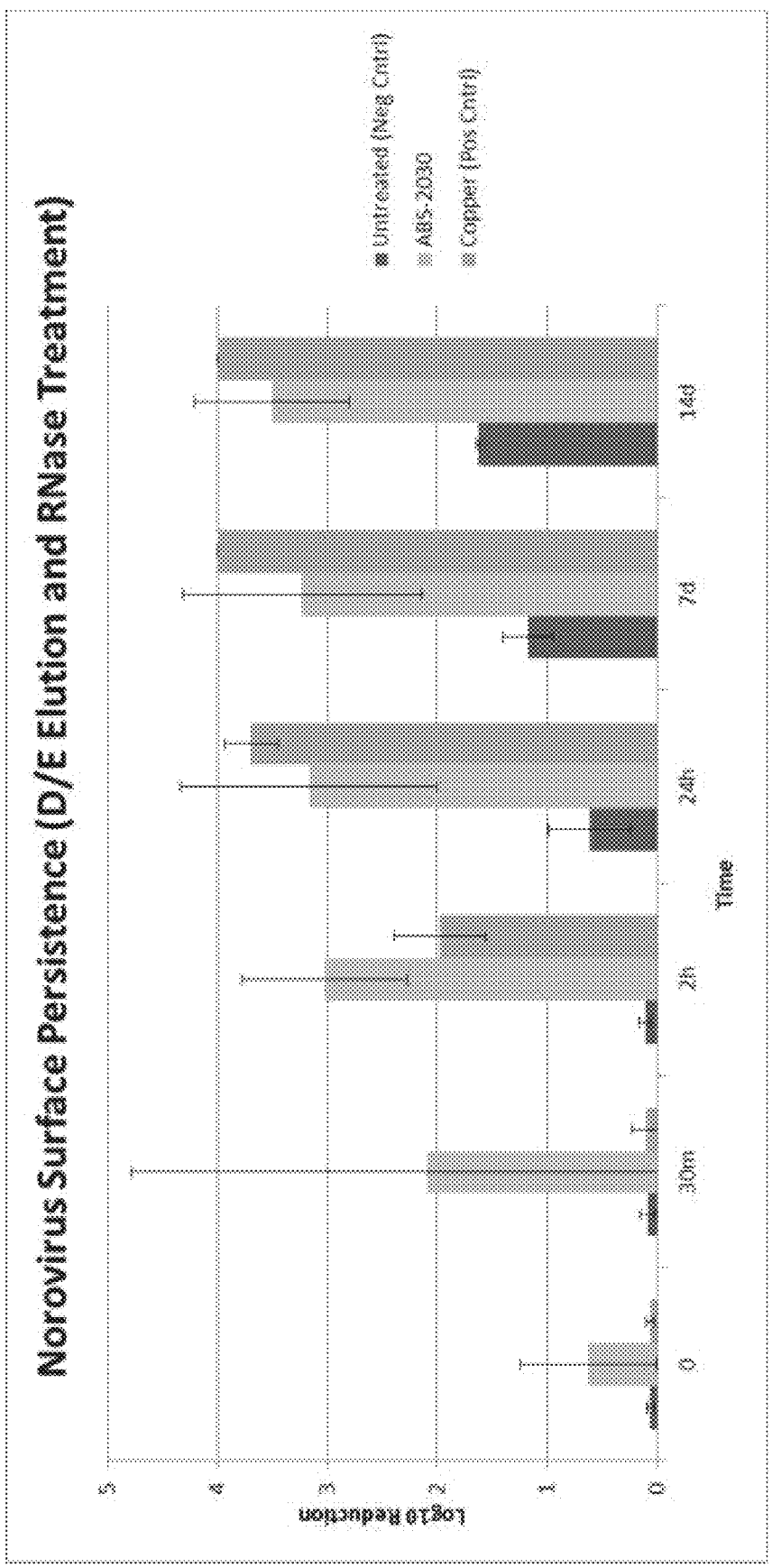

FIGS. 40 and 41 set forth the efficacy of coatings against human norovirus, with FIG. 40 showing the results upon PBS elution off the test coupons and RNase treatment and FIG. 41 showing the results upon D/E elution off the test coupons and RNase treatment. The coatings on stainless steel were made using composition #2 (Table 21) as the first step in a two-step coating also including the 0.85 wt. % titanium sol coating. As evident from the bar graphs, a coating obtained from composition #2 followed by "T" showed significant reduction of human norovirus after 2-hours contact time between the virus and the coated surface. Further, the $2030_5 A01_5 T$ coating maintained at least sanitizing level of residual efficacy (≥3 $\log_{10}$ kill) at 14-days.

FIG. 42 sets forth a comparison of residual antimicrobial efficacy between composition #1 ($2030_5$) and composition #3 ($2030_5 A01_{0.14}$) (from Table 21) against *E. coli* 25922. The coatings were prepared on stainless steel coupons by applying the indicated aqueous organosilane homopolymer followed by the aqueous 0.85 wt. % titanium sol.

The mechanical wear protocol was per the general procedures above, noting the following specifics:

1. Three 2"×2" stainless steel carriers in each test condition were selected and weighed before ABS coatings were applied, and before and after abrasion testing. All the carriers were subject to the abrasion testing directly without being weighed.
2. The wear testing was performed in batches of 3 coupons.
3. 3 layers of Scott® Original SHOP Towels™ were attached to a 333.0 g block for the wear cycles.
4. 10 wet and 10 dry cycles were performed by dragging the abrasion block over the immobilized coupons. 1 cycle=2 passes, there and back, and was completed in 5±1 seconds.
5. For the wet wear cycles, towels attached to the abrasion apparatus were sprayed for about 2 seconds with a Preval Sprayer from a distance of 75±1 cm. Wet cycles were run immediately after spraying.
6. Coupons were allowed to air dry after wet cycles before beginning the dry cycles The table at the top of FIG. 42 summarizes the efficacy against *E. coli* 25922 at 4-hours contact time between inoculum and coating, whereas the table at the bottom of FIG. 42 summarizes the weight of the coating remaining after mechanical abrasion. The coatings prepared from $2030_5 T$ and $2030_5 A01_{0.14} T$ showed similar antimicrobial activity before and after mechanical abrasion, however the $2030_5 A01_{0.14} T$ coating showed a higher weight percent of coating remaining after wear testing (98.53 wt. %), indicating the coating obtained from $2030_5 A01_{0.14} T$ has better durability over a coating obtained from $2030_5 T$.

Figure 44:
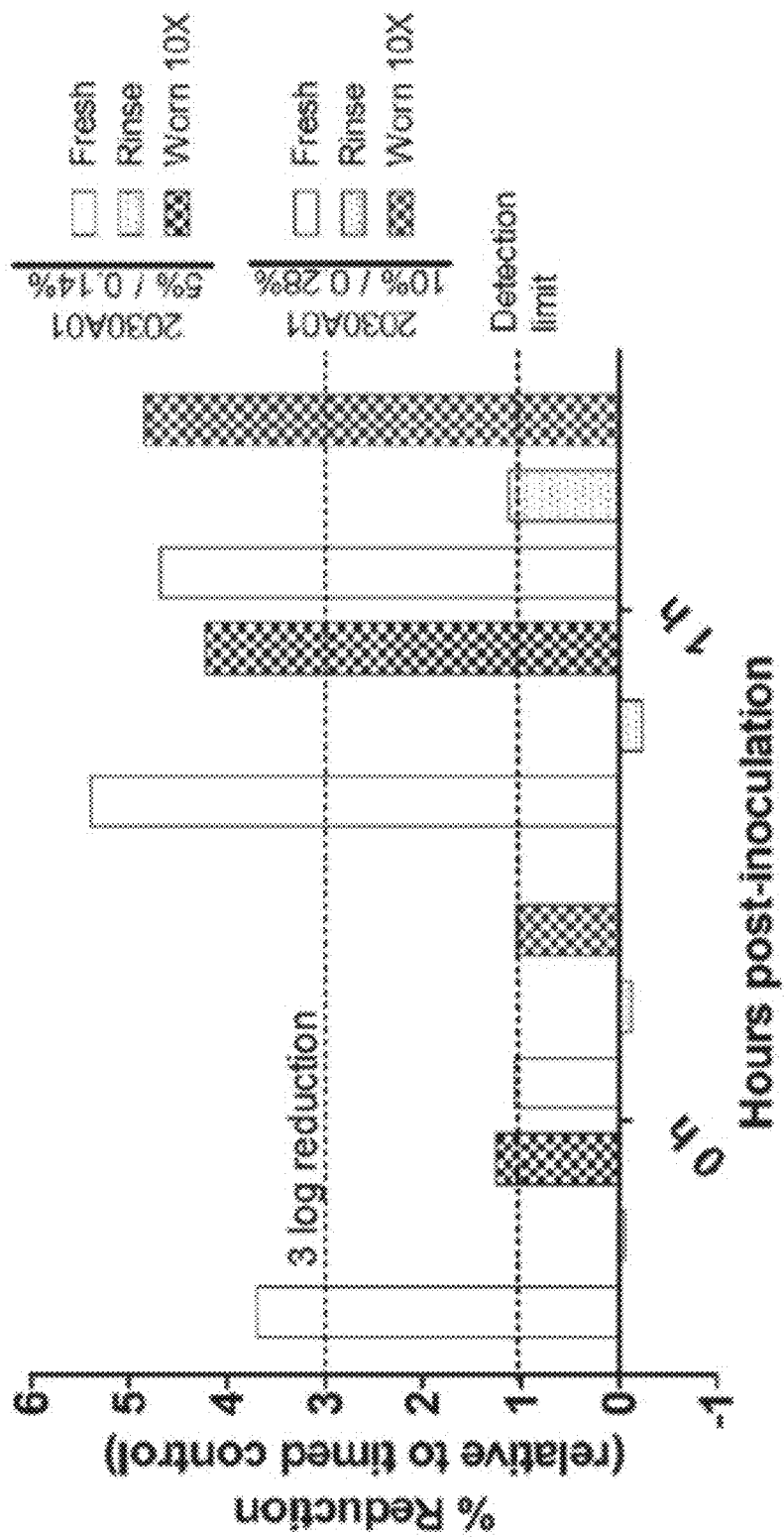

FIGS. 43 and 44 set forth residual antimicrobial efficacy for coatings obtained from antimicrobial coating compositions #3 ($2030_5 A01_{0.14}$) and #4 ($2030_{10} A01_{0.28}$) (Table 21) against *E. coli* 25922 at 1-hour contact time, with and without rinse testing and mechanical abrasion, as indicated. These coatings consisted only of the organosilane homopolymer, and did not include an overcoating of aqueous titanium sol. FIG. 44 is a graphical representation (bar graph) of the numerical data set forth in FIG. 43. As evident from the data, the coating obtained from composition #4 ($2030_{10} A01_{0.28}$) showed better durability relative to the coating obtained from composition #3 ($2030_5 A01_{0.14}$). Notably, the coating obtained from composition #4 ($2030_{10} A01_{0.28}$) not only showed at least some durability to rinsing, the coating still exhibited a 4.83 $\log_{10}$ kill against *E. coli* 25922 at 1-hour contact time even after mechanical abrasion of the coating.

Figure 45:
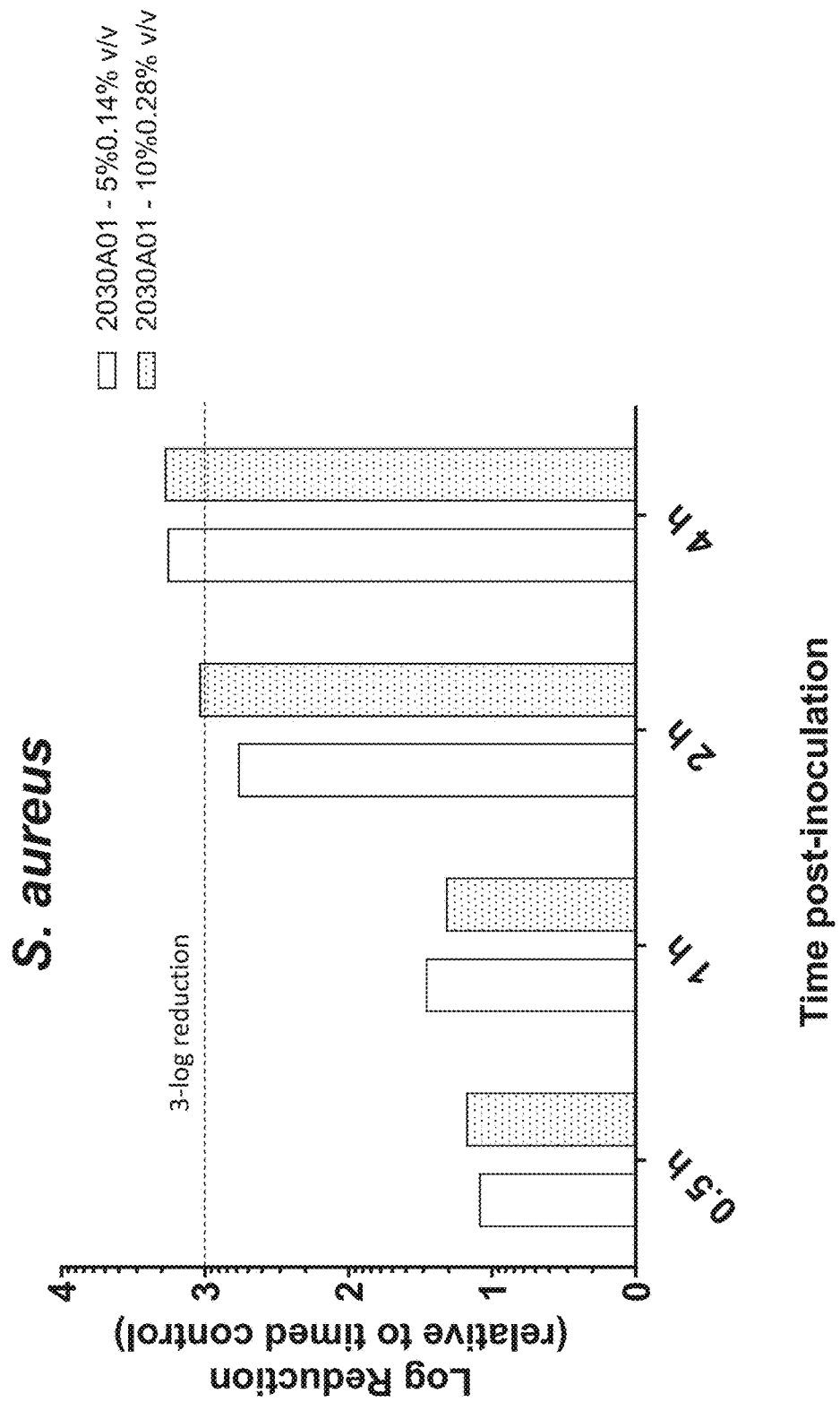
FIG. 45 sets forth surface time-kill studies against *S. aureus* 6538 for various coatings comprising 3-aminopropylsilanetriol homopolymer.

FIG. 45 sets forth residual antimicrobial efficacy for coatings obtained from antimicrobial coating compositions #3 ($2030_5 A01_{0.14}$) and #4 ($2030_{10} A01_{0.28}$) (Table 21) against *S. aureus* at 0.5, 1, 2 and 4-hour contact times. These coatings consisted only of the organosilane homopolymer, and did not include an overcoating of aqueous titanium sol. The bar graph of FIG. 45 shows that composition #4 ($2030_{10} A01_{0.28}$) kills 99.9% *S. aureus* in 2-hours and shows that both composition #3 ($2030_5 A01_{0.14}$) and composition #4 ($2030_{10} A01_{0.28}$) kills >99.95% *S. aureus* in 4-hours.

Figure 46:
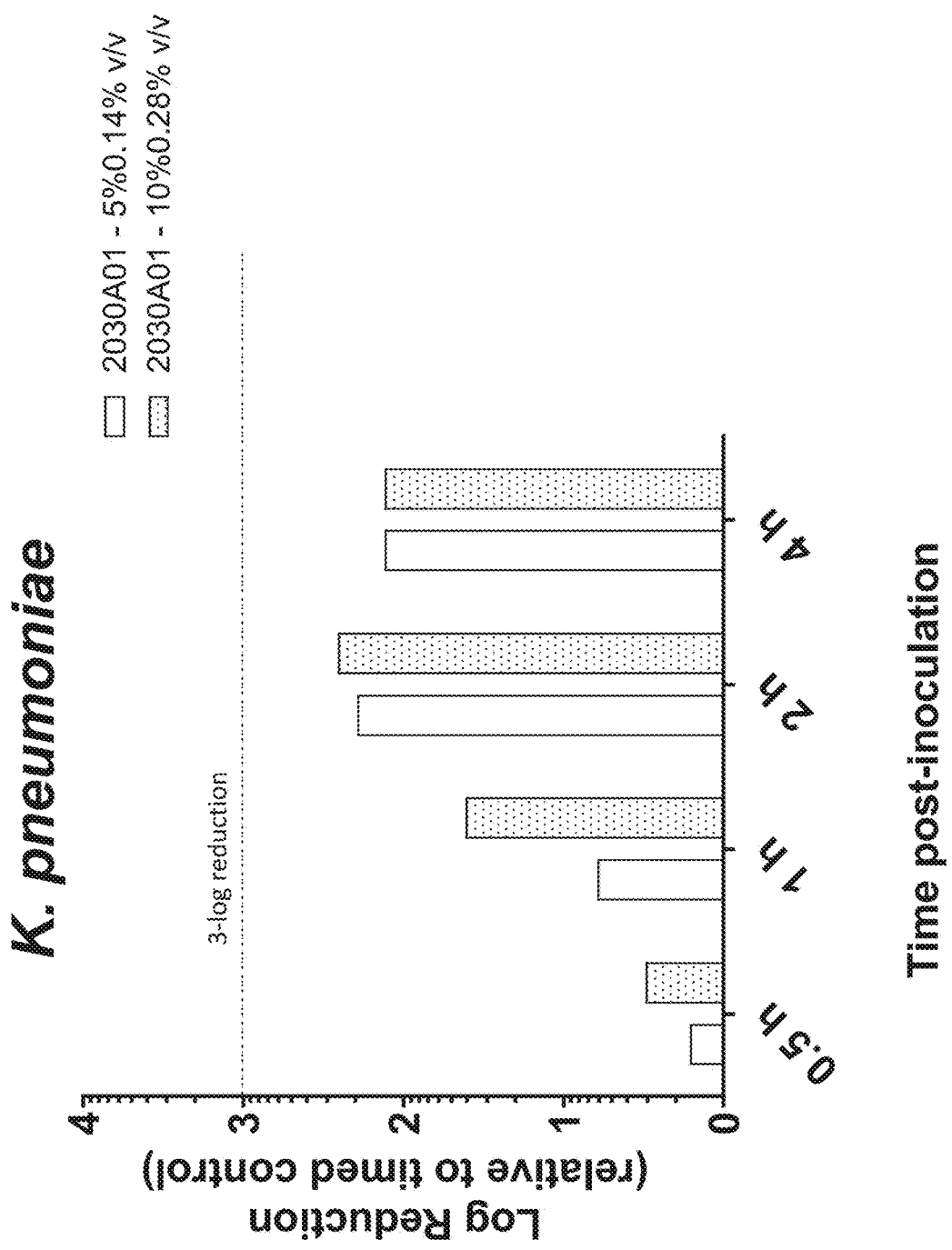
FIG. 46 sets forth surface time-kill studies against *K. pneumoniae* 4352 for various coatings comprising 3-aminopropylsilanetriol homopolymer.

FIG. 46 sets forth residual antimicrobial efficacy for coatings obtained from antimicrobial coating compositions #3 ($2030_5 A01_{0.14}$) and #4 ($2030_{10} A01_{0.28}$) (Table 21) against *K. pneumoniae* at 0.5 and 1-hour contact times. These coatings consisted only of the organosilane homopolymer, and did not include an overcoating of aqueous titanium sol. Due to a loss in viable *K. pneumoniae* control at time points above 1-hour, the data for 2-hour and 4-hour contact times were omitted. The bar graph of FIG. 46 shows that composition #4 ($2030_{10} A01_{0.28}$) kills 95% *K. pneumoniae* at 1-hour. The coating obtained from composition #4

($2030_{10}A01_{0.28}$) was more effective against *K. pneumoniae* than the coating obtained from composition #3 ($2030_5A01_{0.14}$).

Figure 47:
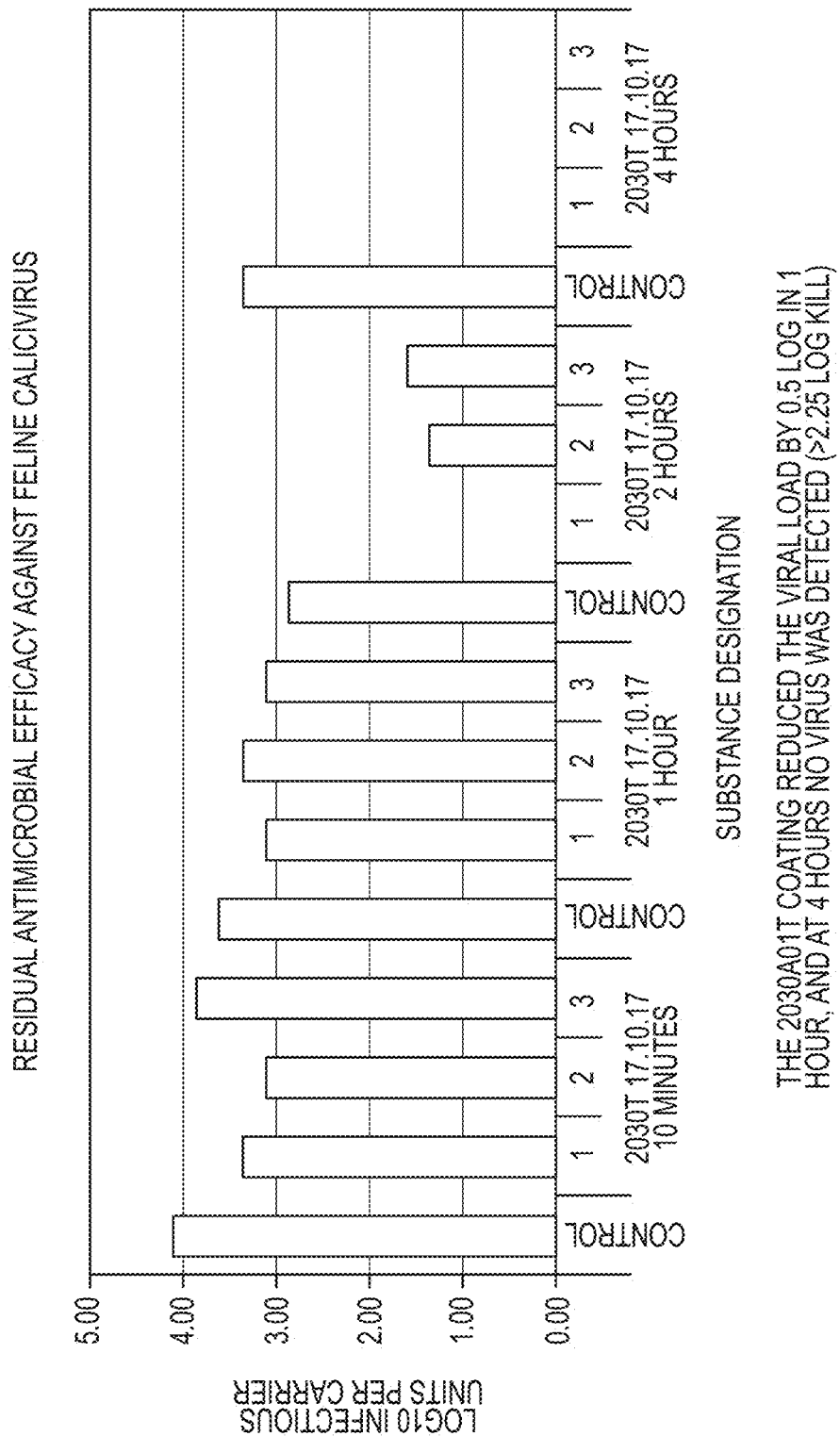
FIG. 47 sets forth surface time-kill studies against Feline Calicivirus for various coatings comprising 3-aminopropylsilanetriol homopolymer.

FIG. 47 sets forth residual antimicrobial efficacy for a coating obtained from antimicrobial coating composition #4 ($2030_{10}A01_{0.28}$) (Table 21) against Feline Calicivirus at 10-minutes, 1-hour, 2-hour and 4-hour contact times. The coating was prepared on stainless steel coupons by applying composition #4 ($2030_{10}A01_{0.28}$) (Table 21) to the test carriers followed by the aqueous 0.85 wt. % titanium sol. The $2030_{10}A01_{0.28}$T coating reduced the viral load by 0.5 log in 1-hour, and at 4-hours no virus was detected (>2.25 log kill).

Figure 48:
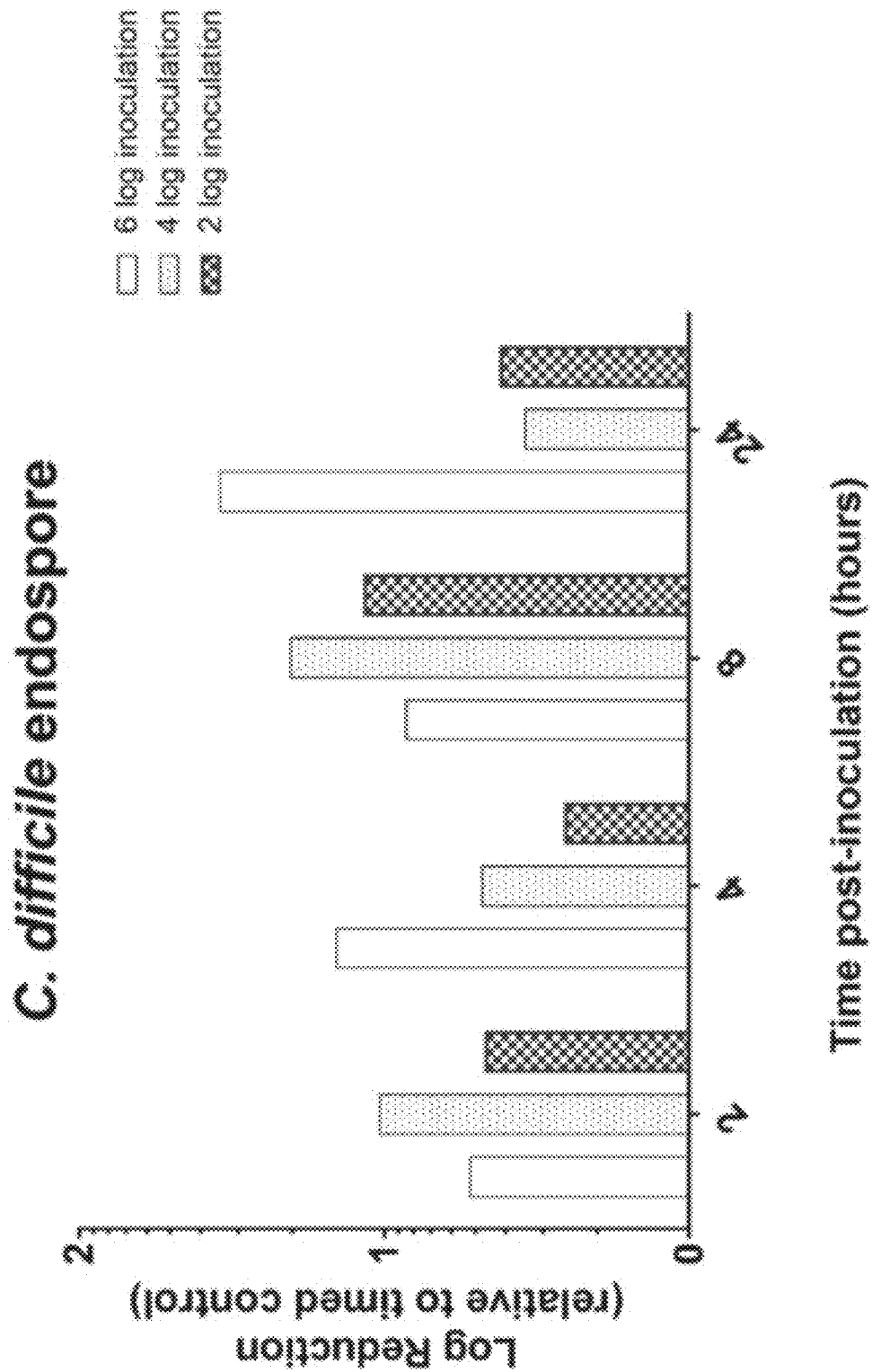
FIG. 48 sets forth surface time-kill studies against *C. difficile* 43598 endospore for various coatings comprising 3-aminopropylsilanetriol homopolymer.

FIG. 48 sets forth residual antimicrobial efficacy for a coating obtained from antimicrobial coating composition #4 ($2030_{10}A01_{0.28}$) (Table 21) against *C. difficile* endospore at 2-, 4-, 8- and 24-hour contact times and for different viral loadings (2-, 4- and 6-log inoculation). These coatings prepared on stainless steel consisted only of the organosilane homopolymer, and did not include an overcoating of aqueous titanium sol. The coating obtained from composition #4 $2030_{10}A01_{0.28}$ exhibited a 1.3 $\log_{10}$ reduction of a 6-log inoculation of *C. difficile* after 24 hours.

Composition #4 ($2030_{10}A01_{0.28}$) (Table 21) was tested for its usefulness as a germicidal spray product. Thus, the antimicrobial coating composition was used directly as a contact sanitizer/disinfectant rather than applying the composition to a surface and drying the composition into a thin film.

FIG. 49 sets forth the results of a small-scale germicidal spray test using composition #4 ($2030_{10}A01_{0.28}$) (Table 21) against three organisms, *E. coli* 25922, *S. epidermidis* 12228 and *E. aerogenes* 13048. As shown in the table of FIG. 49, composition #4 ($2030_{10}A01_{0.28}$) (Table 21) performed well against *E. coli* 25922 and *E. aerogenes* 13048, achieving >4 log reduction in 10-minutes. However, composition #4 ($2030_{10}A01_{0.28}$) (Table 21) did not perform well against *S. epidermidis* 12228 as a germicidal spray.

Example VII

This example discloses various aqueous antimicrobial coating compositions comprising 3-aminopropylsilanetriol homopolymer, 3-(trihydroxysilyl)propyl dimethyloctadecyl ammonium chloride homopolymer, 3-chloropropylsilanetriol homopolymer and triethanolamine. In various tests, a composition comprising only 3-(trihydroxysilyl)propyl dimethyloctadecyl ammonium chloride homopolymer, 3-chloropropylsilanetriol homopolymer and triethanolamine, and a composition comprising only 3-aminopropylsilanetriol homopolymer and triethanolamine, are used as control compositions where indicated.

In these examples, an aqueous antimicrobial coating composition comprises:

(a) an organosilane homopolymer having the polymeric structure,

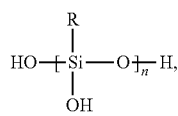

wherein:
n=3 to about 30; and R=—$(CH_2)_3$—$NH_2$;

(b) an organosilane homopolymer having the polymeric structure,

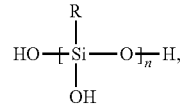

wherein:
n≥2; and R=—$(CH_2)_3$—$^+N(CH_3)_2(C_{18}H_{37})Cl^-$;

(c) an organosilane homopolymer having the polymeric structure,

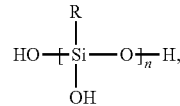

wherein:
n≥2; and R=—$(CH_2)_3$—Cl; and
triethanolamine.

The compositions in this example were formulated by diluting, in water, 3-(trihydroxysilyl)propyl dimethyloctadecyl ammonium chloride ("DMOD"), 3-chloropropyltrimethoxysilanetriol ("CPTMS"), 3-APTES (or simply "APTES"), and triethanolamine ("TEA"), each at the weight percentages shown in the table of FIG. 50. The compositions were evaluated for MIC, residual antimicrobial efficacy and rinse and abrasion durability in accordance with the procedures detailed in EXAMPLE VI.

FIG. 50 sets forth a table showing the compositions of nine (9) aqueous antimicrobial coating compositions comprising mixtures of 3-aminopropylsilanetriol homopolymer, 3-(trihydroxysilyl)propyl dimethyloctadecyl ammonium chloride homopolymer, 3-chloropropylsilanetriol homopolymer, and triethanolamine, remainder water. Also shown in the first row of the table ("2030 #4") is a control composition consisting of composition #4 ($2030_{10}A01_{0.28}$) (from Table 21, above) and, in the last row of the table, a control composition ("2015") consisting essentially of 0.75 wt. % 3-(trihydroxysilyl)propyl dimethyloctadecyl ammonium chloride, 0.120 wt. % 3-chloropropyltrimethoxysilanetriol ("CPTMS") and 0.45 wt. % triethanolamine, remainder water. FIG. 50 shows the MIC results against *S. epidermidis* 12228 for these nine (9) experimental compositions compared to the 2030 #4 and 2015 control compositions.

FIG. 51 sets forth a tabular summary of MIC results against *E. coli* 25922 for these nine (9) experimental compositions compared to the 2030 #4 and 2015 control compositions.

The nine (9) experimental mixtures of 3-aminopropylsilanetriol homopolymer, 3-(trihydroxysilyl)propyl dimethyloctadecyl ammonium chloride homopolymer, 3-chloropropylsilanetriol homopolymer, and triethanolamine were also used as antimicrobial coating compositions to form dried coatings on stainless steel carriers for surface time-kill studies.

FIG. 52 sets forth a tabular summary of the residual antimicrobial efficacy of the coatings formed from each of the nine (9) experimental mixtures, along with the control coatings obtained from application of control 2030 #4 and 2015 to test carriers against *S. epidermidis* 12228 and *E. coli*

25922 at 2-hours contact time. As seen in the table of FIG. 52, each of the nine (9) experimental mixtures (except for "2015-7" and "2015") and 2030 composition #4 as a control exhibited substantially the same residual self-sanitizing activity against *S. epidermidis* 12228, about a 5.37 $\log_{10}$ reduction after 2-hour contact time. Also, each of the nine (9) experimental mixtures and 2030 composition #4 as a control exhibited substantially the same residual self-sanitizing activity against *E. coli* 25922, about a 4.92 $\log_{10}$ reduction after 2-hours contact time.

Example VIII

This example discloses various aqueous antimicrobial coating compositions comprising unique organosilane homopolymers with multiple amino functionality, wherein the compositions optionally include at least one amine, such as triethanolamine.

In these examples, aqueous antimicrobial coating compositions comprise:

(a) at least one organosilane homopolymer having the polymeric structure,

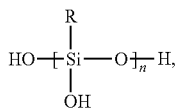

wherein:
$n \geq 2$;
R=
—$(CH_2)_3$—NH—$(CH_2)_2$—$NH_2$;
—$(CH_2)_3$—NH—$(CH_2)_2$—NH—$(CH_2)_2$—$NH_2$;
—$(CH_2)$—NH—$(CH_2)_6$—$NH_2$;
—$(CH_2)_3$—NH—$(CH_2)_3$—$Si(OR^{12})_3$, wherein $R^{12}$=H, —$CH_3$ or —$CH_2CH_3$; or
—$(CH_2)_3$—NH—$(CH_2)_2$—NH—$(CH_2)_3$—$Si(OR^{12})_3$, wherein $R^{12}$=H, —$CH_3$ or —$CH_2CH_3$; and (b) optionally, at least one amine.

In certain examples, an aqueous antimicrobial coating composition consists essentially of an organosilane homopolymer having the polymeric structure,

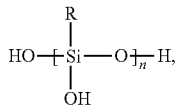

wherein:
$n \geq 2$; and R=—$(CH_2)_3$—NH—$(CH_2)_2$—$NH_2$; with the remainder being water.

In certain examples, an aqueous antimicrobial coating composition consists essentially of an organosilane homopolymer having the polymeric structure,

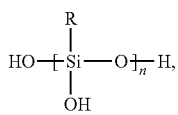

wherein:
$n \geq 2$; and R=—$(CH_2)_3$—NH—$(CH_2)_2$—NH—$(CH_2)_2$—$NH_2$; with the remainder being water.

In certain examples, an aqueous antimicrobial coating composition consists essentially of an organosilane homopolymer having the polymeric structure,

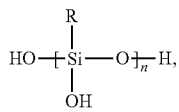

wherein:
$n \geq 2$; and R=—$(CH_2)$—NH—$(CH_2)_6$—$NH_2$; with the remainder being water.

These compositions were evaluated for MIC and were also coated onto various test coupons for evaluation of residual antimicrobial efficacy in accordance with the procedures detailed in EXAMPLE VI. In the various data summary tables, shorthand notations for these silanes are used, as follows:

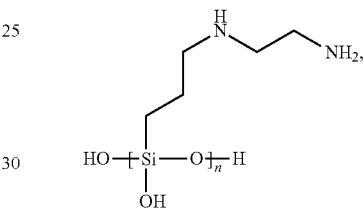

is referred to as "0590."

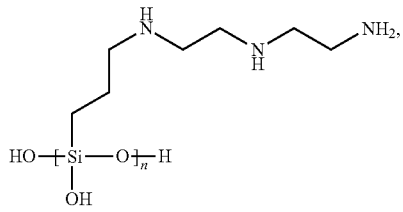 [SMILES: NCCNCCNCCC[Si](O)(O)O]

is referred to as "8398."

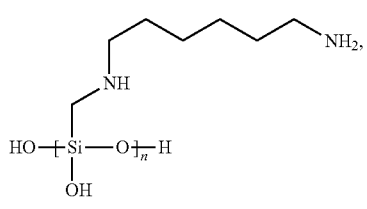 [SMILES: NCCCCCCNC[Si](O)(O)O]

is referred to as "0592."

FIG. 53 sets forth a table showing 0590, 8398, and 0592 aqueous compositions. Each of these aqueous antimicrobial coating compositions consist essentially of the indicated organosilane at 10% v/v, remainder water. These experimental organosilane compositions did not include triethanolamine. For the various efficacy tests, both a 9.4 wt. % or 10 vol. % actives 3-APTES aqueous solution without triethanolamine (herein, "$2030_{10}$"), and composition #4 ($2030_{10}A01_{0.28}$) (from Table 21 above), were used as controls and for comparison purposes. The table in FIG. 53 shows the MIC determinations for these aqueous compositions against *S. epidermidis* 12228. All of the tested compositions exhibited antimicrobial activity against *S. epidermidis* 12228, including the three compositions having the novel organosilane homopolymers. Organosilane 8398 appears to have some advantages over the other two novel organosilanes, showing the lowest MIC level for *S. epidermidis* 12228.

FIG. 54 summarizes the MIC determinations for these aqueous compositions against *E. coli* 25922. All of the tested compositions exhibited antimicrobial activity against *E. coli* 25922, including the three compositions having the novel organosilane homopolymers. Organosilane 8398 and organosilane 0592 again appear to have some advantages over the other novel organosilane 0590, showing the lower MIC level for *E. coli* 25922.

These aqueous antimicrobial coating compositions were also disposed onto stainless steel carriers where the compositions dried into coatings that exhibited residual antimicrobial efficacy against both *S. epidermidis* 12228 and *E. coli* 25922 inoculated onto the coatings and left for 2-hours contact time.

FIG. 55 summarizes the residual self-sanitizing efficacy for these coatings. All of the coatings exhibited at least sanitizing level of residual efficacy against *S. epidermidis* 12228 and *E. coli* 25922, including the three novel organosilane coatings. Organosilane 8398 again appears to have some advantages over the other two novel organosilanes, showing the highest efficacy against *S. epidermidis* 12228.

Example IX—Sterilization Station Example

Figure 3:
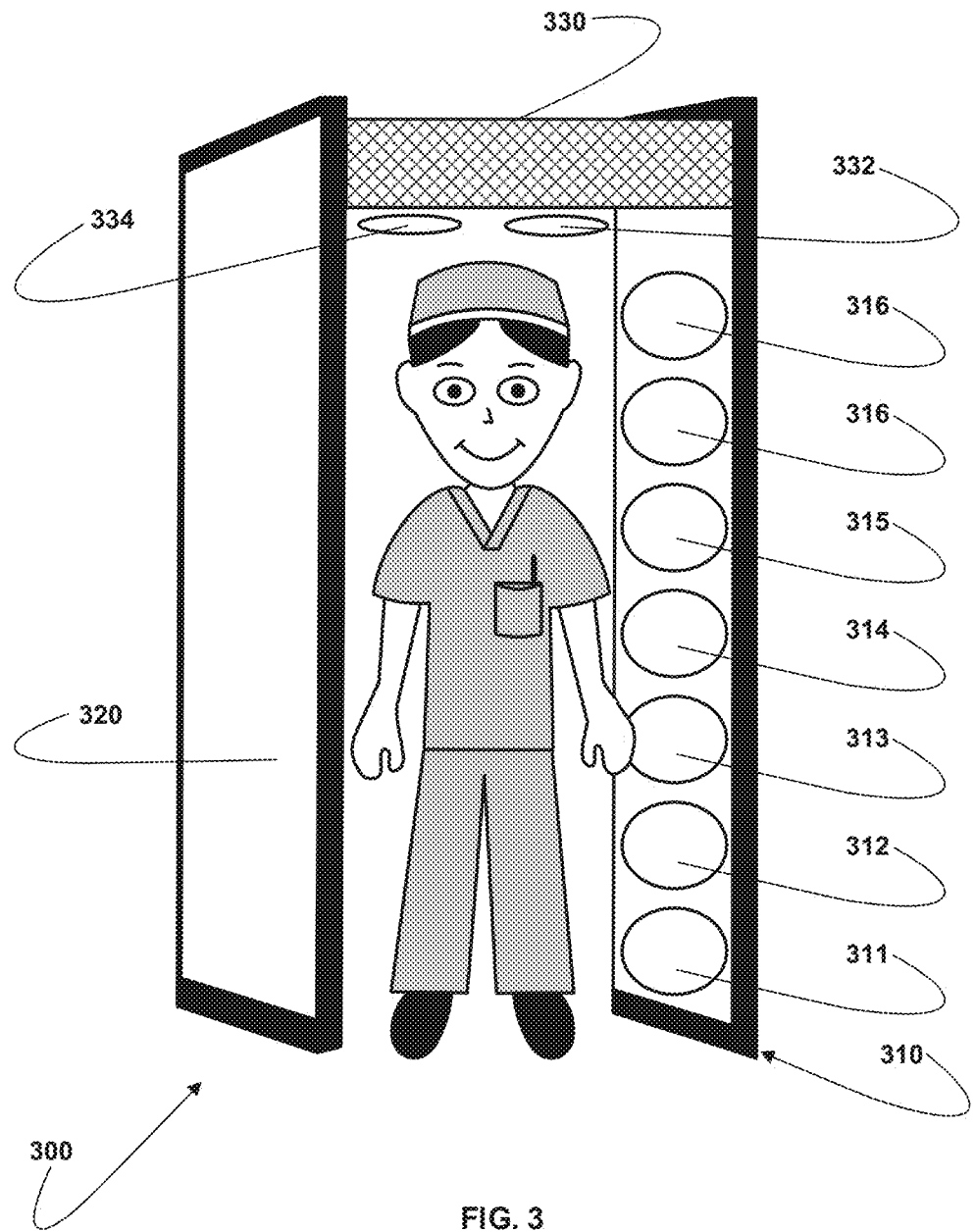
FIG. 3 illustrates sterilizing station 300, in accordance with various embodiments.

Referring now to FIG. 3, the sterilizing station 300 comprises a "walk through" assembly having two opposing sides 310 and 320 which are joined by top 330. In the illustrated embodiment of FIG. 3, side 310 comprises a plurality of UV light emitters 311, 312, 313, 314, 315, 316, and 317, where that plurality of UV emitters face the interior, i.e. walking space portion, of sterilizing station 300. In other embodiments, the sterilizing station 300 comprises fewer than seven (7) UV emitters per side. In various embodiments, the sterilizing station comprises more than seven (7) UV emitters per side.

Side 320 is similarly formed to include a plurality of UV emitters, where each of those UV emitters face the interior, i.e. walking space portion, of sterilizing station 300. The plurality of UV emitters disposed on the interior portion of side 310 have a facing relationship with the plurality of UV emitters disposed on the interior portion of side 320.

Further in the illustrated embodiment of FIG. 3, top portion 330 comprises a plurality of UV emitters, i.e. UV emitters 332 and 334, where those UV emitters face downwardly. In other embodiments, top portion 330 comprises more than two (2) UV emitters.

The illustrated embodiment of FIG. 3 shows a medical practitioner walking through sterilizing station 300. The medical practitioner is wearing a scrub suit, the various pieces of which have been coated on the exterior surface with the coating composition. As the practitioner walks through sterilizing station 300, the plurality of UV emitters disposed on sides 310 and 320, and the plurality of UV emitters disposed on top 330, are energized thereby maximizing the photocatalytic effect of the coating. Enhancing the photocatalytic activity of the coating maximizes the production of high energy, atomic oxygen species at the surface of scrub suit pieces, thereby, effectively sterilizing the exterior surfaces of all scrub suit articles.

While the various embodiments have been illustrated in detail, it should be apparent that modifications and adaptations to those embodiments may occur to one skilled in the art without departing from the scope as set forth herein.

Antimicrobial coating compositions, methods of applying antimicrobial coating compositions and antimicrobial coatings on surfaces are provided. When a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in various embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or system or any components thereof or methods of making and using same to address each and every problem sought to be solved by the present disclosure, for it to be encompassed by the present claims.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

Reference throughout this specification to "one embodiment," "preferred embodiments", "an embodiment," "various embodiments" or similar language means that a particular feature, structure, or characteristic described in connection with the embodiment may be included in various embodiments, but the feature, structure, or characteristic may be included in any of the embodiments.

The described features, structures, or characteristics of the disclosure may be combined in any suitable manner in various embodiments. In the description, numerous specific details are recited to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

The invention claimed is:

1. An aqueous antimicrobial coating composition comprising:
an organosilane homopolymer having the polymeric structure:

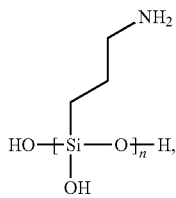

wherein n≥2;
an organosilane homopolymer having the polymeric structure:

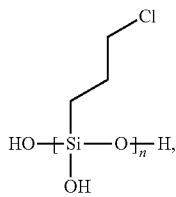

wherein n≥2; and
an organosilane homopolymer having the polymeric structure:

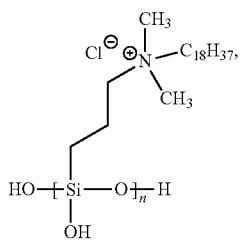

wherein n≥2.

2. The aqueous antimicrobial coating composition of claim 1, further comprising from about 0.01 wt. % to about 5.0 wt. % of at least one amine, based on the total weight of the composition, wherein the at least one amine has the structure $R^9R^{10}R^{11}N$, wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12.

3. The aqueous antimicrobial coating composition of claim 2, wherein the at least one amine comprises an amino alcohol.

4. The aqueous antimicrobial coating composition of claim 2, wherein the at least one amine is selected from the group consisting of monoethanolamine, diethanolamine, triethanolamine, and mixtures thereof.

5. The aqueous antimicrobial coating composition of claim 2, wherein the at least one amine comprises triethanolamine.

6. The aqueous antimicrobial coating composition of claim 5, wherein the triethanolamine is present at from about 0.01 wt. % to about 1.0 wt. %, based on the total weight of the composition.

7. The aqueous antimicrobial coating composition of claim 5 consisting essentially of:
a total of from about 0.01 wt. % to about 15 wt. % of a mixture of 3-aminopropylsilanetriol homopolymer having a chain length distribution of n=3 to about 30, 3-chloropropylsilanetriol homopolymer having a chain length distribution of n≥2, 3-(trihydroxysilyl)propyl dimethyloctadecyl ammonium chloride homopolymer having a chain length distribution of n≥2;
from about 0.01 wt. % to about 5.0 wt. triethanolamine; and
water.

8. The aqueous antimicrobial coating composition of claim 1, wherein the organosilane homopolymers are present in the aqueous antimicrobial coating composition in total at from about 0.01 wt. % to about 15 wt. %, based on the total weight of the composition.

9. The aqueous antimicrobial coating composition of claim 1, wherein the organosilane homopolymers present in the aqueous antimicrobial coating composition are 3-aminopropylsilanetriol homopolymer, having a chain length distribution of n=2 to about 30; 3-chloropropylsilanetriol homopolymer, having a chain length distribution of n≥2; and 3-(trihydroxysilyl)propyl dimethyloctadecyl ammonium chloride homopolymer having a chain length distribution of n≥2.

10. A method of preparing an antimicrobial coating on a surface, the method comprising:
(a) disposing on the surface an aqueous antimicrobial coating composition comprising:
an organosilane homopolymer having the polymeric structure:

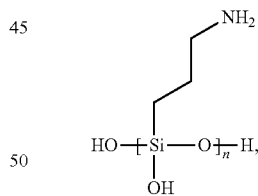

wherein n≥2;
an organosilane homopolymer having the polymeric structure:

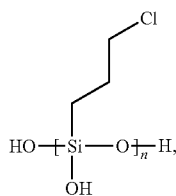

wherein n≥2; and an organosilane homopolymer having the polymeric structure:

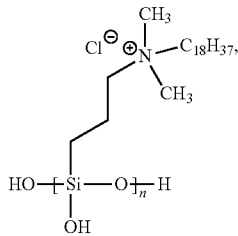

wherein n≥2; and (b) allowing the aqueous antimicrobial coating composition thus disposed on the surface to dry.

11. The method of claim 10, wherein the aqueous antimicrobial coating composition further comprises from about 0.01 wt. % to about 5.0 wt. % of at least one amine, based on the total weight of the aqueous antimicrobial coating composition, wherein the at least one amine has the structure $R^9R^{10}R^{11}N$ wherein $R^9$, $R^{10}$, and $R^{11}$ are independently H, alkyl, substituted alkyl, aryl, substituted aryl or cyclic, having a molecular weight of less than about 200 g/mole and a pKa of from about 7 to about 12.

12. The method of claim 11, wherein the at least one amine comprises an amino alcohol.

13. The method of claim 11, wherein the at least one amine is selected from the group consisting of monoethanolamine, diethanolamine, triethanolamine, and mixtures thereof.

14. The method of claim 11, wherein the at least one amine comprises triethanolamine.

15. The method of claim 14, wherein the triethanolamine is present in the aqueous antimicrobial coating composition at from about 0.01 wt. % to about 1.0 wt. %, based on the total weight of the aqueous antimicrobial coating composition.

16. The method of claim 14, wherein the aqueous antimicrobial coating composition consists essentially of:
a total of from about 0.01 wt. % to about 15 wt. % of a mixture of 3-aminopropylsilanetriol homopolymer having a chain length distribution of n=3 to about 30, 3-chloropropylsilanetriol homopolymer having a chain length distribution of n≥2, 3-(trihydroxysilyl)propyl dimethyloctadecyl ammonium chloride homopolymer having a chain length distribution of n≥2;
from about 0.01 wt. % to about 5.0 wt. triethanolamine; and
water.

17. The method of claim 10, wherein the organosilane homopolymers present in the aqueous antimicrobial coating composition are 3-aminopropylsilanetriol homopolymer, having a chain length distribution of n=2 to about 30; 3-chloropropylsilanetriol homopolymer, having a chain length distribution of n≥2; and 3-(trihydroxysilyl)propyl dimethyloctadecyl ammonium chloride homopolymer having a chain length distribution of n≥2.

18. The method of claim 10, wherein the organosilane homopolymers are present in the aqueous antimicrobial coating in total at from about 0.01 wt. % to about 15 wt. %, based on the total weight of the composition.

* * * * *